US005874080A

United States Patent [19]
Hébert et al.

[11] Patent Number: 5,874,080
[45] Date of Patent: Feb. 23, 1999

[54] ANTI-IL-8 MONOCLONAL ANTIBODIES FOR TREATMENT OF ASTHMA

[75] Inventors: Caroline A. Hébert, San Francisco; Rhona C. Kabakoff, Pacifica; Mark W. Moore, San Francisco, all of Calif.

[73] Assignee: Genentech, Inc., South San Francisco, Calif.

[21] Appl. No.: 491,334

[22] Filed: Jun. 27, 1995

Related U.S. Application Data

[63] Continuation-in-part of Ser. No. 398,611, Mar. 1, 1995, which is a continuation-in-part of Ser. No. 205,864, Mar. 3, 1994, abandoned.

[51] Int. Cl.$^6$ .................. A61K 39/395; C07K 16/24; C07K 16/00
[52] U.S. Cl. .................. 424/145.1; 424/158.1; 530/388.23; 530/587.3
[58] Field of Search .............. 424/145.1, 158.1; 530/388.23, 387.3

[56] References Cited

U.S. PATENT DOCUMENTS

| | | | |
|---|---|---|---|
| 4,816,567 | 3/1989 | Cabilly et al. | 530/387 |
| 5,290,550 | 3/1994 | Fisher et al. | 424/85.2 |

FOREIGN PATENT DOCUMENTS

| | | | |
|---|---|---|---|
| 454225 A1 | 10/1991 | European Pat. Off. | C12P 21/08 |
| 519728 A2 | 12/1992 | European Pat. Off. | C12P 21/08 |
| WO 92/00327 | 1/1992 | WIPO | C07K 13/00 |
| WO 92/01054 | 1/1992 | WIPO | C12N 15/19 |
| WO 92/04372 | 3/1992 | WIPO | C07K 7/00 |
| WO 92/06196 | 4/1992 | WIPO | C12N 15/19 |
| WO 92/06697 | 4/1992 | WIPO | A61K 35/14 |
| WO 92/08474 | 5/1992 | WIPO | A61K 37/02 |
| WO 94/04173 | 3/1994 | WIPO . | |
| WO 95/23865 | 9/1995 | WIPO . | |

OTHER PUBLICATIONS

Boylan et al., "Evidence of a role for mesothelial cell-–derived interleukin 8 in the pathogenesis of asbestos–induced pleurisy in rabbits" *J. Clin. Invest.* 89:1257–1267 (1992).

Boylan et al., "Interleukin–8 is a major component of pleural liquid chemotactic activity in a rabbit model of endotoxin pleurisy" *Amer. J. Physiol.* 267(2):L137–L144 (1994).

Broaddus et al., "Interleukin–8 is a major neutrophil chemotactic factor in pleural liquid of patients with empyema" *Amer. Rev. Resp. Disease* 146:825–830 (1992).

Stockley, Robert A., "Role of Inflammation in Respiratory Tract Infections" *Amer. J. Med.* 99(Supp. 6B) :8S–13S (1995).

Bellini et al., "Respiratory pathophysiologic responses: Bronchial epithelial cells of patients with asthma release chemoattractant factors for T lymphocytes" *J. Allergy Clin. Immunol.* 92(3):412–424 (1993).

Bittleman & Casale, "Allergic models and cytokines" *Am. J. Respir. Crit. Care Med.* 150(5):S72–S76 (1994).

Cacalano et al., "Neutrophil and B cell expansion in mice that lack the murine IL–8 receceptor homolog" *Science* 265:682–684 (Jul. 1994).

Casini–Raggi et al., "A specfic monoclonal antibody (MoAb) against interleukin–8 (IL–8) suppresses inflammation in rabbit immune colitis" *Immunology, Microbiology & Inflammatory Disorders* (abstract only) 106(4 Supp.) :A661 (Apr. 1994).

Corrigan et al., "Cultured peripheral blood mononuclear cells derived from patients with acute severe asthma (Status Asthaticus) spontaneously elaborate a neutrophil chemotactic activity distinct from interleukin–8$^{1-3}$" *Am. Rev. Respir. Dis.* 143(3) :538–544.

Cross et al., "Choice of Bacteria in Animal Models of Sepsis" *Inf. & Immunity* 61(7) :2741–2747 (Jul. 1993).

Dubois et al., "IL–4–induced migration of eosinophils in allergic inflammation" *Annals New York Acad. Science* 725:268–273 (1993).

Erger et al., "Interleukin–8 is a potent mediator of eosinophil chemotaxis through endothelium and epithelium" *Am. J. Physiol.* 268(1):L117–L122 (1995).

Fahy, J.V. et al., "Respiratory pathophysiologic responses: prominant neutrophilic inflammation in sputum from subjects with asthma exacerbation" *J. Allergy & Clincal Immunol.* 95(4):843–852 (1995).

Fisher, R.H. et al., "Interleukin–8 (IL–8) reverses hyperreactivity and blocks allergen–induced late phase reactions" *J. Allergy Clin. Immunol.* (abstract only) 89(1 of 2):p. 165, abs 81 (1992).

Hallsworth et al., "Selective enhancement of GM–CSF, TNF–α, IL–1β and IL–8 production by monocytes and macrophages of asthmatic subjects" *Eur. Respir. J.* 7(6):1096–1102 (1994).

Harris et al., "Therapeutic antibodies—the coming of age" *TIBECH* 11:42–44 (Feb. 1993).

Hebert et al., "Interleukin–8: A Review" *Cancer Investigation* 11(6):743–750 (1993).

Hood et al., "IL–8 levels are increased in the plasma of atopic non–asthmatic, but not atopic subjects" *Eur. Respir. J.* 7(Supp. 8)Lp. 434s, abs 1966 (1994).

in't Veen et al., "Interleukin–8(IL–8) and monocyte chemoattractant protein–1 (MCP–1) are elevated in induced sputum in asthma" *Eur. Respir. J.* 7(Suppl 18) :p. 19S, abs 0170 (1994).

Kameyoshi et al., "Cytokine RANTES released by thrombin–stimulated platelets is a potent attractant for human eosinophils" *Journal of Experimental Medicine* 176(2):587–592 (1992 1992).

Ko et al., "A sensitive enzyme–linked immunosorbent assay for human interleukin–8" *J. Immunol. Methods* 149:227–235 (1992).

(List continued on next page.)

*Primary Examiner*—Susan A. Loring
*Attorney, Agent, or Firm*—Richard B. Love

[57] ABSTRACT

Methods are provided for the treatment of asthma with anti-IL-8 monoclonal antibodies.

13 Claims, 39 Drawing Sheets

OTHER PUBLICATIONS

Marini et al., "Expression of the potent inflammatory cytokines, granulocyte–macrophage–colony–stimulating factor and interleukin–6 and interleukin–8, in bronchial epithelial cells of patients with asthma" *J. Allergy Clin. Immuno.* 89(5):1001–1009 (1992).

Mulligan et al., "Inhibition of Lung Inflammatory Reactions in Rats by an Anti–Human IL–8 Antibody" 150(12):5585–5595 (Jun. 15, 1993).

Sartor, R. Balfour, "Animal Models of Intestinal Inflammation—Relevance to Inflammatory Bowel Disease" *Inflammatory Bowel Disease* (Chapter 18), MacDermott et al., New York: Elsevier pp. 337–353 (1992).

Sekido et al., "Prevention of lung reperfusion injury in rabbits by a monoclonal antibody against interleukin–8" *Nature* 365:654–657 (Oct. 14, 1993).

Smith, Diana et al., "Interleukin–8—A mediator of inflammatory lung disease?" *Advances in Experimental Medicine and Biology* 305:119–126 (1991).

St. John et al., "ImmunologicTherapy for ARDS, Septic Shock, and Multiple–Organ Failure" *Chest* 103:932–943 (1993).

Sticherling et al., "Immunohistochemical studies on NAP–1/IL–8 in contact eczema and atopic dermatitis" *Arch. Dermatol. Res.* 284:82–85 (1992).

Sticherling et al., "Production and Characterization of Monoclonal Antibodies Against the Novel Neutrophil Activating Peptide NAP/IL–8" *J. Immunol.* 1435):1628–1634 (Sep. 1, 1989).

Teran, L.M. et al., "Neutrophil and eosinophil chemotaxins in asthma"*Quarterly Journal of Medicine* 86:761–769 (1993).

Virchow, Jr. et al., "T cells and cytokines in bronchoalveolar lavage fluid after segmental allerge n provocation in atopic asthma" *Am. J. Respiratory and Critical Care Medicine* 151(4):960–968 (1995).

Wada et al., "Prevention of proteinuria by the administration of anti–interleukin 8 antibody in experimental acute immune complex–induced glomerulonephritis" *Journal of Experimental Medicine* 180:1135–1140 (1994).

Waldman, Thomas A., "Monoclonal Antibodies in Diagnosis and Therapy" *Science* 252:1657–1662 (Jun. 21, 1991).

Walker, C. et al., "Activated T cells and cytokines in brochoalveolar lavages from patients with vraious lung diseases associated with eosinophilia" *Am. J. Respir. Crit. Care Med.* 150(4):1038–1048 (1994).

Wang, J.H. et al., "Effect of inhaled beclomethasone dipropionate on expression of proinflammatory cytokines and activated eosinphils in the bronchial epithelium of patients with mild asthma" *J. Allergy Clin. Immunol.* 94(6 Pt. 1):1025–1034 (1994).

Warringa et al., "Allergens, IgE, mediators, inflammatory mechanisms: Upregulation of formyl–peptide and interleukin–8–induced eosinophil chemotaxis in patients with allergic asthma interleukin–8–induced eosinophil chemotaxis in patients with allergic asthma" *J. Allergy Clin. Immunol.* 916):1198–1205 (1993).

Warringa et al., "Modulation of eosinophil chemotaxis by interleukin–5" *Am. J. respir. Cell Mol. Biol.* 7(6):631–636 (1992).

Xiu, Q et al., "Bronchial hyperresponsiveness and airway neutrophil accumulation induced by intereukin–8 and the effect of the thromboxane $A_2$ antagonist S–1452 in guinea–pigs" *Clin. Exp. Allergy* 25(1):51–59 (1995).

Yousefi et al., "IL–8 is expressed by human peripheral blood eosinophils" *J. Immunol.* 154(10):5481–5490 (1995).

Light Chain Primers:

MKLC-1, 22mer

5'    CAGTCCAACTGTTCAGGACGCC 3'          (SEQ ID NO:1)

MKLC-2, 22mer

5'    GTGCTGCTCATGCTGTAGGTGC 3'          (SEQ ID NO:2)

MKLC-3, 23mer

5'    GAAGTTGATGTCTTGTGAGTGGC    3'          (SEQ ID NO:3)

Heavy Chain Primers:

IGG2AC-1, 24mer

5'    GCATCCTAGAGTCACCGAGGAGCC    3'          (SEQ ID NO:4)

IGG2AC-2, 22mer

5'    CACTGGCTCAGGGAAATAACCC 3'          (SEQ ID NO:5)

IGG2AC-3, 22mer

5'    GGAGAGCTGGGAAGGTGTGCAC 3'          (SEQ ID NO:6)

FIG. 13

Light chain forward primer

SL001A-2  35 mer

```
5' ACAAACGCGTACGCT GACATCGTCATGACCCAGTC 3'    (SEQ ID NO:7)
                 T  T            T            (SEQ ID NO:8)
                                 A             (SEQ ID NO:9)
```

Light chain reverse primer

SL001B  37 mer

```
5' GCTCTTCGAATG GTGGGAAGATGGATACAGTTGGTGC 3'  (SEQ ID NO:10)
```

FIG. 14

Heavy chain forward primer

SL002B  39 mer

```
5' CGATGGGCCCGG ATAGACCGATGGGGCTGTTGTTTTGGC 3' (SEQ ID NO:11)
                T                C              (SEQ ID NO:12)
                G                                (SEQ ID NO:13)
                A                                (SEQ ID NO:14)
```

Heavy chain reverse primer

SL002B  39-MER

```
5' CGATGGGCCCGG ATAGACCGATGGGGCTGTTGTTTTGGC 3' (SEQ ID NO:15)
                T                                (SEQ ID NO:16)
                A                                (SEQ ID NO:17)
                G                                (SEQ ID NO:18)
```

FIG. 15

```
  1 GACATTGTCA TGACACAGTC TCAAAAATTC ATGTCCACAT CAGTAGGAGA CAGGGTCAGC
    CTGTAACAGT ACTGTGTCAG AGTTTTTAAG TACAGGTGTA GTCATCCTCT GTCCCAGTCG
  1 D  I  V  M  T  Q  S  Q  K  F  M  S  T  S  V  G  D  R  V  S

61 GTCACCTGCA AGGCCAGTCA GAATGTGGGT ACTAATGTAG CCTGGTATCA ACAGAAACCA
    CAGTGGACGT TCCGGTCAGT CTTACACCCA TGATTACATC GGACCATAGT TGTCTTTGGT
 21 V  T  C  K  A  S  Q  N  V  G  T  N  V  A  W  Y  Q  Q  K  P
                   ‾‾‾‾‾‾‾‾‾‾‾‾‾‾‾‾‾‾‾‾‾‾‾‾
                              CDR #1

121 GGGCAATCTC CTAAAGCACT GATTTACTCG TCATCCTACC GGTACAGTGG AGTCCCTGAT
    CCCGTTAGAG GATTTCGTGA CTAAATGAGC AGTAGGATGG CCATGTCACC TCAGGGACTA
 41 G  Q  S  P  K  A  L  I  Y  S  S  S  Y  R  Y  S  G  V  P  D
                            ‾‾‾‾‾‾‾‾‾‾
                              CDR #2

181 CGCTTCACAG GCAGTGGATC TGGGACAGAT TTCACTCTCA CCATCAGCCA TGTGCAGTCT
    GCGAAGTGTC CGTCACCTAG ACCCTGTCTA AAGTGAGAGT GGTAGTCGGT ACACGTCAGA
 61 R  F  T  G  S  G  S  G  T  D  F  T  L  T  I  S  H  V  Q  S

241 GAAGACTTGG CAGACTATTT CTGTCAGCAA TATAACATCT ATCCTCTCAC GTTCGGTCCT
    CTTCTGAACC GTCTGATAAA GACAGTCGTT ATATTGTAGA TAGGAGAGTG CAAGCCAGGA
 81 E  D  L  A  D  Y  F  C  Q  Q  Y  N  I  Y  P  L  T  F  G  P
                            ‾‾‾‾‾‾‾‾‾‾‾‾‾‾‾‾‾‾‾
                              CDR #3

301 GGGACCAAGC TGGAGTTGAA ACGGGCTGAT GCTGCACCAC CAACTGTATC CATCTTCCCA
    CCCTGGTTCG ACCTCAACTT TGCCCGACTA CGACGTGGTG GTTGACATAG GTAGAAGGGT
101 G  T  K  L  E  L  K  R  D  A  A  P  P  T  V  S  I  F  P

BstBI
361 CCATTCGAA           (SEQ ID NO:19)
    GGTAAGCTT
121 P  F  E             (SEQ ID NO:20)
```

FIG. 16

```
  1 TTCTATTGCT ACAAACGCGT ACGCTGAGGT GCAGCTGGTG GAGTCTGGGG GAGGCTTAGT
    AAGATAACGA TGTTTGCGCA TGCGACTCCA CGTCGACCAC CTCAGACCCC CTCCGAATCA
  1                                  E  V  Q  L  V  E  S  G  G  G  L  V

61 GCCGCCTGGA GGGTCCCTGA AACTCTCCTG TGCAGCCTCT GGATTCATAT TCAGTAGTTA
    CGGCGGACCT CCCAGGGACT TTGAGAGGAC ACGTCGGAGA CCTAAGTATA AGTCATCAAT
 13  P  P  G  G  S  L  K  L  S  C  A  A  S  G  F  I  F  S  S  Y
                                                 ‾‾‾‾‾‾‾‾‾‾‾‾‾‾
                                                       *  *
                                                 CDR #1

121 TGGCATGTCT TGGGTTCGCC AGACTCCAGG CAAGAGCCTG GAGTTGGTCG CAACCATTAA
    ACCGTACAGA ACCCAAGCGG TCTGAGGTCC GTTCTCGGAC CTCAACCAGC GTTGGTAATT
 33  G  M  S  W  V  R  Q  T  P  G  K  S  L  E  L  V  A  T  I  N
     *  *  *                                            *  *  *

181 TAATAATGGT GATAGCACCT ATTATCCAGA CAGTGTGAAG GGCCGATTCA CCATCTCCCG
    ATTATTACCA CTATCGTGGA TAATAGGTCT GTCACACTTC CCGGCTAAGT GGTAGAGGGC
 53  N  N  G  D  S  T  Y  Y  P  D  S  V  K  G  R  F  T  I  S  R
    ‾‾‾‾‾‾‾‾‾‾‾‾‾
     *  *  *  *  *  *  *  *  *  *  *  *
             CDR #2

241 AGACAATGCC AAGAACACCC TGTACCTGCA AATGAGCAGT CTGAAGTCTG AGGACACAGC
    TCTGTTACGG TTCTTGTGGG ACATGGACGT TTACTCGTCA GACTTCAGAC TCCTGTGTCG
 73  D  N  A  K  N  T  L  Y  L  Q  M  S  S  L  K  S  E  D  T  A

301 CATGTTTTAC TGTGCAAGAG CCCTCATTAG TTCGGCTACT TGGTTTGGTT ACTGGGGCCA
    GTACAAAATG ACACGTTCTC GGGAGTAATC AAGCCGATGA ACCAAACCAA TGACCCCGGT
 93  M  F  Y  C  A  R  A  L  I  S  S  A  T  W  F  G  Y  W  G  Q
                         ‾‾‾‾‾‾‾‾‾‾‾‾‾‾‾‾‾‾‾‾‾‾‾‾‾‾‾
                         *  *  *  *  *  *  *  *  *  *
                             CDR #3

361 AGGGACTCTG GTCACTGTCT CTGCAGCCAA AACAACAGCC CCATCTGTCT
    TCCCTGAGAC CAGTGACAGA GACGTCGGTT TTGTTGTCGG GGTAGACAGA
113  G  T  L  V  T  V  S  A  A  K  T  T  A  P  S  V  Y

ApaI
411        ATCCGGG              (SEQ ID NO:21)
           TAGGCCC
130           P                 (SEQ ID NO:22)
```

FIG. 17

VL.front     31-MER

5' ACAAACGCGTACGCTGATATCGTCATGACAG   3'    (SEQ ID NO:23)

VL.rear 31-MER

5' GCAGCATCAGCTCTTCGAAGCTCCAGCTTGG   3'    (SEQ ID NO:24)

VH.front.SPE    21-MER

5' CCACTAGTACGCAAGTTCACG             3'    (SEQ ID NO:25)

VH.rear 33-MER

5' GATGGGCCCTTGGTGGAGGCTGCAGAGACAGTG  3'   (SEQ ID NO:26)

FIG. 18

```
  1 ATGAAGAAGA ATATCGCATT TCTTCTTGCA TCTATGTTCG TTTTTTCTAT TGCTACAAAC
    TACTTCTTCT TATAGCGTAA AGAAGAACGT AGATACAAGC AAAAAAGATA ACGATGTTTG
-23 M  K  K  N    I  A  F    L  L  A    S  M  F    V  F  S    I  A  T  N

61 GCGTACGCTG ATATCGTCAT GACACAGTCT CAAAAATTCA TGTCCACATC AGTAGGAGAC
    CGCATGCGAC TATAGCAGTA CTGTGTCAGA GTTTTTAAGT ACAGGTGTAG TCATCCTCTG
 -3 A  Y  A    D  I  V  M    T  Q  S    Q  K  F  M    S  T  S    V  G  D

121 AGGGTCAGCG TCACCTGCAA GGCCAGTCAG AATGTGGGTA CTAATGTAGC CTGGTATCAA
    TCCCAGTCGC AGTGGACGTT CCGGTCAGTC TTACACCCAT GATTACATCG GACCATAGTT
 18 R  V  S    V  T  C  K    A  S  Q  N  V  G  T  N  V  A    W  Y  Q
                              *  *  *  *  *  *  *  *  *  *  *
                                        CDR #1

181 CAGAAACCAG GGCAATCTCC TAAAGCACTG ATTTACTCGT CATCCTACCG GTACAGTGGA
    GTCTTTGGTC CCGTTAGAGG ATTTCGTGAC TAAATGAGCA GTAGGATGGC CATGTCACCT
 38 Q  K  P    G  Q  S  P    K  A  L    I  Y  S  S  S  Y  R    Y  S  G
                                           *  *  *  *  *  *  *
                                                 CDR #2

241 GTCCCTGATC GCTTCACAGG CAGTGGATCT GGGACAGATT TCACTCTCAC CATCAGCCAT
    CAGGGACTAG CGAAGTGTCC GTCACCTAGA CCCTGTCTAA AGTGAGAGTG GTAGTCGGTA
 58 V  P  D    R  F  T  G    S  G  S    G  T  D  F    T  L  T    I  S  H

301 GTGCAGTCTG AAGACTTGGC AGACTATTTC TGTCAGCAAT ATAACATCTA TCCTCTCACG
    CACGTCAGAC TTCTGAACCG TCTGATAAAG ACAGTCGTTA TATTGTAGAT AGGAGAGTGC
 78 V  Q  S    E  D  L  A    D  Y  F    C  Q  Q  Y  N  I  Y  P  L  T
                                              *  *  *  *  *  *  *  *  *
                                                          CDR #3
                     BstBI
361 TTCGGTCCTG GGACCAAGCT GGAGCTTCGA AGAGCTGTGG CTGCACCATC TGTCTTCATC
    AAGCCAGGAC CCTGGTTCGA CCTCGAAGCT TCTCGACACC GACGTGGTAG ACAGAAGTAG
 98 F  G  P    G  T  K  L    E  L  R    R  A  V    A  P  S    V  F  I

421 TTCCCGCCAT CTGATGAGCA GTTGAAATCT GGAACTGCTT CTGTTGTGTG CCTGCTGAAT
    AAGGGCGGTA GACTACTCGT CAACTTTAGA CCTTGACGAA GACAACACAC GGACGACTTA
118 F  P  P    S  D  E  Q    L  K  S    G  T  A  S    V  V  C    L  L  N

481 AACTTCTATC CCAGAGAGGC CAAAGTACAG TGGAAGGTGG ATAACGCCCT CCAATCGGGT
    TTGAAGATAG GGTCTCTCCG GTTTCATGTC ACCTTCCACC TATTGCGGGA GGTTAGCCCA
138 N  F  Y    P  R  E  A    K  V  Q    W  K  V  D    N  A  L    Q  S  G

541 AACTCCCAGG AGAGTGTCAC AGAGCAGGAC AGCAAGGACA GCACCTACAG CCTCAGCAGC
    TTGAGGGTCC TCTCACAGTG TCTCGTCCTG TCGTTCCTGT CGTGGATGTC GGAGTCGTCG
158 N  S  Q    E  S  V  T    E  Q  D    S  K  D  S    T  Y  S    L  S  S

601 ACCCTGACGC TGAGCAAAGC AGACTACGAG AAACACAAAG TCTACGCCTG CGAAGTCACC
    TGGGACTGCG ACTCGTTTCG TCTGATGCTC TTTGTGTTTC AGATGCGGAC GCTTCAGTGG
178 T  L  T    L  S  K  A    D  Y  E    K  H  K  V    Y  A  C    E  V  T

661 CATCAGGGCC TGAGCTCGCC CGTCACAAAG AGCTTCAACA GGGGAGAGTG
    GTAGTCCCGG ACTCGAGCGG GCAGTGTTTC TCGAAGTTGT CCCCTCTCAC
198 H  Q  G    L  S  S  P    V  T  K    S  F  N  R    G  E  C

711     TTAA          (SEQ ID NO:27)
        AATT
216      O            (SEQ ID NO:28)
```

FIG. 19

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K  N    I  A  F    L  L  A    S  M  F  V    F  S  I    A  T  N

61 GCGTACGCTG AGGTGCAGCT GGTGGAGTCT GGGGGAGGCT TAGTGCCGCC TGGAGGGTCC
    CGCATGCGAC TCCACGTCGA CCACCTCAGA CCCCCTCCGA ATCACGGCGG ACCTCCCAGG
 -3 A  Y  A  E    V  Q  L    V  E  S    G  G  G  L    V  P  P    G  G  S

121 CTGAAACTCT CCTGTGCAGC CTCTGGATTC ATATTCAGTA GTTATGGCAT GTCTTGGGTT
    GACTTTGAGA GGACACGTCG GAGACCTAAG TATAAGTCAT CAATACCGTA CAGAACCCAA
 18 L  K  L  S    C  A  A    S  G  F    I  F  S  S    Y  G  M    S  W  V
                                        —  —  —  —    —  —  —
                                                CDR #1
                                                            *  *  *

181 CGCCAGACTC CAGGCAAGAG CCTGGAGTTG GTCGCAACCA TTAATAATAA TGGTGATAGC
    GCGGTCTGAG GTCCGTTCTC GGACCTCAAC CAGCGTTGGT AATTATTATT ACCACTATCG
 38 R  Q  T  P    G  K  S    L  E  L    V  A  T  I    N  N  N    G  D  S
                                                      *  —  —    —  —  —
                                                      *  *  *  *  *  *  *

241 ACCTATTATC CAGACAGTGT GAAGGGCCGA TTCACCATCT CCCGAGACAA TGCCAAGAAC
    TGGATAATAG GTCTGTCACA CTTCCCGGCT AAGTGGTAGA GGGCTCTGTT ACGGTTCTTG
 58 T  Y  Y  P    D  S  V    K  G  R    F  T  I  S    R  D  N    A  K  N
    *  *  *  *    *  *  *    *
            CDR #2

301 ACCCTGTACC TGCAAATGAG CAGTCTGAAG TCTGAGGACA CAGCCATGTT TTACTGTGCA
    TGGGACATGG ACGTTTACTC GTCAGACTTC AGACTCCTGT GTCGGTACAA AATGACACGT
 78 T  L  Y  L    Q  M  S    S  L  K    S  E  D  T    A  M  F    Y  C  A

361 AGAGCCCTCA TTAGTTCGGC TACTTGGTTT GGTTACTGGG GCCAAGGGAC TCTGGTCACT
    TCTCGGGAGT AATCAAGCCG ATGAACCAAA CCAATGACCC CGGTTCCCTG AGACCAGTGA
 98 R  A  L  I    S  S  A    T  W  F    G  Y  W    G  Q  G  T    L  V  T
          —  —   —  —  —    —  —  —
    *  *  *  *   *  *  *  *  *  *  *
              CDR #3
              ApaI
421 GTCTCTGCAG CCTCCACCAA GGGCCCATCG GTCTTCCCCC TGGCACCCTC CTCCAAGAGC
    CAGAGACGTC GGAGGTGGTT CCCGGGTAGC CAGAAGGGGG ACCGTGGGAG GAGGTTCTCG
118 V  S  A  A    S  T  K    G  P  S    V  F  P  L    A  P  S    S  K  S

481 ACCTCTGGGG GCACAGCGGC CCTGGGCTGC CTGGTCAAGG ACTACTTCCC CGAACCGGTG
    TGGAGACCCC CGTGTCGCCG GGACCCGACG GACCAGTTCC TGATGAAGGG GCTTGGCCAC
138 T  S  G  G    T  A  A    L  G  C    L  V  K  D    Y  F  P    E  P  V

541 ACGGTGTCGT GGAACTCAGG CGCCCTGACC AGCGGCGTGC ACACCTTCCC GGCTGTCCTA
    TGCCACAGCA CCTTGAGTCC GCGGGACTGG TCGCCGCACG TGTGGAAGGG CCGACAGGAT
158 T  V  S  W    N  S  G    A  L  T    S  G  V  H    T  F  P    A  V  L

601 CAGTCCTCAG GACTCTACTC CCTCAGCAGC GTGGTGACCG TGCCCTCCAG CAGCTTGGGC
    GTCAGGAGTC CTGAGATGAG GGAGTCGTCG CACCACTGGC ACGGGAGGTC GTCGAACCCG
178 Q  S  S  G    L  Y  S    L  S  S    V  V  T  V    P  S  S    S  L  G

661 ACCCAGACCT ACATCTGCAA CGTGAATCAC AAGCCCAGCA ACACCAAGGT GGACAAGAAA
    TGGGTCTGGA TGTAGACGTT GCACTTAGTG TTCGGGTCGT TGTGGTTCCA CCTGTTCTTT
198 T  Q  T  Y    I  C  N    V  N  H    K  P  S  N    T  K  V    D  K  K

721 GTTGAGCCCA AATCTTGTGA CAAAACTCAC ACATGA        (SEQ ID NO:29)
    CAACTCGGGT TTAGAACACT GTTTTGAGTG TGTACT
218 V  E  P  K    S  C  D    K  T  H    T  O       (SEQ ID NO:30)
```

FIG. 20

Light Chain Primers:

MKLC-1, 22mer

5'      CAGTCCAACTGTTCAGGACGCC 3'          (SEQ ID NO:31)

MKLC-2, 22mer

5'      GTGCTGCTCATGCTGTAGGTGC 3'          (SEQ ID NO:32)

MKLC-3, 23mer

5'      GAAGTTGATGTCTTGTGAGTGGC      3'      (SEQ ID NO:33)

Heavy Chain Primers:

IGG2AC-1, 24mer

5'      GCATCCTAGAGTCACCGAGGAGCC      3'      (SEQ ID NO:34)

IGG2AC-2, 22mer

5'      CACTGGCTCAGGGAAATAACCC 3'          (SEQ ID NO:35)

IGG2AC-3, 22mer

5'      GGAGAGCTGGGAAGGTGTGCAC 3'          (SEQ ID NO:36)

FIG. 21

Light chain forward primer

6G4.light.Nsi  36-MER

```
5' CCAATGCATACGCT GAC ATC GTG ATG ACC CAG ACC CC  3' (SEQ ID NO:37)
                  T   T          T       T        (SEQ ID NO:38)
                                 A       A        (SEQ ID NO:39)
```

Light chain reverse primer

6G4.light.Mun  35-MER

```
5' AGA TGT CAA TTG CTC ACT GGA TGG TGG GAA GAT GG 3' (SEQ ID NO:40)
```

FIG. 22

Heavy chain forward primer

6G4.heavy.Mlu  32-MER

```
5' CAAACGCGTACGCT GAG ATC CAG CTG CAG CAG  3'  (SEQ ID NO:41)
                   T       C                   (SEQ ID NO:42)
```

Heavy chain reverse primer

SL002B  39-MER

```
5' CGATGGGCCCGG ATAGACCGATGGGGCTGTTGTTTTGGC  3' (SEQ ID NO:43)
                T                               (SEQ ID NO:44)
                A                               (SEQ ID NO:45)
                G                               (SEQ ID NO:46)
```

FIG. 23

```
 70 G ATATCGTGAT GACACAGACA CCACTCTCCC TGCCTGTCAG TCTTGGAGAT
    C TATAGCACTA CTGTGTCTGT GGTGAGAGGG ACGGACAGTC AGAACCTCTA
  1 D   I   V   M   T   Q   T   P   L   S   L   P   V   S   L   G   D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18 Q   A   S   I   S   C   R   S   S Q   S   L   V   H   G   I   G   N   T   Y
                                      *  *   *   *   *   *   *   *   *   *   *   *   *   *
                                                    CDR #1

181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38 L   H   W   Y   L   Q   K   P   G   Q   S   P   K   L   L   I   Y   K   V   S
    *   *                                                                *   *   *
                                                                          CDR #2

241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58 N   R   F   S   G   V   P   D   R   F   S   G   S   G   S   G   T   D   F   T
    *   *   *   *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78 L   R   I   S   R   V   E   A   E   D   L   G   L   Y   F   C   S   Q S   T
                                                                        *   *   *
                                                                         CDR #3

361 CATGTTCCGC TCACGTTCGG TGCTGGGACC AAGCTGGAGC TGAAACGGGC TGATGCTGCA
    GTACAAGGCG AGTGCAAGCC ACGACCCTGG TTCGACCTCG ACTTTGCCCG ACTACGACGT
 98 H V P L   T   F   G   A   G   T   K   L   E   L   K   R   A   D   A   A
    *   *   *   *   *
                                                      MunI
421 CCAACTGTAT CCATCTTCCC ACCATCCAGT GAGCAATTGA      (SEQ ID NO:47)
    GGTTGACATA GGTAGAAGGG TGGTAGGTCA CTCGTTAACT
118 P   T   V   S   I   F   P   P   S   S   E   Q   L   K      (SEQ ID NO:48)
```

FIG. 24

```
 70 G AGATTCAGCT GCAGCAGTCT GGACCTGAGC TGATGAAGCC TGGGGCTTCA
   C TCTAAGTCGA CGTCGTCAGA CCTGGACTCG ACTACTTCGG ACCCCGAAGT
  1 E   I   Q   L   Q   Q   S   G   P   E   L   M   K   P   G   A   S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V   K   I   S   C   K   A   S   G   Y   S   F   S   S   H   Y   M   H   W   V
                                        *   *   *   *   *
                                            CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K   Q   S   H   G   K   S   L   E   W   I   G   Y   I   D   P   S   N   G   E
                                                *   *   *   *   *   *   *   *
                                                        CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T   T   Y   N   Q   K   F   K   G   K   A   T   L   T   V   D   T   S   S   S
    *   *   *   *   *   *   *   *   *

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T   A   N   V   H   L   S   S   L   T   S   D   D   S   A   V   Y   F   C   A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R   G   D   Y   R   Y   N   G   D   W   F   F   D   V   W   G   A   G   T   T
            *   *   *   *   *   *   *   *   *   *   *
                    CDR #3
    BstEII                                                          ApaI
421 GTCACCGTCT CCTCCGCCAA AACCGACAGC CCCATCGGTC TATCCGGGCC
    CAGTGGCAGA GGAGGCGGTT TTGGCTGTCG GGGTAGCCAG ATAGGCCCGG
118 V   T   V   S   S   A   K   T   D   S   P   I   G   L   S   G   P

471 CATC       (SEQ ID NO:49)
    GTAG
135 I          (SEQ ID NO:50)
```

FIG. 25

5' CTTGGTGGAGGCGGAGGAGACG 3'         (SEQ ID NO:51)

Mutagenesis Primer for 6G425VL

DS/VF  38MER

5' GAAACGGGCTGTTGCTGCACCAACTGTATTCATCTTCC 3'    (SEQ ID NO:52)

SYN.BstEII  31 MER

5' GTCACCGTCT CCTCCGCCTC CACCAAGGGC C 3'    (SEQ ID NO:53)

SYN.Apa  22 MER

5' CTTGGTGGAGGCGGAGGAGACG   3'         (SEQ ID NO:54)

FIG. 26

```
  1 ATGAAGAAGA ATATCGCATT TCTTCTTGCA TCTATGTTCG TTTTTTCTAT TGCTACAAAT
    TACTTCTTCT TATAGCGTAA AGAAGAACGT AGATACAAGC AAAAAAGATA ACGATGTTTA
-23 M  K  K  N  I  A  F  L  L  A  S  M  F  V  F  S  I  A  T  N

61 GCATACGCTG ATATCGTGAT GACACAGACA CCACTCTCCC TGCCTGTCAG TCTTGGAGAT
    CGTATGCGAC TATAGCACTA CTGTGTCTGT GGTGAGAGGG ACGGACAGTC AGAACCTCTA
 -3 A  Y  A  D  I  V  M  T  Q  T  P  L  S  L  P  V  S  L  G  D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18 Q  A  S  I  S  C  R  S  S  Q  S  L  V  H  G  I  G  N  T  Y
                              *  *  *  *  *  *  *  *  *  *  *  *  *
                                           CDR #1

181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38 L  H  W  Y  L  Q  K  P  G  Q  S  P  K  L  I  Y  K  V  S
    *  *                                                *  *  *
                                                      CDR #2

241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58 N  R  F  S  G  V  P  D  R  F  S  G  S  G  S  G  T  D  F  T
    *  *  *  *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78 L  R  I  S  R  V  E  A  E  D  L  G  L  Y  F  C  S  Q  S  T
                                                         *  *  *
                                                         CDR #3

361 CATGTTCCGC TCACGTTCGG TGCTGGGACC AAGCTGGAGC TGAAACGGGC TGTTGCTGCA
    GTACAAGGCG AGTGCAAGCC ACGACCCTGG TTCGACCTCG ACTTTGCCCG ACAACGACGT
 96 H  V  P  L  T  F  G  A  G  T  K  L  E  L  K  R  A  V  A  A
    *  *  *  *  *

421 CCAACTGTAT TCATCTTCCC ACCATCCAGT GAGCAATTGA AATCTGGAAC TGCCTCTGTT
    GGTTGACATA AGTAGAAGGG TGGTAGGTCA CTCGTTAACT TTAGACCTTG ACGGAGACAA
118 P  T  V  F  I  F  P  P  S  S  E  Q  L  K  S  G  T  A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L  L  N  N  F  Y  P  R  E  A  K  V  Q  W  K  V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q  S  G  N  S  Q  E  S  V  T  E  Q  D  S  K  D  S  T

601 TACAGCCTCA GCAGCACCCT GACGCTGAGC AAAAGCAGAC TACGAGAAACA CAAAGTCTAC
    ATGTCGGAGT CGTCGTGGGA CTGCGACTCG TTTCGTCTGA TGCTCTTTGT GTTTCAGATG
178 Y  S  L  S  S  T  L  T  L  S  K  A  D  Y  E  K  H  K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E  V  T  H  Q  G  L  S  S  P  V  T  K  S  F  N  R  G

721 GAGTGTTAA    (SEQ ID NO:55)
    CTCACAATT
218 E  C  O    (SEQ ID NO:56)
```

FIG. 27

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K   I  A  F    L  L  A    S  M  F    V  F  S  I  A  T  N

61 GCGTACGCTG AGATTCAGCT GCAGCAGTCT GGACCTGAGC TGATGAAGCC TGGGGCTTCA
    CGCATGCGAC TCTAAGTCGA CGTCGTCAGA CCTGGACTCG ACTACTTCGG ACCCCGAAGT
 -3 A  Y  A  E  I  Q  L  Q  Q  S    G  P  E  L  M  K  P   G  A  S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V  K  I  S  C  K  A  S  G  Y   S  F  S  S  H  Y  M   H  W  V
                           -  -  -  -  -  -  -  -
                                     CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K  Q  S  H  G  K  S  L  E  W   I  G  Y  I  D  P  S   N  G  E
                                              -  -  -  -  -  -
                                                  CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T  T  Y  N  Q  K  F  K  G  K   A  T  L  T  V  D  T   S  S  S
    -  -  -  -  -  -  -

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T  A  N  V  H  L  S  S  L  T   S  D  D  S  A  V  Y   F  C  A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R  G  D  Y  R  Y  N  G  D  W   F  F  D  V  W  G  A   G  T  T
          -  -  -  -  -  -  -  -  -  -  -  -
                  CDR #3

421 GTCACCGTCT CCTCCGCCTC CACCAAGGGC CCATCGGTCT TCCCCCTGGC ACCCTCCTCC
    CAGTGGCAGA GGAGGCGGAG GTGGTTCCCG GGTAGCCAGA AGGGGGACCG TGGGAGGAGG
118 V  T  V  S  S  A  S  T  K  G   P  S  V  F  P  L  A   P  S  S

481 AAGAGCACCT CTGGGGGCAC AGCGGCCCTG GGCTGCCTGG TCAAGGACTA CTTCCCCGAA
    TTCTCGTGGA GACCCCCGTG TCGCCGGGAC CCGACGGACC AGTTCCTGAT GAAGGGGCTT
138 K  S  T  S  G  G  T  A  A  L   G  C  L  V  K  D  Y   F  P  E

541 CCGGTGACGG TGTCGTGGAA CTCAGGCGCC CTGACCAGCG GCGTGCACAC CTTCCCGGCT
    GGCCACTGCC ACAGCACCTT GAGTCCGCGG GACTGGTCGC CGCACGTGTG GAAGGGCCGA
158 P  V  T  V  S  W  N  S  G  A   L  T  S  G  V  H  T   F  P  A

601 GTCCTACAGT CCTCAGGACT CTACTCCCTC AGCAGCGTGG TGACCGTGCC CTCCAGCAGC
    CAGGATGTCA GGAGTCCTGA GATGAGGGAG TCGTCGCACC ACTGGCACGG GAGGTCGTCG
178 V  L  Q  S  S  G  L  Y  S  L   S  S  V  V  T  V  P   S  S  S

661 TTGGGCACCC AGACCTACAT CTGCAACGTG AATCACAAGC CCAGCAACAC CAAGGTGGAC
    AACCCGTGGG TCTGGATGTA GACGTTGCAC TTAGTGTTCG GGTCGTTGTG GTTCCACCTG
198 L  G  T  Q  T  Y  I  C  N  V   N  H  K  P  S  N  T   K  V  D

721 AAGAAAGTTG AGCCCAAATC TTGTGACAAA ACTCACACAT GA            (SEQ ID NO:57)
    TTCTTTCAAC TCGGGTTTAG AACACTGTTT TGAGTGTGTA CT
218 K  K  V  E  P  K  S  C  D  K   T  H  T  O              (SEQ ID NO:58)
```

FIG. 28 mouse #823 grp4 not included (BAL cells smudged)
mouse #780 not included (kidney clst)
mouse #833 grp3 included (no ova-IgE)
mouse #821 grp2 not included (clot in CBC)

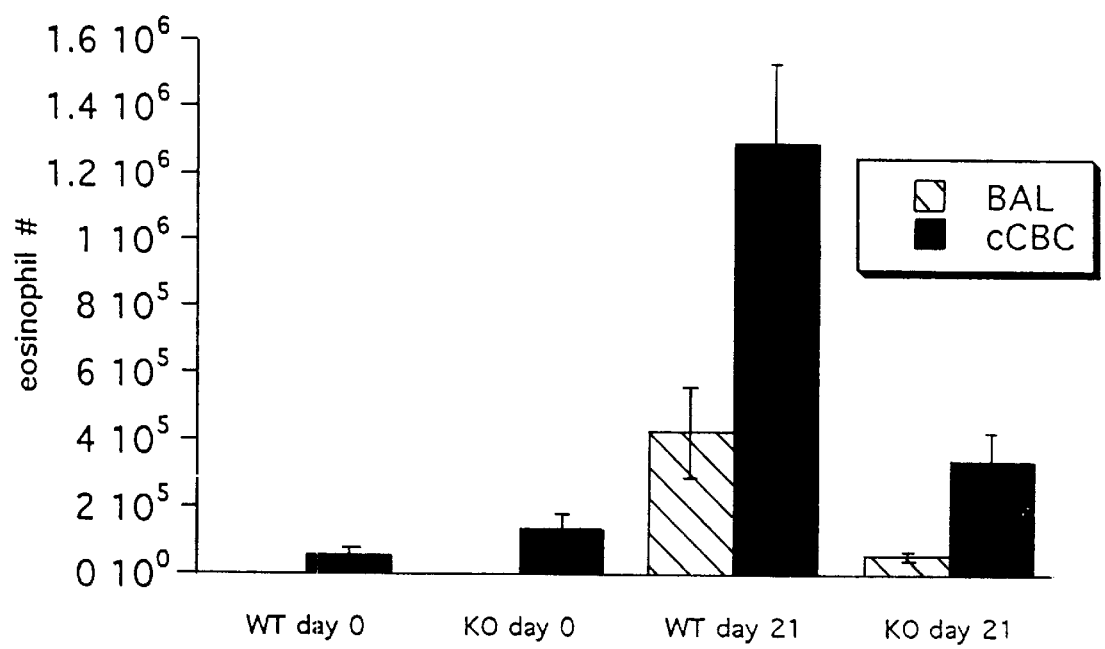
FIG. 31
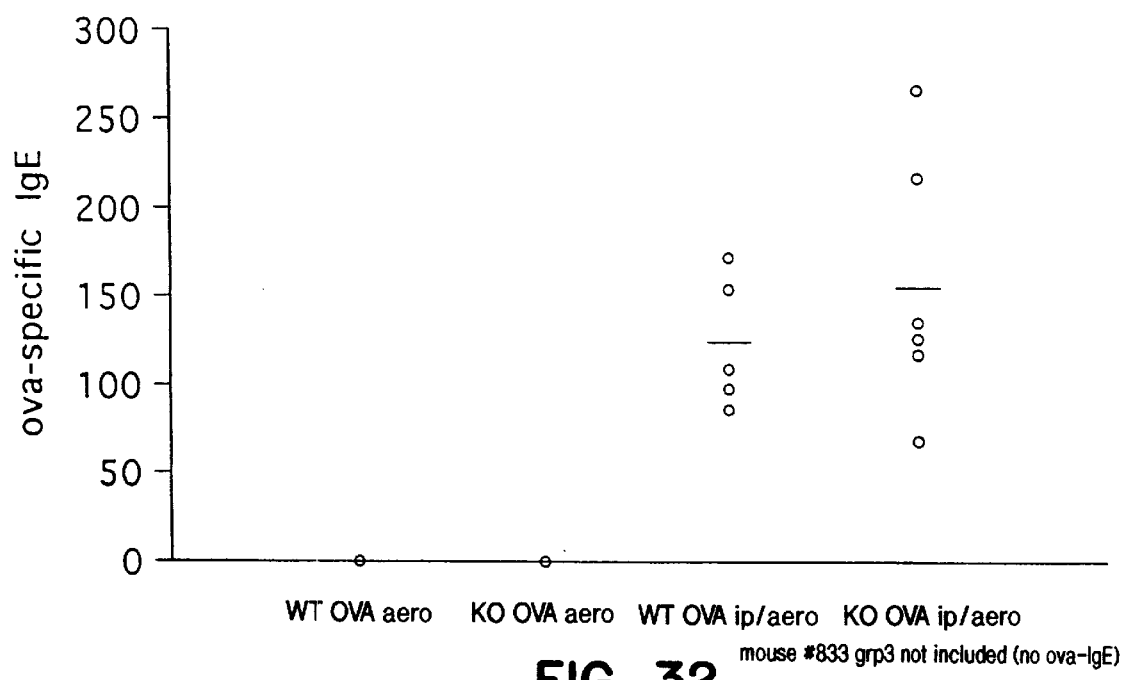
FIG. 32  mouse #833 grp3 not included (no ova-IgE)

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
        ( A ) LENGTH: 22 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:1:

CAGTCCAACT GTTCAGGACG CC        22

( 2 ) INFORMATION FOR SEQ ID NO:2:

( i ) SEQUENCE CHARACTERISTICS:
        ( A ) LENGTH: 22 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:2:

GTGCTGCTCA TGCTGTAGGT GC        22

( 2 ) INFORMATION FOR SEQ ID NO:3:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:3:

GAAGTTGATG TCTTGTGAGT GGC        23

( 2 ) INFORMATION FOR SEQ ID NO:4:

( i ) SEQUENCE CHARACTERISTICS:
        ( A ) LENGTH: 24 base pairs
        ( B ) TYPE: Nucleic Acid
        ( C ) STRANDEDNESS: Single (D) TOPOLOGY: Linear (xi) SEQUENCE DESCRIPTION: SEQ ID NO:4:

GCATCCTAGA GTCACCGAGG AGCC                                                24

(2) INFORMATION FOR SEQ ID NO:5:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:5:

CACTGGCTCA GGGAAATAAC CC                                                  22

(2) INFORMATION FOR SEQ ID NO:6:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:6:

GGAGAGCTGG GAAGGTGTGC AC                                                  22

(2) INFORMATION FOR SEQ ID NO:7:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:7:

ACAAACGCGT ACGCTGACAT CGTCATGACC CAGTC                                    35

(2) INFORMATION FOR SEQ ID NO:8:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:8:

ACAAACGCGT ACGCTGATAT TGTCATGACT CAGTC                                    35

(2) INFORMATION FOR SEQ ID NO:9:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:9:

ACAAACGCGT ACGCTGACAT CGTCATGACA CAGTC                                    35

(2) INFORMATION FOR SEQ ID NO:10:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (x i) SEQUENCE DESCRIPTION: SEQ ID NO:10:

GCTCTTCGAA TGGTGGGAAG ATGGATACAG TTGGTGC    37

(2) INFORMATION FOR SEQ ID NO:11:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (x i) SEQUENCE DESCRIPTION: SEQ ID NO:11:

CGATGGGCCC GGATAGACCG ATGGGGCTGT TGTTTTGGC    39

(2) INFORMATION FOR SEQ ID NO:12:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (x i) SEQUENCE DESCRIPTION: SEQ ID NO:12:

CGATGGGCCC GGATAGACTG ATGGGGCTGT CGTTTTGGC    39

(2) INFORMATION FOR SEQ ID NO:13:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (x i) SEQUENCE DESCRIPTION: SEQ ID NO:13:

CGATGGGCCC GGATAGACGG ATGGGGCTGT TGTTTTGGC    39

(2) INFORMATION FOR SEQ ID NO:14:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (x i) SEQUENCE DESCRIPTION: SEQ ID NO:14:

CGATGGGCCC GGATAGACAG ATGGGGCTGT TGTTTTGGC    39

(2) INFORMATION FOR SEQ ID NO:15:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (x i) SEQUENCE DESCRIPTION: SEQ ID NO:15:

CGATGGGCCC GGATAGACCG ATGGGGCTGT TGTTTTGGC    39

(2) INFORMATION FOR SEQ ID NO:16:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (x i) SEQUENCE DESCRIPTION: SEQ ID NO:16:

CGATGGGCCC GGATAGACTG ATGGGGCTGT TGTTTTGGC                                   39

( 2 ) INFORMATION FOR SEQ ID NO:17:

( i ) SEQUENCE CHARACTERISTICS:
        ( A ) LENGTH: 39 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:17:

CGATGGGCCC GGATAGACAG ATGGGGCTGT TGTTTTGGC                                   39

( 2 ) INFORMATION FOR SEQ ID NO:18:

( i ) SEQUENCE CHARACTERISTICS:
        ( A ) LENGTH: 39 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:18:

CGATGGGCCC GGATAGACGG ATGGGGCTGT TGTTTTGGC                                   39

( 2 ) INFORMATION FOR SEQ ID NO:19:

( i ) SEQUENCE CHARACTERISTICS:
        ( A ) LENGTH: 369 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:19:

GACATTGTCA TGACACAGTC TCAAAAATTC ATGTCCACAT CAGTAGGAGA                        50

CAGGGTCAGC GTCACCTGCA AGGCCAGTCA GAATGTGGGT ACTAATGTAG                       100

CCTGGTATCA ACAGAAACCA GGGCAATCTC CTAAAGCACT GATTTACTCG                       150

TCATCCTACC GGTACAGTGG AGTCCCTGAT CGCTTCACAG GCAGTGGATC                       200

TGGGACAGAT TTCACTCTCA CCATCAGCCA TGTGCAGTCT GAAGACTTGG                       250

CAGACTATTT CTGTCAGCAA TATAACATCT ATCCTCTCAC GTTCGGTCCT                       300

GGGACCAAGC TGGAGTTGAA ACGGGCTGAT GCTGCACCAC CAACTGTATC                       350

CATCTTCCCA CCATTCGAA                                                        369

( 2 ) INFORMATION FOR SEQ ID NO:20:

( i ) SEQUENCE CHARACTERISTICS:
        ( A ) LENGTH: 123 amino acids
        ( B ) TYPE: Amino Acid
        ( D ) TOPOLOGY: Linear ( x i ) SEQUENCE DESCRIPTION: SEQ ID NO:20:

```
Asp  Ile  Val  Met  Thr  Gln  Ser  Gln  Lys  Phe  Met  Ser  Thr  Ser  Val
 1                    5                   10                        15

Gly  Asp  Arg  Val  Ser  Val  Thr  Cys  Lys  Ala  Ser  Gln  Asn  Val  Gly
                     20                   25                        30

Thr  Asn  Val  Ala  Trp  Tyr  Gln  Gln  Lys  Pro  Gly  Gln  Ser  Pro  Lys
                     35                   40                        45

Ala  Leu  Ile  Tyr  Ser  Ser  Ser  Tyr  Arg  Tyr  Ser  Gly  Val  Pro  Asp
                     50                   55                        60

Arg  Phe  Thr  Gly  Ser  Gly  Ser  Gly  Thr  Asp  Phe  Thr  Leu  Thr  Ile
                     65                   70                        75
```

| Ser | His | Val | Gln | Ser<br>80 | Glu | Asp | Leu | Ala | Asp<br>85 | Tyr | Phe | Cys | Gln | Gln<br>90 |
|---|---|---|---|---|---|---|---|---|---|---|---|---|---|---|
| Tyr | Asn | Ile | Tyr | Pro<br>95 | Leu | Thr | Phe | Gly | Pro<br>100 | Gly | Thr | Lys | Leu | Glu<br>105 |
| Leu | Lys | Arg | Ala | Asp<br>110 | Ala | Ala | Pro | Pro | Thr<br>115 | Val | Ser | Ile | Phe | Pro<br>120 |
| Pro | Phe | Glu<br>123 | | | | | | | | | | | | |

( 2 ) INFORMATION FOR SEQ ID NO:21:

( i ) SEQUENCE CHARACTERISTICS:
        ( A ) LENGTH: 417 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:21:

| | | | | | |
|---|---|---|---|---|---|
| TTCTATTGCT | ACAAACGCGT | ACGCTGAGGT | GCAGCTGGTG | GAGTCTGGGG | 50 |
| GAGGCTTAGT | GCCGCCTGGA | GGGTCCCTGA | AACTCTCCTG | TGCAGCCTCT | 100 |
| GGATTCATAT | TCAGTAGTTA | TGGCATGTCT | TGGGTTCGCC | AGACTCCAGG | 150 |
| CAAGAGCCTG | GAGTTGGTCG | CAACCATTAA | TAATAATGGT | GATAGCACCT | 200 |
| ATTATCCAGA | CAGTGTGAAG | GGCCGATTCA | CCATCTCCCG | AGACAATGCC | 250 |
| AAGAACACCC | TGTACCTGCA | AATGAGCAGT | CTGAAGTCTG | AGGACACAGC | 300 |
| CATGTTTTAC | TGTGCAAGAG | CCCTCATTAG | TTCGGCTACT | TGGTTTGGTT | 350 |
| ACTGGGGCCA | AGGGACTCTG | GTCACTGTCT | CTGCAGCCAA | AACAACAGCC | 400 |
| CCATCTGTCT | ATCCGGG | | | | 417 |

( 2 ) INFORMATION FOR SEQ ID NO:22:

( i ) SEQUENCE CHARACTERISTICS:
        ( A ) LENGTH: 130 amino acids
        ( B ) TYPE: Amino Acid
        ( D ) TOPOLOGY: Linear ( x i ) SEQUENCE DESCRIPTION: SEQ ID NO:22:

| Glu<br>1 | Val | Gln | Leu | Val<br>5 | Glu | Ser | Gly | Gly | Gly<br>10 | Leu | Val | Pro | Pro | Gly<br>15 |
|---|---|---|---|---|---|---|---|---|---|---|---|---|---|---|
| Gly | Ser | Leu | Lys | Leu<br>20 | Ser | Cys | Ala | Ala | Ser<br>25 | Gly | Phe | Ile | Phe | Ser<br>30 |
| Ser | Tyr | Gly | Met | Ser<br>35 | Trp | Val | Arg | Gln | Thr<br>40 | Pro | Gly | Lys | Ser | Leu<br>45 |
| Glu | Leu | Val | Ala | Thr<br>50 | Ile | Asn | Asn | Asn | Gly<br>55 | Asp | Ser | Thr | Tyr | Tyr<br>60 |
| Pro | Asp | Ser | Val | Lys<br>65 | Gly | Arg | Phe | Thr | Ile<br>70 | Ser | Arg | Asp | Asn | Ala<br>75 |
| Lys | Asn | Thr | Leu | Tyr<br>80 | Leu | Gln | Met | Ser | Ser<br>85 | Leu | Lys | Ser | Glu | Asp<br>90 |
| Thr | Ala | Met | Phe | Tyr<br>95 | Cys | Ala | Arg | Ala | Leu<br>100 | Ile | Ser | Ser | Ala | Thr<br>105 |
| Trp | Phe | Gly | Tyr | Trp<br>110 | Gly | Gln | Gly | Thr | Leu<br>115 | Val | Thr | Val | Ser | Ala<br>120 |
| Ala | Lys | Thr | Thr | Ala<br>125 | Pro | Ser | Val | Tyr | Pro<br>130 | | | | | |

( 2 ) INFORMATION FOR SEQ ID NO:23:

( i ) SEQUENCE CHARACTERISTICS:
- ( A ) LENGTH: 31 base pairs
- ( B ) TYPE: Nucleic Acid
- ( C ) STRANDEDNESS: Single
- ( D ) TOPOLOGY: Linear ( x i ) SEQUENCE DESCRIPTION: SEQ ID NO:23:

| | | | |
|---|---|---|---|
| ACAAACGCGT ACGCTGATAT CGTCATGACA G | | | 31 |

( 2 ) INFORMATION FOR SEQ ID NO:24:

( i ) SEQUENCE CHARACTERISTICS:
- ( A ) LENGTH: 31 base pairs
- ( B ) TYPE: Nucleic Acid
- ( C ) STRANDEDNESS: Single
- ( D ) TOPOLOGY: Linear ( x i ) SEQUENCE DESCRIPTION: SEQ ID NO:24:

GCAGCATCAG CTCTTCGAAG CTCCAGCTTG G                                       31

( 2 ) INFORMATION FOR SEQ ID NO:25:

( i ) SEQUENCE CHARACTERISTICS:
- ( A ) LENGTH: 21 base pairs
- ( B ) TYPE: Nucleic Acid
- ( C ) STRANDEDNESS: Single
- ( D ) TOPOLOGY: Linear ( x i ) SEQUENCE DESCRIPTION: SEQ ID NO:25:

CCACTAGTAC GCAAGTTCAC G                                                  21

( 2 ) INFORMATION FOR SEQ ID NO:26:

( i ) SEQUENCE CHARACTERISTICS:
- ( A ) LENGTH: 33 base pairs
- ( B ) TYPE: Nucleic Acid
- ( C ) STRANDEDNESS: Single
- ( D ) TOPOLOGY: Linear ( x i ) SEQUENCE DESCRIPTION: SEQ ID NO:26:

GATGGGCCCT TGGTGGAGGC TGCAGAGACA GTG                                     33

( 2 ) INFORMATION FOR SEQ ID NO:27:

( i ) SEQUENCE CHARACTERISTICS:
- ( A ) LENGTH: 714 base pairs
- ( B ) TYPE: Nucleic Acid
- ( C ) STRANDEDNESS: Double
- ( D ) TOPOLOGY: Linear ( x i ) SEQUENCE DESCRIPTION: SEQ ID NO:27:

ATGAAGAAGA ATATCGCATT TCTTCTTGCA TCTATGTTCG TTTTTTCTAT                    50
TGCTACAAAC GCGTACGCTG ATATCGTCAT GACACAGTCT CAAAAATTCA                   100
TGTCCACATC AGTAGGAGAC AGGGTCAGCG TCACCTGCAA GGCCAGTCAG                   150
AATGTGGGTA CTAATGTAGC CTGGTATCAA CAGAAACCAG GCAATCTCC                    200
TAAAGCACTG ATTTACTCGT CATCCTACCG GTACAGTGGA GTCCCTGATC                   250
GCTTCACAGG CAGTGGATCT GGGACAGATT TCACTCTCAC CATCAGCCAT                   300
GTGCAGTCTG AAGACTTGGC AGACTATTTC TGTCAGCAAT ATAACATCTA                   350
TCCTCTCACG TTCGGTCCTG GACCAAGCT GGAGCTTCGA AGAGCTGTGG                    400
CTGCACCATC TGTCTTCATC TTCCCGCCAT CTGATGAGCA GTTGAAATCT                   450
GGAACTGCTT CTGTTGTGTG CCTGCTGAAT AACTTCTATC CCAGAGAGGC                   500

| | | | | |
|---|---|---|---|---|
| CAAAGTACAG | TGGAAGGTGG | ATAACGCCCT | CCAATCGGGT | AACTCCCAGG | 550
| AGAGTGTCAC | AGAGCAGGAC | AGCAAGGACA | GCACCTACAG | CCTCAGCAGC | 600
| ACCCTGACGC | TGAGCAAAGC | AGACTACGAG | AAACACAAAG | TCTACGCCTG | 650
| CGAAGTCACC | CATCAGGGCC | TGAGCTCGCC | CGTCACAAAG | AGCTTCAACA | 700
| GGGGAGAGTG | TTAA | | | | 714

(2) INFORMATION FOR SEQ ID NO:28:

(i) SEQUENCE CHARACTERISTICS:
        (A) LENGTH: 237 amino acids
        (B) TYPE: Amino Acid
        (D) TOPOLOGY: Linear (xi) SEQUENCE DESCRIPTION: SEQ ID NO:28:

```
Met Lys Lys Asn Ile Ala Phe Leu Leu Ala Ser Met Phe Val Phe
 1               5                  10                  15
Ser Ile Ala Thr Asn Ala Tyr Ala Asp Ile Val Met Thr Gln Ser
                20                  25                  30
Gln Lys Phe Met Ser Thr Ser Val Gly Asp Arg Val Ser Val Thr
                35                  40                  45
Cys Lys Ala Ser Gln Asn Val Gly Thr Asn Val Ala Trp Tyr Gln
                50                  55                  60
Gln Lys Pro Gly Gln Ser Pro Lys Ala Leu Ile Tyr Ser Ser Ser
                65                  70                  75
Tyr Arg Tyr Ser Gly Val Pro Asp Arg Phe Thr Gly Ser Gly Ser
                80                  85                  90
Gly Thr Asp Phe Thr Leu Thr Ile Ser His Val Gln Ser Glu Asp
                95                  100                 105
Leu Ala Asp Tyr Phe Cys Gln Gln Tyr Asn Ile Tyr Pro Leu Thr
                110                 115                 120
Phe Gly Pro Gly Thr Lys Leu Glu Leu Arg Arg Ala Val Ala Ala
                125                 130                 135
Pro Ser Val Phe Ile Phe Pro Pro Ser Asp Glu Gln Leu Lys Ser
                140                 145                 150
Gly Thr Ala Ser Val Val Cys Leu Leu Asn Asn Phe Tyr Pro Arg
                155                 160                 165
Glu Ala Lys Val Gln Trp Lys Val Asp Asn Ala Leu Gln Ser Gly
                170                 175                 180
Asn Ser Gln Glu Ser Val Thr Glu Gln Asp Ser Lys Asp Ser Thr
                185                 190                 195
Tyr Ser Leu Ser Ser Thr Leu Thr Leu Ser Lys Ala Asp Tyr Glu
                200                 205                 210
Lys His Lys Val Tyr Ala Cys Glu Val Thr His Gln Gly Leu Ser
                215                 220                 225
Ser Pro Val Thr Lys Ser Phe Asn Arg Gly Glu Cys
                230                 235     237
```

(2) INFORMATION FOR SEQ ID NO:29:

(i) SEQUENCE CHARACTERISTICS:
        (A) LENGTH: 756 base pairs
        (B) TYPE: Nucleic Acid
        (C) STRANDEDNESS: Double
        (D) TOPOLOGY: Linear (xi) SEQUENCE DESCRIPTION: SEQ ID NO:29:

-continued

```
ATGAAAAAGA ATATCGCATT TCTTCTTGCA TCTATGTTCG TTTTTTCTAT          50

TGCTACAAAC GCGTACGCTG AGGTGCAGCT GGTGGAGTCT GGGGGAGGCT         100

TAGTGCCGCC TGGAGGGTCC CTGAAACTCT CCTGTGCAGC CTCTGGATTC         150

ATATTCAGTA GTTATGGCAT GTCTTGGGTT CGCCAGACTC CAGGCAAGAG         200

CCTGGAGTTG GTCGCAACCA TTAATAATAA TGGTGATAGC ACCTATTATC         250

CAGACAGTGT GAAGGGCCGA TTCACCATCT CCCGAGACAA TGCCAAGAAC         300

ACCCTGTACC TGCAAATGAG CAGTCTGAAG TCTGAGGACA CAGCCATGTT         350

TTACTGTGCA AGAGCCCTCA TTAGTTCGGC TACTTGGTTT GGTTACTGGG         400

GCCAAGGGAC TCTGGTCACT GTCTCTGCAG CCTCCACCAA GGGCCCATCG         450

GTCTTCCCCC TGGCACCCTC CTCCAAGAGC ACCTCTGGGG CACAGCGGC          500

CCTGGGCTGC CTGGTCAAGG ACTACTTCCC CGAACCGGTG ACGGTGTCGT         550

GGAACTCAGG CGCCCTGACC AGCGGCGTGC ACACCTTCCC GGCTGTCCTA         600

CAGTCCTCAG GACTCTACTC CCTCAGCAGC GTGGTGACCG TGCCCTCCAG         650

CAGCTTGGGC ACCCAGACCT ACATCTGCAA CGTGAATCAC AAGCCCAGCA         700

ACACCAAGGT GGACAAGAAA GTTGAGCCCA AATCTTGTGA CAAAACTCAC         750

ACATGA                                                         756
```

(2) INFORMATION FOR SEQ ID NO:30:

(i) SEQUENCE CHARACTERISTICS:
        (A) LENGTH: 251 amino acids
        (B) TYPE: Amino Acid
        (D) TOPOLOGY: Linear (xi) SEQUENCE DESCRIPTION: SEQ ID NO:30:

```
Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
                20                  25                  30

Gly Gly Gly Leu Val Pro Pro Gly Gly Ser Leu Lys Leu Ser Cys
                35                  40                  45

Ala Ala Ser Gly Phe Ile Phe Ser Ser Tyr Gly Met Ser Trp Val
                50                  55                  60

Arg Gln Thr Pro Gly Lys Ser Leu Glu Leu Val Ala Thr Ile Asn
                65                  70                  75

Asn Asn Gly Asp Ser Thr Tyr Tyr Pro Asp Ser Val Lys Gly Arg
                80                  85                  90

Phe Thr Ile Ser Arg Asp Asn Ala Lys Asn Thr Leu Tyr Leu Gln
                95                 100                 105

Met Ser Ser Leu Lys Ser Glu Asp Thr Ala Met Phe Tyr Cys Ala
               110                 115                 120

Arg Ala Leu Ile Ser Ser Ala Thr Trp Phe Gly Tyr Trp Gly Gln
               125                 130                 135

Gly Thr Leu Val Thr Val Ser Ala Ala Ser Thr Lys Gly Pro Ser
               140                 145                 150

Val Phe Pro Leu Ala Pro Ser Ser Lys Ser Thr Ser Gly Gly Thr
               155                 160                 165

Ala Ala Leu Gly Cys Leu Val Lys Asp Tyr Phe Pro Glu Pro Val
               170                 175                 180

Thr Val Ser Trp Asn Ser Gly Ala Leu Thr Ser Gly Val His Thr
               185                 190                 195
```

```
Phe  Pro  Ala  Val  Leu  Gln  Ser  Ser  Gly  Leu  Tyr  Ser  Leu  Ser  Ser
               200                      205                     210

Val  Val  Thr  Val  Pro  Ser  Ser  Ser  Leu  Gly  Thr  Gln  Thr  Tyr  Ile
               215                      220                     225

Cys  Asn  Val  Asn  His  Lys  Pro  Ser  Asn  Thr  Lys  Val  Asp  Lys  Lys
               230                      235                     240

Val  Glu  Pro  Lys  Ser  Cys  Asp  Lys  Thr  His  Thr
               245                      250  251
```

( 2 ) INFORMATION FOR SEQ ID NO:31:

( i ) SEQUENCE CHARACTERISTICS:
        ( A ) LENGTH: 22 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:31:

```
CAGTCCAACT GTTCAGGACG CC                                               22
```

( 2 ) INFORMATION FOR SEQ ID NO:32:

( i ) SEQUENCE CHARACTERISTICS:
        ( A ) LENGTH: 22 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:32:

```
GTGCTGCTCA TGCTGTAGGT GC                                               22
```

( 2 ) INFORMATION FOR SEQ ID NO:33:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:33:

```
GAAGTTGATG TCTTGTGAGT GGC                                              23
```

( 2 ) INFORMATION FOR SEQ ID NO:34:

( i ) SEQUENCE CHARACTERISTICS:
        ( A ) LENGTH: 24 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:34:

```
GCATCCTAGA GTCACCGAGG AGCC                                             24
```

( 2 ) INFORMATION FOR SEQ ID NO:35:

( i ) SEQUENCE CHARACTERISTICS:
        ( A ) LENGTH: 22 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:35:

```
CACTGGCTCA GGGAAATAAC CC                                               22
```

( 2 ) INFORMATION FOR SEQ ID NO:36:

( i ) SEQUENCE CHARACTERISTICS:
  ( A ) LENGTH: 22 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:36:

GGAGAGCTGG GAAGGTGTGC AC    22

( 2 ) INFORMATION FOR SEQ ID NO:37:

( i ) SEQUENCE CHARACTERISTICS:
  ( A ) LENGTH: 37 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:37:

CCAATGCATA CGCTGACATC GTGATGACCC AGACCCC    37

( 2 ) INFORMATION FOR SEQ ID NO:38:

( i ) SEQUENCE CHARACTERISTICS:
  ( A ) LENGTH: 37 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:38:

CCAATGCATA CGCTGATATT GTGATGACTC AGACTCC    37

( 2 ) INFORMATION FOR SEQ ID NO:39:

( i ) SEQUENCE CHARACTERISTICS:
  ( A ) LENGTH: 37 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:39:

CCAATGCATA CGCTGACATC GTGATGACAC AGACACC    37

( 2 ) INFORMATION FOR SEQ ID NO:40:

( i ) SEQUENCE CHARACTERISTICS:
  ( A ) LENGTH: 35 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:40:

AGATGTCAAT TGCTCACTGG ATGGTGGGAA GATGG    35

( 2 ) INFORMATION FOR SEQ ID NO:41:

( i ) SEQUENCE CHARACTERISTICS:
  ( A ) LENGTH: 32 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:41:

CAAACGCGTA CGCTGAGATC CAGCTGCAGC AG    32

( 2 ) INFORMATION FOR SEQ ID NO:42:

( i ) SEQUENCE CHARACTERISTICS:

(A) LENGTH: 32 base pairs
(B) TYPE: Nucleic Acid
(C) STRANDEDNESS: Single
(D) TOPOLOGY: Linear (xi) SEQUENCE DESCRIPTION: SEQ ID NO:42:

CAAACGCGTA CGCTGAGATT CAGCTCCAGC AG 32

(2) INFORMATION FOR SEQ ID NO:43:

(i) SEQUENCE CHARACTERISTICS:
(A) LENGTH: 39 base pairs
(B) TYPE: Nucleic Acid
(C) STRANDEDNESS: Single
(D) TOPOLOGY: Linear (xi) SEQUENCE DESCRIPTION: SEQ ID NO:43:

CGATGGGCCC GGATAGACCG ATGGGGCTGT TGTTTTGGC 39

(2) INFORMATION FOR SEQ ID NO:44:

(i) SEQUENCE CHARACTERISTICS:
(A) LENGTH: 39 base pairs
(B) TYPE: Nucleic Acid
(C) STRANDEDNESS: Single
(D) TOPOLOGY: Linear (xi) SEQUENCE DESCRIPTION: SEQ ID NO:44:

CGATGGGCCC GGATAGACTG ATGGGGCTGT TGTTTTGGC 39

(2) INFORMATION FOR SEQ ID NO:45:

(i) SEQUENCE CHARACTERISTICS:
(A) LENGTH: 39 base pairs
(B) TYPE: Nucleic Acid
(C) STRANDEDNESS: Single
(D) TOPOLOGY: Linear (xi) SEQUENCE DESCRIPTION: SEQ ID NO:45:

CGATGGGCCC GGATAGACAG ATGGGGCTGT TGTTTTGGC 39

(2) INFORMATION FOR SEQ ID NO:46:

(i) SEQUENCE CHARACTERISTICS:
(A) LENGTH: 39 base pairs
(B) TYPE: Nucleic Acid
(C) STRANDEDNESS: Double
(D) TOPOLOGY: Linear (xi) SEQUENCE DESCRIPTION: SEQ ID NO:46:

CGATGGGCCC GGATAGACGG ATGGGGCTGT TGTTTTGGC 39

(2) INFORMATION FOR SEQ ID NO:47:

(i) SEQUENCE CHARACTERISTICS:
(A) LENGTH: 391 base pairs
(B) TYPE: Nucleic Acid
(C) STRANDEDNESS: Double
(D) TOPOLOGY: Linear (xi) SEQUENCE DESCRIPTION: SEQ ID NO:47:

GATATCGTGA TGACACAGAC ACCACTCTCC CTGCCTGTCA GTCTTGGAGA 50

TCAGGCCTCC ATCTCTTGCA GATCTAGTCA GAGCCTTGTA CACGGTATTG 100

GAAACACCTA TTTACATTGG TACCTGCAGA AGCCAGGCCA GTCTCCAAAG 150

CTCCTGATCT ACAAAGTTTC CAACCGATTT TCTGGGGTCC CAGACAGGTT 200

```
CAGTGGCAGT  GGATCAGGGA  CAGATTTCAC  ACTCAGGATC  AGCAGAGTGG                250

AGGCTGAGGA  TCTGGGACTT  TATTTCTGCT  CTCAAAGTAC  ACATGTTCCG                300

CTCACGTTCG  GTGCTGGGAC  CAAGCTGGAG  CTGAAACGGG  CTGATGCTGC                350

ACCAACTGTA  TCCATCTTCC  CACCATCCAG  TGAGCAATTG  A                         391
```

( 2 ) INFORMATION FOR SEQ ID NO:48:

( i ) SEQUENCE CHARACTERISTICS:
        ( A ) LENGTH: 131 amino acids
        ( B ) TYPE: Amino Acid
        ( D ) TOPOLOGY: Linear ( x i ) SEQUENCE DESCRIPTION: SEQ ID NO:48:

```
Asp  Ile  Val  Met  Thr  Gln  Thr  Pro  Leu  Ser  Leu  Pro  Val  Ser  Leu
 1              5                        10                           15

Gly  Asp  Gln  Ala  Ser  Ile  Ser  Cys  Arg  Ser  Gln  Ser  Leu  Val
                20                        25                       30

His  Gly  Ile  Gly  Asn  Thr  Tyr  Leu  His  Trp  Tyr  Leu  Gln  Lys  Pro
                    35                        40                       45

Gly  Gln  Ser  Pro  Lys  Leu  Leu  Ile  Tyr  Lys  Val  Ser  Asn  Arg  Phe
                50                        55                          60

Ser  Gly  Val  Pro  Asp  Arg  Phe  Ser  Gly  Ser  Gly  Ser  Gly  Thr  Asp
                65                        70                          75

Phe  Thr  Leu  Arg  Ile  Ser  Arg  Val  Glu  Ala  Glu  Asp  Leu  Gly  Leu
                    80                        85                       90

Tyr  Phe  Cys  Ser  Gln  Ser  Thr  His  Val  Pro  Leu  Thr  Phe  Gly  Ala
                    95                       100                      105

Gly  Thr  Lys  Leu  Glu  Leu  Lys  Arg  Ala  Asp  Ala  Ala  Pro  Thr  Val
                   110                       115                      120

Ser  Ile  Phe  Pro  Pro  Ser  Ser  Glu  Gln  Leu  Lys
                   125                       130  131
```

( 2 ) INFORMATION FOR SEQ ID NO:49:

( i ) SEQUENCE CHARACTERISTICS:
        ( A ) LENGTH: 405 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:49:

```
GAGATTCAGC  TGCAGCAGTC  TGGACCTGAG  CTGATGAAGC  CTGGGGCTTC                 50

AGTGAAGATA  TCCTGCAAGG  CTTCTGGTTA  TTCATTCAGT  AGCCACTACA                100

TGCACTGGGT  GAAGCAGAGC  CATGGAAAGA  GCCTTGAGTG  GATTGGCTAC                150

ATTGATCCTT  CCAATGGTGA  AACTACTTAC  AACCAGAAAT  TCAAGGGCAA                200

GGCCACATTG  ACTGTAGACA  CATCTTCCAG  CACAGCCAAC  GTGCATCTCA                250

GCAGCCTGAC  ATCTGATGAC  TCTGCAGTCT  ATTTCTGTGC  AAGAGGGGAC                300

TATAGATACA  ACGGCGACTG  GTTTTTCGAT  GTCTGGGGNG  NAGGGACCAC                350

GGTCACCGTC  TCCTCCGCCA  AAACCGACAG  CCCCATCGGT  CTATCCGGGC                400

CCATC                                                                    405
```

( 2 ) INFORMATION FOR SEQ ID NO:50:

( i ) SEQUENCE CHARACTERISTICS:
        ( A ) LENGTH: 135 amino acids
        ( B ) TYPE: Amino Acid (D) TOPOLOGY: Linear (xi) SEQUENCE DESCRIPTION: SEQ ID NO:50:

| Glu | Ile | Gln | Leu | Gln | Gln | Ser | Gly | Pro | Glu | Leu | Met | Lys | Pro | Gly |
|---|---|---|---|---|---|---|---|---|---|---|---|---|---|---|
| 1 | | | | 5 | | | | | 10 | | | | | 15 |

| Ala | Ser | Val | Lys | Ile | Ser | Cys | Lys | Ala | Ser | Gly | Tyr | Ser | Phe | Ser |
|---|---|---|---|---|---|---|---|---|---|---|---|---|---|---|
| | | | | 20 | | | | | 25 | | | | | 30 |

| Ser | His | Tyr | Met | His | Trp | Val | Lys | Gln | Ser | His | Gly | Lys | Ser | Leu |
|---|---|---|---|---|---|---|---|---|---|---|---|---|---|---|
| | | | | 35 | | | | | 40 | | | | | 45 |

| Glu | Trp | Ile | Gly | Tyr | Ile | Asp | Pro | Ser | Asn | Gly | Glu | Thr | Thr | Tyr |
|---|---|---|---|---|---|---|---|---|---|---|---|---|---|---|
| | | | | 50 | | | | | 55 | | | | | 60 |

| Asn | Gln | Lys | Phe | Lys | Gly | Lys | Ala | Thr | Leu | Thr | Val | Asp | Thr | Ser |
|---|---|---|---|---|---|---|---|---|---|---|---|---|---|---|
| | | | | 65 | | | | | 70 | | | | | 75 |

| Ser | Ser | Thr | Ala | Asn | Val | His | Leu | Ser | Ser | Leu | Thr | Ser | Asp | Asp |
|---|---|---|---|---|---|---|---|---|---|---|---|---|---|---|
| | | | | 80 | | | | | 85 | | | | | 90 |

| Ser | Ala | Val | Tyr | Phe | Cys | Ala | Arg | Gly | Asp | Tyr | Arg | Tyr | Asn | Gly |
|---|---|---|---|---|---|---|---|---|---|---|---|---|---|---|
| | | | | 95 | | | | | 100 | | | | | 105 |

| Asp | Trp | Phe | Phe | Asp | Val | Trp | Gly | Xaa | Gly | Thr | Thr | Val | Thr | Val |
|---|---|---|---|---|---|---|---|---|---|---|---|---|---|---|
| | | | | 110 | | | | | 115 | | | | | 120 |

| Ser | Ser | Ala | Lys | Thr | Asp | Ser | Pro | Ile | Gly | Leu | Ser | Gly | Pro | Ile |
|---|---|---|---|---|---|---|---|---|---|---|---|---|---|---|
| | | | | 125 | | | | | 130 | | | | | 135 |

(2) INFORMATION FOR SEQ ID NO:51:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:51:

CTTGGTGGAG GCGGAGGAGA CG        22

(2) INFORMATION FOR SEQ ID NO:52:

(i) SEQUENCE CHARACTERISTICS:
        (A) LENGTH: 38 base pairs
        (B) TYPE: Nucleic Acid
        (C) STRANDEDNESS: Single
        (D) TOPOLOGY: Linear (xi) SEQUENCE DESCRIPTION: SEQ ID NO:52:

GAAACGGGCT GTTGCTGCAC CAACTGTATT CATCTTCC        38

(2) INFORMATION FOR SEQ ID NO:53:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO:53:

GTCACCGTCT CCTCCGCCTC CACCAAGGGC C        31

(2) INFORMATION FOR SEQ ID NO:54:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:54:

CTTGGTGGAG GCGGAGGAGA CG                              22

( 2 ) INFORMATION FOR SEQ ID NO:55:

( i ) SEQUENCE CHARACTERISTICS:
        ( A ) LENGTH: 729 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:55:

```
ATGAAGAAGA ATATCGCATT TCTTCTTGCA TCTATGTTCG TTTTTTCTAT      50
TGCTACAAAT GCATACGCTG ATATCGTGAT GACACAGACA CCACTCTCCC     100
TGCCTGTCAG TCTTGGAGAT CAGGCCTCCA TCTCTTGCAG ATCTAGTCAG     150
AGCCTTGTAC ACGGTATTGG AAACACCTAT TTACATTGGT ACCTGCAGAA     200
GCCAGGCCAG TCTCCAAAGC TCCTGATCTA CAAAGTTTCC AACCGATTTT     250
CTGGGGTCCC AGACAGGTTC AGTGGCAGTG GATCAGGGAC AGATTTCACA     300
CTCAGGATCA GCAGAGTGGA GGCTGAGGAT CTGGGACTTT ATTTCTGCTC     350
TCAAAGTACA CATGTTCCGC TCACGTTCGG TGCTGGGACC AAGCTGGAGC     400
TGAAACGGGC TGTTGCTGCA CCAACTGTAT TCATCTTCCC ACCATCCAGT     450
GAGCAATTGA AATCTGGAAC TGCCTCTGTT GTGTGCCTGC TGAATAACTT     500
CTATCCCAGA GAGGCCAAAG TACAGTGGAA GGTGGATAAC GCCCTCCAAT     550
CGGGTAACTC CCAGGAGAGT GTCACAGAGC AGGACAGCAA GGACAGCACC     600
TACAGCCTCA GCAGCACCCT GACGCTGAGC AAAGCAGACT ACGAGAAACA     650
CAAAGTCTAC GCCTGCGAAG TCACCCATCA GGGCCTGAGC TCGCCCGTCA     700
CAAAGAGCTT CAACAGGGGA GAGTGTTAA                           729
```

( 2 ) INFORMATION FOR SEQ ID NO:56:

( i ) SEQUENCE CHARACTERISTICS:
        ( A ) LENGTH: 242 amino acids
        ( B ) TYPE: Amino Acid
        ( D ) TOPOLOGY: Linear ( x i ) SEQUENCE DESCRIPTION: SEQ ID NO:56:

```
Met Lys Lys Asn Ile Ala Phe Leu Leu Ala Ser Met Phe Val Phe
 1               5                  10                  15
Ser Ile Ala Thr Asn Ala Tyr Ala Asp Ile Val Met Thr Gln Thr
                20                  25                  30
Pro Leu Ser Leu Pro Val Ser Leu Gly Asp Gln Ala Ser Ile Ser
                35                  40                  45
Cys Arg Ser Ser Gln Ser Leu Val His Gly Ile Gly Asn Thr Tyr
                50                  55                  60
Leu His Trp Tyr Leu Gln Lys Pro Gly Gln Ser Pro Lys Leu Leu
                65                  70                  75
Ile Tyr Lys Val Ser Asn Arg Phe Ser Gly Val Pro Asp Arg Phe
                80                  85                  90
Ser Gly Ser Gly Ser Gly Thr Asp Phe Thr Leu Arg Ile Ser Arg
                95                  100                 105
Val Glu Ala Glu Asp Leu Gly Leu Tyr Phe Cys Ser Gln Ser Thr
                110                 115                 120
His Val Pro Leu Thr Phe Gly Ala Gly Thr Lys Leu Glu Leu Lys
                125                 130                 135
```

| | | | | | | | | | | | | | | |
|---|---|---|---|---|---|---|---|---|---|---|---|---|---|---|
| Arg | Ala | Val | Ala | Ala<br>140 | Pro | Thr | Val | Phe | Ile<br>145 | Phe | Pro | Pro | Ser | Ser<br>150 |
| Glu | Gln | Leu | Lys | Ser<br>155 | Gly | Thr | Ala | Ser | Val<br>160 | Val | Cys | Leu | Leu | Asn<br>165 |
| Asn | Phe | Tyr | Pro | Arg<br>170 | Glu | Ala | Lys | Val | Gln<br>175 | Trp | Lys | Val | Asp | Asn<br>180 |
| Ala | Leu | Gln | Ser | Gly<br>185 | Asn | Ser | Gln | Glu | Ser<br>190 | Val | Thr | Glu | Gln | Asp<br>195 |
| Ser | Lys | Asp | Ser | Thr<br>200 | Tyr | Ser | Leu | Ser | Ser<br>205 | Thr | Leu | Thr | Leu | Ser<br>210 |
| Lys | Ala | Asp | Tyr | Glu<br>215 | Lys | His | Lys | Val | Tyr<br>220 | Ala | Cys | Glu | Val | Thr<br>225 |
| His | Gln | Gly | Leu | Ser<br>230 | Ser | Pro | Val | Thr | Lys<br>235 | Ser | Phe | Asn | Arg | Gly<br>240 |
| Glu | Cys<br>242 | | | | | | | | | | | | | |

( 2 ) INFORMATION FOR SEQ ID NO:57:

( i ) SEQUENCE CHARACTERISTICS:
        ( A ) LENGTH: 762 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:57:

| | | | | | |
|---|---|---|---|---|---|
| ATGAAAAAGA | ATATCGCATT | TCTTCTTGCA | TCTATGTTCG | TTTTTTCTAT | 50 |
| TGCTACAAAC | GCGTACGCTG | AGATTCAGCT | GCAGCAGTCT | GGACCTGAGC | 100 |
| TGATGAAGCC | TGGGGCTTCA | GTGAAGATAT | CCTGCAAGGC | TTCTGGTTAT | 150 |
| TCATTCAGTA | GCCACTACAT | GCACTGGGTG | AAGCAGAGCC | ATGGAAAGAG | 200 |
| CCTTGAGTGG | ATTGGCTACA | TTGATCCTTC | CAATGGTGAA | ACTACTTACA | 250 |
| ACCAGAAATT | CAAGGGCAAG | GCCACATTGA | CTGTAGACAC | ATCTTCCAGC | 300 |
| ACAGCCAACG | TGCATCTCAG | CAGCCTGACA | TCTGATGACT | CTGCAGTCTA | 350 |
| TTTCTGTGCA | AGAGGGGACT | ATAGATACAA | CGGCGACTGG | TTTTTCGATG | 400 |
| TCTGGGGCGC | AGGGACCACG | GTCACCGTCT | CCTCCGCCTC | CACCAAGGGC | 450 |
| CCATCGGTCT | TCCCCCTGGC | ACCCTCCTCC | AAGAGCACCT | CTGGGGGCAC | 500 |
| AGCGGCCCTG | GGCTGCCTGG | TCAAGGACTA | CTTCCCCGAA | CCGGTGACGG | 550 |
| TGTCGTGGAA | CTCAGGCGCC | CTGACCAGCG | GCGTGCACAC | CTTCCCGGCT | 600 |
| GTCCTACAGT | CCTCAGGACT | CTACTCCCTC | AGCAGCGTGG | TGACCGTGCC | 650 |
| CTCCAGCAGC | TTGGGCACCC | AGACCTACAT | CTGCAACGTG | AATCACAAGC | 700 |
| CCAGCAACAC | CAAGGTGGAC | AAGAAAGTTG | AGCCCAAATC | TTGTGACAAA | 750 |
| ACTCACACAT | GA | | | | 762 |

( 2 ) INFORMATION FOR SEQ ID NO:58:

( i ) SEQUENCE CHARACTERISTICS:
        ( A ) LENGTH: 253 amino acids
        ( B ) TYPE: Amino Acid
        ( D ) TOPOLOGY: Linear ( x i ) SEQUENCE DESCRIPTION: SEQ ID NO:58:

| | | | | | | | | | | | | | | |
|---|---|---|---|---|---|---|---|---|---|---|---|---|---|---|
| Met<br>1 | Lys | Lys | Asn | Ile<br>5 | Ala | Phe | Leu | Leu | Ala<br>10 | Ser | Met | Phe | Val | Phe<br>15 |

| | | | | | | | | | | | | |
|---|---|---|---|---|---|---|---|---|---|---|---|---|
| Ser | Ile | Ala | Thr | Asn 20 | Ala | Tyr | Ala | Glu | Ile 25 | Gln | Leu | Gln | Gln | Ser 30 |
| Gly | Pro | Glu | Leu | Met 35 | Lys | Pro | Gly | Ala | Ser 40 | Val | Lys | Ile | Ser | Cys 45 |
| Lys | Ala | Ser | Gly | Tyr 50 | Ser | Phe | Ser | Ser | His 55 | Tyr | Met | His | Trp | Val 60 |
| Lys | Gln | Ser | His | Gly 65 | Lys | Ser | Leu | Glu | Trp 70 | Ile | Gly | Tyr | Ile | Asp 75 |
| Pro | Ser | Asn | Gly | Glu 80 | Thr | Thr | Tyr | Asn | Gln 85 | Lys | Phe | Lys | Gly | Lys 90 |
| Ala | Thr | Leu | Thr | Val 95 | Asp | Thr | Ser | Ser | Ser 100 | Thr | Ala | Asn | Val | His 105 |
| Leu | Ser | Ser | Leu | Thr 110 | Ser | Asp | Asp | Ser | Ala 115 | Val | Tyr | Phe | Cys | Ala 120 |
| Arg | Gly | Asp | Tyr | Arg 125 | Tyr | Asn | Gly | Asp | Trp 130 | Phe | Phe | Asp | Val | Trp 135 |
| Gly | Ala | Gly | Thr | Thr 140 | Val | Thr | Val | Ser | Ser 145 | Ala | Ser | Thr | Lys | Gly 150 |
| Pro | Ser | Val | Phe | Pro 155 | Leu | Ala | Pro | Ser | Ser 160 | Lys | Ser | Thr | Ser | Gly 165 |
| Gly | Thr | Ala | Ala | Leu 170 | Gly | Cys | Leu | Val | Lys 175 | Asp | Tyr | Phe | Pro | Glu 180 |
| Pro | Val | Thr | Val | Ser 185 | Trp | Asn | Ser | Gly | Ala 190 | Leu | Thr | Ser | Gly | Val 195 |
| His | Thr | Phe | Pro | Ala 200 | Val | Leu | Gln | Ser | Ser 205 | Gly | Leu | Tyr | Ser | Leu 210 |
| Ser | Ser | Val | Val | Thr 215 | Val | Pro | Ser | Ser | Ser 220 | Leu | Gly | Thr | Gln | Thr 225 |
| Tyr | Ile | Cys | Asn | Val 230 | Asn | His | Lys | Pro | Ser 235 | Asn | Thr | Lys | Val | Asp 240 |
| Lys | Lys | Val | Glu | Pro 245 | Lys | Ser | Cys | Asp | Lys 250 | Thr | His | Thr 253 | | |

ANTI-IL-8 MONOCLONAL ANTIBODIES FOR TREATMENT OF ASTHMA

This application is a continuation-in-part of U.S. Ser. No. 08/398,611 filed Mar. 1, 1995, which is a continuation-in-part of U.S. Ser. No. 08/205,864, filed Mar. 3, 1994, abandoned, which applications are specifically incorporated herein by reference in their entirety.

FIELD OF THE INVENTION

This application relates to IL-8 antagonists, such as anti-interleukin-8 (IL-8) antibodies, and their use in the treatment of inflammatory disorders and asthma.

BACKGROUND

Interleukin-8 (IL-8) is neutrophil chemotactic peptide secreted by a variety of cells in response to inflammatory mediators (for a review see Hebert et al. *Cancer Investigation* 11(6):743 (1993)). IL-8 can play an important role in the pathogenesis of inflammatory disorders, such as adult respiratory distress syndrome (ARDS), septic shock, and multiple organ failure. Immune therapy for such inflammatory disorders can include treatment of an affected patient with anti-IL-8 antibodies.

Sticherling et al. (*J. Immunol.* 143:1628 (1989)) disclose the production and characterization of four monoclonal antibodies against IL-8. WO 92/04372, published Mar. 19, 1992, discloses polyclonal antibodies which react with the receptor-interacting site of IL-8 and peptide analogs of IL-8, along with the use of such antibodies to prevent an inflammatory response in patients. St. John et al. (*Chest* 103:932 (1993)) review immune therapy for ARDS, septic shock, and multiple organ failure, including the potential therapeutic use of anti-IL-8 antibodies Sekido et al. (*Nature* 365:654 (1993)) disclose the prevention of lung reperfusion injury in rabbits by a monoclonal antibody against IL-8. Mulligan et al. (*J. Immunol.* 150:5585 (1993)), disclose protective effects of a murine monoclonal antibody to human IL-8 in inflammatory lung injury in rats.

The instant invention demonstrates that the anti-IL-8 monoclonal antibodies of the invention can be used therapeutically in the treatment of other inflammatory disorders, such as bacterial pneumonias and inflammatory bowel disease.

Anti-IL-8 antibodies are additionally useful as reagents for assaying IL-8. For example, Sticherling et al. (*Arch. Dermatol. Res.* 284:82 (1992)), disclose the use of anti-IL-8 monoclonal antibodies as reagents in immunohistochemical studies. Ko et al. (*J. Immunol. Methods* 149:227 (1992)) disclose the use of anti-IL-8 monoclonal antibodies as reagents in an enzyme-linked immunoabsorbent assay (ELISA) for IL-8.

The invention further demonstrates that IL-8 antagonists, including anti-IL-8 monoclonal antibodies, can be used therapeutically in the treatment of asthma.

SUMMARY OF THE INVENTION

The invention provides a method of treating asthma in a subject comprising administering a therapeutically effective amount of an IL-8 antagonist. The methods of the invention provide for administration of IL-8 antagonist to the subject before and/or after the onset of asthma.

In one aspect, the invention provides a method of treating asthma with an anti-IL-8 antibody.

In another aspect, the invention provides a method of treating asthma with an IL-8 antagonist that inhibits IL-8 binding to neutrophils.

In still another aspect, the invention provides a method of treating asthma with an IL-8 antagonist that inhibits neutrophil chemotaxis induced by IL-8.

In a further aspect, the invention provides a method of treating asthma with an IL-8 antagonist that inhibits neutrophil elastase release induced by IL-8.

BRIEF DESCRIPTION OF THE FIGURES

FIG. 11A depicts myeloperoxidase levels in tissue; FIG. 11B depicts IL-8 levels in tissue; FIG. 11C depicts colon weight; FIG. 11D depicts gross inflammation; FIG. 11E depicts edema; FIG. 11F depicts extent of necrosis; FIG. 11G depicts severity of necrosis; FIG. 11 H depicts neutrophil margination; FIG. 11I depicts neutrophil infiltration; and FIG. 11J depicts mononuclear infiltration.

FIG. 13 depicts the DNA sequences of three primers designed for each of the light and heavy chains. Multiple primers were designed in order to increase the chances of primer hybridization and efficiency of first strand cDNA synthesis for cloning the variable light and heavy regions of monoclonal antibody 5.12.14.

FIG. 14 depicts the DNA sequences of one forward primer and one reverse primer for the 5.12.14 light chain variable region amplification.

FIG. 15 depicts the DNA sequences of one forward primer and one reverse primer for the 5.12.14 heavy chain variable region amplification.

FIG. 16 depicts the DNA sequence of the 5.12.14 light chain variable region. Complementarity-determining regions (CDRs) are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable light region is amino acids 1 to 109. The partial murine constant light region is amino acids 110 to 123 (in italics).

FIG. 17 depicts the DNA sequence of the 5.12.14 heavy chain variable region. CDRs are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable heavy region is amino acids 1 to 120. The partial murine constant heavy region is amino acids 121 to 130.

FIG. 18 depicts the DNA sequences of amplification primers used to convert murine light and heavy chain constant region residues to their human equivalents.

FIG. 19 depicts the coding sequence for the 5.12.14 light chain variable region and the human IgG1 light chain constant region. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable light region is amino acids 1 to 109. The human constant light region is amino acids 110 to 215.

FIG. 20 depicts the coding sequence for the 5.12.14 heavy chain variable region and the heavy chain constant region of human IgG1. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 120. The human constant heavy region is amino acids 121 to 228.

FIG. 21 depicts the DNA sequences of three primers designed for each of the light and heavy chains. Multiple primers were designed in order to increase the chances of primer hybridization and efficiency of first strand cDNA synthesis for cloning the variable light and heavy regions of monoclonal antibody 6G4.2.5.

FIG. 22 depicts the DNA sequences of one forward primer and one reverse primer for the 6G4.2.5 light chain variable region amplification.

FIG. 23 depicts the DNA sequences of one forward primer and one reverse primer for the 6G4.2.5 heavy chain variable region amplification.

FIG. 24 depicts the DNA sequence of the 6G4.2.5 light chain variable region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable light region is amino acids 1 to 114. The partial murine constant light region is amino acids 115 to 131.

FIG. 25 depicts the DNA sequence of the 6G4.2.5 heavy chain variable region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable heavy region is amino acids 1 to 122. The partial murine constant heavy region is amino acids 123 to 135.

FIG. 26 depicts primers to convert the murine light chain and heavy chain constant regions to their human equivalents.

FIG. 27 depicts the coding sequence for the chimeric 6G4.2.5 light chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 114. The human constant heavy region is amino acids 115 to 219.

FIG. 28 depicts the coding sequence for the chimeric 6G4.2.5 heavy chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 122. The human constant heavy region is amino acids 123 to 230.

FIG. 31 is a graph depicting the effect of the absence of IL8Rh on eosinophil transmigration into the lung and peripheral eosinophil proliferation in an asthma model using wild type and IL8Rh knock-out (KO) mice. Eosinophil transmigration is presented as BAL fluid eosinophil counts (diagonally hatched columns). Circulating blood eosinophil counts are shown as solid columns. Cell counts obtained on day 0 before ip allergen inoculation of WT and IL8Rh KO mice are denoted as "WT day 0" and "KO day 0", respectively. Cell counts obtained on the day following completion of aerosolized allergen challenge of WT and IL8Rh KO mice are denoted as "WT day 21" and "KO day 21", respectively.

FIG. 32 is a graph depicting a secondary IgE response in WT and IL8Rh KO mice initially challenged with ovalbumin allergen ip inoculation and subsequently challenged with allergen aerosolization. Allergen-specific IgE titers for WT and IL8Rh KO control mice challenged with aerosolized allergen without prior allergen challenge are denoted as "WT OVA aero" and "KO OVA aero", respectively. Allergen-specific IgE titers for WT and IL8Rh KO mice initially challenged with allergen by ip inoculation and subsequently exposed to aerosolized allergen are denoted as "WT OVA ip/aero" and "KO OVA ip/aero", respectively.

FIG. 33 shows that almost every bronchius is heavily infiltrated with granulocytes. A higher magnification of the most affected area (shown in FIG. 34) reveals a strong monocytic infiltrate with several eosinophils. At the alveolar level (the highest magnification, shown in FIG. 35), macrophages and eosinophils are apparent.

As shown in FIGS. 36 and 37, the least affected WT asthmatic mouse presents cell infiltrates in most bronchii, albeit less extensive than the infiltration presented by the most affected WT animal (FIGS. 33–35). The alveoli of the least affected WT animal are also less obstructed as shown in FIG. 38.

FIG. 39 shows that only the larger bronchii are infiltrated The extent of infiltration shown in FIGS. 39 and 40 is comparable to that shown in FIGS. 36 and 37 for the least affected WT mouse. At the alveolar level, only a few infiltrating cells are apparent in the most severely affected IL8Rh KO specimen (FIG. 41).

DESCRIPTION OF THE PREFERRED EMBODIMENTS

A. DEFINITIONS

Figure 1:
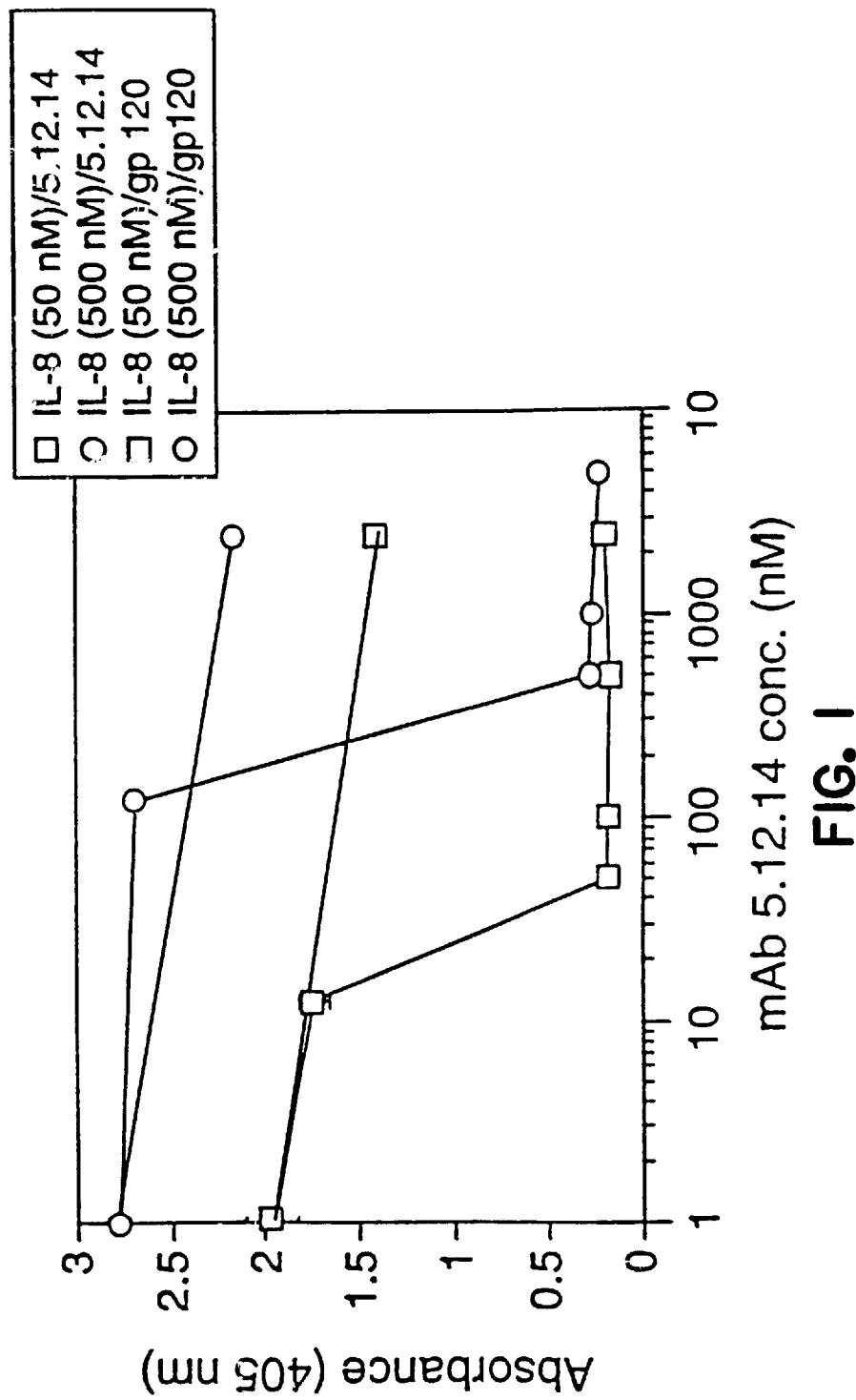
FIG. 1 is a graph depicting the blocking of IL-8 mediated elastase release by neutrophils by anti-IL-8 monoclonal antibody 5.12.14.

In general, the following words or phrases have the indicated definition when used in the description, examples, and claims.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and complementary DNA (cDNA) transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Press, New York, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.* 186:651 (1985); Novotny and Haber, *Proc. Natl. Acad. Sci. U.S.A.* 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc"

fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$–$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab' fragments differ from Fab fragments by the addition of a few residues at the carboxy terminus of the heavy chain $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa ($\kappa$) and lambda ($\lambda$), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

The term "antibody" is used in the broadest sense and specifically covers single monoclonal antibodies (including agonist and antagonist antibodies) and antibody compositions with polyepitopic specificity.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins.

The monoclonal antibodies herein include hybrid and recombinant antibodies produced by splicing a variable (including hypervariable) domain of an anti-IL-8 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$ and Fv), so long as they exhibit the desired biological activity. (See, e.g., Cabilly et al., U.S. Pat. No. 4,816,567; Mage and Lamoyi, in *Monoclonal Antibody Production Techniques and Applications,* pp. 79–97 (Marcel Dekker, Inc., New York, 1987).)

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler and Milstein, *Nature* 256:495 (1975), or can be made by recombinant DNA methods (Cabilly et al., supra).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. U.S.A.* 81:6851 (1984)).

"Humanized" forms of non-human (e.g., murine) antibodies are specific chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., *Nature* 321:522 (1986); Reichmann et al., *Nature* 332:323 (1988); and Presta, *Curr. Op. Struct. Biol.* 2:593 (1992).

The term "IL-8 antagonist" as used herein denotes a compound capable of disrupting or blocking the interaction between IL-8 and IL-8 receptor. IL-8 antagonists include anti-IL-8 antibodies and fragments thereof, IL-8-binding peptides and nonproteinaceous small molecules capable of binding to IL-8 or competing with IL-8 for binding to IL-8 receptor.

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

As used herein, protein, peptide and polypeptide are used interchangeably to denote an amino acid polymer or a set of two or more interacting or bound amino acid polymers.

As used herein, the term "inflammatory disorders" refers to pathological states resulting in inflammation, typically caused by neutrophil chemotaxis. Examples of such disorders include inflammatory skin diseases including psoriasis; responses associated with inflammatory bowel disease (such as Crohn's disease and ulcerative colitis); ischemic reperfusion; adult respiratory distress syndrome; dermatitis; meningitis; encephalitis; uveitis; autoimmune diseases such as rheumatoid arthritis, Sjorgen's syndrome, vasculitis; diseases involving leukocyte diapedesis; central nervous system (CNS) inflammatory disorder, multiple organ injury syndrome secondary to septicaemia or trauma; alcoholic hepatitis, bacterial pneumonia, antigen-antibody complex mediated diseases; inflammations of the lung, including pleurisy, alveolitis, vasculitis, pneumonia, chronic bronchitis, bronchiectasis, and cystic fibrosis; etc. The preferred indications are bacterial pneumonia and inflammatory bowel disease such as ulcerative colitis.

As used herein, the terms "asthma", "asthmatic disorder", "asthmatic disease", and "bronchial asthma" refer to a condition of the lungs in which there is widespread narrowing of lower airways. "Atopic asthma" and "allergic asthma" refer to asthma that is a manifestation of an IgE-mediated hypersensitivity reaction in the lower airways, including, e.g., moderate or severe chronic asthma, such as conditions requiring the frequent or constant use of inhaled or systemic steroids to control the asthma symptoms. A preferred indication is allergic asthma.

B. MODES FOR CARRYING OUT THE INVENTION

I. IL-8 Antagonist Preparation

The methods of the present invention can be practiced with any IL-8 antagonist that is capable of inhibiting or blocking IL-8 binding to neutrophils. Preferably, the IL-8 antagonist is capable of inhibiting neutrophil chemotaxis in response to IL-8 and/or capable of inhibiting the IL-8 mediated elastase release of neutrophils. IL-8 antagonists suitable for use herein include anti-IL-8 antibodies, IL-8 binding peptides, and nonproteinaceous small molecules capable of disrupting or blocking the interaction between IL-8 and its receptors. Candidate IL-8 antagonists can be tested for inhibition of IL-8 binding to neutrophils, inhibition of IL-8 mediated neutrophil chemotaxis, and inhibition of IL-8 mediated neutrophil elastase release as follows.

1. Inhibition of IL-8 binding to neutrophils

Preferably, the candidate IL-8 antagonist is tested for the ability to inhibit IL-8 binding to neutrophils of the same mammal species as that of the patient intended for IL-8 antagonist therapy. In one embodiment, neutrophils obtained from the patient are used to test candidate IL-8 antagonists, enabling the physician to identify the agents with greatest therapeutic efficacy for the particular patient. However, the invention also encompasses the use of neutrophils obtained from a species of mammal other than that of the intended patient for assessing the therapeutic potential of a candidate IL-8 antagonist. Neutrophils can be separated from red cells and mononuclear cells by sedimentation of whole blood in 1.5% Dextran T500 (Pharmacia, Sweden), layering the supernatant on a Lymphocyte Separation Medium (Organon Teknika, Durham, N.C.) and centrifuging according to the manufacturer's directions, recovering the cell pellet, and then subjecting the cell pellet to 2 or 3 cycles of hypotonic lysis. Alternatively, neutrophils can be separated from red blood cells and peripheral blood mononuclear cells by laying whole blood samples on Mono-Poly Resolving Medium (M-PRM) (Flow Laboratories, McLean, Va.) and recovering the neutrophil band according to the vendor's directions.

Similarly, it is preferable to use IL-8 from the same mammal species as that of the intended patient in testing a candidate IL-8 antagonist's ability to inhibit IL-8 binding to neutrophils. However, it is within the scope of the invention to use IL-8 derived from any mammalian species provided that the IL-8 binds to the neutrophils selected for testing with the candidate IL-8 antagonist. Preferably, the IL-8 and neutrophils used for testing are derived from the same mammalian species.

IL-8 can be isolated in vitro from endothelial cells or activated T cells and monocytes derived from the species of interest. IL-8 can be conveniently harvested from endothelial cells according to the method of Gimbrone et al., Science, 246: 1601 (1989) or from activated T cells and monocytes according to the method of Lindley et al., Proc. Natl. Acad. Sci., 85: 9199 (1988).

If the amino acid sequence of the particular IL-8 species is known, such as the amino acid sequence of human IL-8 (disclosed in Walz et al., Biochem. Biophys. Res. Comm., 149: 755–761 (1987); Yoshimura et al., Proc. Natl. Acad. Sci. USA, 84: 9233–9237 (1987); Van Damme et al., J. Exp. Med., 167: 1364–1376 (1988); Gregory et al., Biochem. Biophys. Res. Comm., 151: 883–890 (1988)), the IL-8 species of interest can be chemically synthesized, e.g., by using the solid phase synthesis method described by Merrifield, Science, 232: 342–347 (1986). In this method, a growing polypeptide chain is covalently anchored, usually by its C-terminus, to an insoluble solid support such as beads of polystyrene resin, and the appropriately blocked amino acids and reagents are added in the proper sequence This permits the quantitative recovery of the desired IL-8 product by simply filtering and washing the beads.

Alternatively, the IL-8 species of interest is produced by recombinant techniques. Recombinant IL-8 can be obtained by isolating or synthesizing DNA encoding the desired IL-8, cloning the IL-8 encoding DNA into an appropriate expression vector, transfecting a suitable expression host cell with the recombinant vector, selecting or detecting recombinant host cells, and growing the recombinant host cells under conditions permitting expression of IL-8 and harvesting the IL-8 produced thereby. In a preferred embodiment, recombinant human IL-8 is obtained as described in Hebert et al., J. Immunol., 145: 3033–3040 (1990).

Commercially available IL-8 species are also suitable for use herein. For example, recombinant human IL-8 can be purchased from R&D Systems, Minneapolis, Minn. (catalog no. 208-IL in the 1995 Catalog).

Any method for assaying IL-8 binding to neutrophils can be used to test a candidate IL-8 antagonist. Suitable assays include competitive binding assays wherein IL-8 binding to neutrophils is measured in the presence and absence of the candidate IL-8 antagonist. The IL-8 binding can be conveniently detected with the use of labelled IL-8, e.g., radiolabels, fluorochrome labels, enzyme labels, spin labels, etc., or with labelled anti-IL-8 antibodies. In a typical IL-8 competitive binding assay, the neutrophils are suspended in an appropriate buffer solution containing various concentrations of the candidate IL-8 antagonist, the labelled IL-8 is admixed to the cell suspension, the mixture is incubated under conditions allowing IL-8 to bind to neutrophils for a period of time sufficient for the competitive binding reaction to reach equilibrium, unbound labelled IL-8 is removed by centrifuging or filtering the cell suspension, and labelled IL-8 bound to neutrophils is quantitated by detection of the label, e.g., scintillation counting for radiolabels, addition of chromogenic substrate and spectrophotometric assay for chromogenic enzyme labels, flow-activated cell sorting for fluorochrome labels, etc.

In a preferred embodiment, the candidate IL-8 antagonist is screened for inhibition of human IL-8 binding to human neutrophils as described in the Examples below.

The percentage of IL-8 binding inhibition at a particular concentration of candidate IL-8 antagonist can be calculated with the quotient formed by division of the amount of labelled IL-8 specifically binding to neutrophils in the presence of the agent with the total amount of labelled IL-8 specifically binding to neutrophils in the absence of the agent. Labelled IL-8 specific binding amounts can be determined by subtracting the amount of labelled non-specific binding from the total amount of labelled IL-8 binding. The amount of labelled IL-8 non-specific binding can be determined by measuring labelled IL-8 binding in the presence of an excess of unlabelled IL-8. The concentration of candidate IL-8 antagonist necessary for 50%inhibition of IL-8 binding ($IC_{50}$) is determined using the inhibition percentages for the various concentrations of agent tested.

An agent is scored as positive for inhibition of IL-8 binding to neutrophils if a concentration of the agent of about 100 nanomoles/liter (nM) or lower, and preferably 1 nM or lower, and more preferably 10 picomoles/liter (pM) or lower, in the presence of an IL-8 concentration of about 0.5 nM produces decreased IL-8 binding to neutrophils in comparison to a control sample containing the same IL-8 concentration in the absence of the agent. Preferably, the candidate IL-8 antagonist is capable of inhibiting human IL-8 binding to human neutrophils with an $IC_{50}$ of about 50 nM or less, and preferably an average $IC_{50}$ of about 7.5 nM or less, and more preferably an average $IC_{50}$ of about 1.6 nM or less, in the presence of human IL-8 at a concentration of about 0.5 nM.

2. Inhibition of IL-8 mediated neutrophil chemotaxis

Preferably, the candidate IL-8 antagonist is also tested for the ability to inhibit neutrophil chemotaxis in response to IL-8. It is desirable to test the candidate IL-8 antagonist for the ability to inhibit IL-8 mediated chemotaxis of neutrophils derived from the same mammal species as that of the patient intended for IL-8 antagonist therapy. In one embodiment, neutrophils obtained from the patient are used to test candidate IL-8 antagonists, enabling the physician to identify the agents with greatest therapeutic efficacy for the particular patient. However, the invention also encompasses the use of neutrophils obtained from a species of mammal other than that of the intended patient for assessing the therapeutic potential of a candidate IL-8 antagonist.

Similarly, it is preferable to use IL-8 from the same mammal species as that of the intended patient in testing a candidate IL-8 antagonist's ability to inhibit IL-8 mediated neutrophil chemotaxis. However, it is within the scope of the invention to use IL-8 derived from any mammalian species provided that the IL-8 elicits chemotaxis of the neutrophils selected for testing with the candidate IL-8 antagonist. Preferably, the IL-8 and neutrophils used for testing are derived from the same mammalian species.

In one aspect, a candidate IL-8 antagonist is tested for inhibition of IL-8 mediated neutrophil chemotaxis using a 96 well microtiter chemotaxis apparatus (Neuro Probe, Cabin John, Md.) wherein each well is horizontally divided into two chambers by a 5 micron filter. A sample of the desired IL-8 is obtained as described in Section 1 above, combined with a particular concentration of the candidate IL-8 antagonist, and then placed in the bottom chamber of the chemotaxis apparatus. A sample of the desired neutrophils is obtained as described in Section 1 above and the cells are labelled with the fluorescent dye calcein AM (Molecular Probe, Eugene, Oreg.). The cells are washed, resuspended in an appropriate buffer, is counted and placed in the top chamber of the chemotaxis apparatus. The chemotaxis apparatus is incubated under conditions permitting IL-8 to diffuse into the neutrophil loading (top) chamber for a period of time sufficient to elicit neutrophil migration into the adjoining chamber. After incubation, cells remaining in the neutrophil loading (top) chamber are removed by aspiration and the top chamber side of the filter is washed and scraped to remove non-migrating cells. Labelled neutrophils in the bottom chamber and on the bottom chamber side of the filter are then quantitated for analysis.

In a preferred embodiment, the candidate IL-8 antagonist is assayed for inhibition of human neutrophil chemotaxis in response to human IL-8 as described in the Examples below.

The relative number of migrating and non-migrating neutrophils in a sample containing IL-8 antagonist can be determined by comparison of the signal detected in the IL-8 antagonist sample with the signal detected in a sample containing IL-8 alone (providing the positive control for uninhibited IL-8 induced migration) and the signal detected in a sample containing buffer alone (providing the negative control for background migration). An agent is scored as positive for inhibition of IL-8 mediated neutrophil migration if a concentration of the agent of about 100 nM or lower, and preferably 1 nM or lower, and more preferably 10 pM or lower, in the presence of an initial IL-8 concentration of about 2 nM produces decreased neutrophil migration in comparison to a control sample containing the same IL-8 concentration in the absence of the agent. Preferably, the candidate IL-8 antagonist inhibits 50% of human neutrophil migration at a concentration of about 6.0 nM or less, and more preferably at a concentration of about 3.0 nM or less, in the presence of an initial human IL-8 concentration of about 4 nM.

3. Inhibition of IL-8 mediated neutrophil elastase release

Preferably, the candidate IL-8 antagonist is further tested for the ability to inhibit neutrophil elastase release in response to IL-8. It is desirable to test the candidate IL-8 antagonist for the ability to inhibit IL-8 mediated elastase release of neutrophils derived from the same mammal species as that of the patient intended for IL-8 antagonist therapy. In one embodiment, neutrophils obtained from the patient are used to test candidate IL-8 antagonists, enabling the physician to identify the agents with greatest therapeutic efficacy for the particular patient. However, the invention also encompasses the use of neutrophils obtained from a species of mammal other than that of the intended patient for assessing the therapeutic potential of a candidate IL-8 antagonist.

Similarly, it is preferable to use IL-8 from the same mammal species as that of the intended patient in testing a candidate IL-8 antagonist's ability to inhibit IL-8 mediated neutrophil release of elastase. However, it is within the scope of the invention to use IL-8 derived from any mammalian species provided that the IL-8 induces elastase release in the neutrophils selected for testing with the candidate IL-8 antagonist. Preferably, the IL-8 and neutrophils used for testing are derived from the same mammalian species.

In non-stimulated neutrophils, IL-8 does not trigger the release of azurophil granules. In the presence of cytochalasin B, IL-8 causes degranulation of the azurophil granules and release of elastase. Thus, the ability of a candidate IL-8 antagonist to inhibit neutrophil elastase release in response to IL-8 can be determined by obtaining the desired neutrophils and IL-8 as described in Section 1 above, incubating the neutrophils in suspension with cytochalasin B, incubating the cytochalasin B-primed neutrophils with IL-8 in the presence or absence of the candidate IL-8 antagonist, centrifuging the cell suspension to remove the cells, incubating the cell-free supernatants with the elastase substrate methoxysuccinyl-alanyl-alanyl-prolyl-valyl-p-nitroanilide, and detecting the presence of p-nitroaniline in the test samples by spectrophotometric analysis at a wavelength of 405 nanometers (nm).

In a preferred embodiment, the candidate IL-8 antagonist is assayed for inhibition of human neutrophil elastase release in response to human IL-8 as described in the Examples below.

The inhibition percentage of IL-8 mediated neutrophil elastase release at a particular concentration of candidate IL-8 antagonist can be calculated with the quotient formed by dividing the 405 nm fluorescence detected in the candidate IL-8 antagonist treated sample's supernatant by the 405 nm fluorescence detected in the IL-8 treated control sample's supernatant. An agent is scored as positive for inhibition of IL-8 mediated neutrophil elastase release if a concentration of the agent of about 10 micromoles/liter ($\mu$M) or lower, and preferably 100 nM or lower, and more preferably 1 nM or lower, in the presence of an IL-8 concentration of about 100 nM produces decreased neutrophil elastase release in comparison to a control sample for the same IL-8 concentration in the absence of the agent. Preferably, the candidate IL-8 antagonist inhibits 50% of human neutrophil elastase release induced by human IL-8 at a candidate IL-8 antagonist:human IL-8 molar ratio of about 1.0 or less, and more preferably about 0.65 or less.

II. Anti-IL-8 antibody preparation

1. Monoclonal antibodies

The anti-IL-8 antibodies of the invention are preferably monoclonal, binding IL-8 with a dissociation constant ($K_d$) of about $1 \times 10^{-8}$ to $1 \times 10^{-11}$, more preferably, $1 \times 10^{-9}$ to $1 \times 10^{-10}$. The antibodies of the invention preferably do not measurably bind in an enzyme-linked immunoabsorbent assay (ELISA) to chemokines other than IL-8, such as C5a, platelet factor 4 or $\beta$-TG. Furthermore, the antibodies of the invention preferably inhibit elastase release from IL-8 stimulated neutrophils and inhibit IL-8 stimulated chemotaxis of neutrophils. In one embodiment of the invention, the antibodies of the invention can bind IL-8 from non-human species in addition to human IL-8, such as rabbit IL-8.

In another embodiment of the invention, Fab, Fab', Fab'-SH, or F(ab')$_2$ fragments of the anti-IL-8 antibodies of the instant invention are created. These antibody "fragments" can be created by traditional means, such as enzymatic digestion, or may be generated by recombinant techniques. Such antibody fragments may be chimeric or humanized. These fragments are useful for the diagnostic and therapeutic purposed set forth below.

The anti-IL-8 monoclonal antibodies of the invention can be made, for example, using the hybridoma method first described by Kohler and Milstein, *Nature* 256:495 (1975), or can be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the IL-8 or IL-8 fragment used for immunization. Antibodies to IL-8 generally are raised in animals by multiple subcutaneous (sc) or intraperitoneal (ip) injections of the IL-8 and an adjuvant. Animals ordinarily are immunized against immunogenic conjugates or derivatives of IL-8 with monophosphoryl lipid A (MPL)/trehalose dicorynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-IL-8 titer. Animals are boosted until the titer plateaus.

Alternatively, lymphocytes can be immunized in vitro. Lymphocytes then are fused with myeloma cells using a suitable fusing agent, such as polyethylene glycol, to form a hybridoma cell (Goding, *Monoclonal Antibodies: Principles and Practice* pp. 59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium) which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. U.S.A., and SP-2 cells available from the American Type Culture Collection, Rockville, Md. U.S.A.

Culture medium in which hybridoma cells are growing is assayed for production of monoclonal antibodies directed against IL-8. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the mAbs can, for example, be determined by the Scatchard analysis of Munson and Pollard, *Anal. Biochem.* 107:220 (1980).

After hybridoma cells are identified that produce antibodies of the desired specificity, affinity, and/or activity, the clones can be subcloned by limiting dilution procedures and grown by standard methods (Goding, supra). Suitable culture media for this purpose include, for example, D-MEM or RPMI-1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.* 5:256 (1993) and Plückthun *Immunol. Revs.* 130:151 (1992).

The DNA also can be modified, for example, by substituting the coding sequence for human heavy- and light-chain constant domains in place of the homologous murine sequences (e.g., Morrison et al., *Proc. Natl. Acad. Sci.* 81:6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of an anti-IL-8 mAb herein.

Typically, such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a IL-8 and another antigen-combining site having specificity for a different antigen.

Chimeric or hybrid antibodies also can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate.

2. Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.* 151: 2296 (1993); Chothia and Lesk, *J. Mol. Biol.* 196:901 (1987)). Another method uses a particular framework derived from the consensus sequence of all human antibodies of a particular subgroup of light or heavy chains. The same framework can be used for several different humanized antibodies (Carter et al., *Proc. Natl. Acad. Sci. U.S.A.* 89:4285 (1992); Presta et al., *J. Immunol.* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

3. Human antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133:3001 (1984); Brodeur et al., *Monoclonal Antibody Production Techniques and Applications*, pp. 51–63 (Marcel Dekker, Inc., New York, 1987); and Boerner et al., *J. Immunol.* 147:86 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. U.S.A.* 90:2551 (1993); Jakobovits et al. *Nature* 362:255 (1993); Bruggermann et al., *Year in Immuno.* 7:33 (1993).

Alternatively, phage display technology (McCafferty et al., *Nature* 348:552 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson et al., *Current Opinion in Structural Biology* 3:564 (1993). Several sources of V-gene segments can be used for phage display. Clackson et al., *Nature* 352:624 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581 (1991), or Griffith et al., *EMBO J.* 12:725 (1993).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10:779 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., *Nucl. Acids Res.* 21:2265 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection with antigen results in isolation of human variable capable of restoring a functional antigen-binding site, i.e. the epitope governs (imprints) the choice of partner. When the process is repeated in order to replace the remaining rodent V domain, a human antibody is obtained (see PCT WO 93/06213, published 1 April 1993). Unlike traditional humanization of rodent antibodies by CDR grafting, this technique provides completely human antibodies, which have no framework or CDR residues of rodent origin.

4. Bispecific antibodies

Bispecific antibodies are monoclonal, preferably human or humanized, antibodies that have binding specificities for at least two different antigens. In the present case, one of the binding specificities is for IL-8, the other one is for any other antigen. For example, bispecific antibodies specifically binding a IL-8 and neurotrophic factor, or two different types of IL-8 polypeptides are within the scope of the present invention.

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature* 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published 13 May 1993, and in Traunecker et al., *EMBO J.* 10:3655 (1991).

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, the second heavy chain constant region ($C_H2$), and the third heavy chain constant region ($C_H3$). It is preferred to have the first heavy-chain constant region ($C_H1$), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. For further details of generating bispecific antibodies, see, for example, Suresh et al., *Methods in Enzymology* 121:210 (1986).

5. Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/00373; and EP 03089). Heteroconjugate antibodies can be made using any convenient cross-linking methods. Suitable cross-linking agents are well known in the art, and are disclosed in U.S. Pat. No. 4,676,980, along with a number of cross-linking techniques.

III. Diagnostic uses of anti-IL-8 antibodies

For diagnostic applications requiring the detection or quantitation of IL-8, the antibodies of the invention typically will be labeled with a detectable moiety. The detectable moiety can be any one which is capable of producing, either directly or indirectly, a detectable signal. For example, the detectable moiety can be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the antibody to the detectable moiety can be employed, 5 including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

The antibodies of the present invention can be employed in any known assay method, such as competitive binding assays, direct and indirect sandwich assays, and immunoprecipitation assays. For example, see Zola, *Monoclonal Antibodies: A Manual of Techniques*, pp. 147–158 (CRC Press, Inc., 1987).

Competitive binding assays rely on the ability of a labeled standard (which can be a IL-8 or an immunologically reactive portion thereof) to compete with the test sample analyte (IL-8) for binding with a limited amount of antibody. The amount of IL-8 in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies can conveniently be separated from the standard and analyte which remain unbound.

Sandwich assays involve the use of two antibodies, each capable of binding to a different antigenic portion, or epitope, of the protein (IL-8) to be detected. In a sandwich assay, the test sample analyte is bound by a first antibody which is immobilized on a solid support, and thereafter a second antibody binds to the analyte, thus forming an insoluble three-part complex (U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme (e.g., horseradish peroxidase).

IL-8 antibodies also are useful for the affinity purification of IL-8 from recombinant cell culture or natural sources. For example, these antibodies can be fixed to a solid support by techniques well known in the art so as to purify IL-8 from a source such as culture supernatant or tissue.

IV. Therapeutic compositions and administration of IL-8 antagonist

Therapeutic formulations of IL-8 antagonist are prepared for storage by IL-8 antagonist having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The IL-8 antagonist to be used for in vivo administration must be sterile. This is readily accomplished by filtration through sterile filtration membranes; prior to or following lyophilization and reconstitution. The IL-8 antagonist ordinarily will be stored in lyophilized form or in solution.

Therapeutic IL-8 antagonist compositions generally are placed into a container having a sterile access port, for example, an intravenous solution bag or vial having a stopper pierceable by a hypodermic injection needle.

The route of IL-8 antagonist administration is in accord with known methods, e.g., inhalation, injection or infusion by intravenous, intraperitoneal, intracerebral, intramuscular intraocular, intraarterial, or intralesional routes, by enema or suppository, or by sustained release systems.

In one embodiment, the invention provides for the treatment of asthmatic diseases by administration of IL-8 antagonist to the respiratory tract. The invention contemplates formulations comprising an IL-8 antagonist for use in a wide variety of devices that are designed for the delivery of pharmaceutical compositions and therapeutic formulations to the respiratory tract. In one aspect of the present invention, an IL-8 antagonist is administered in aerosolized or inhaled form. The IL-8 antagonist, combined with a dispersing agent, or dispersant, can be administered in an aerosol formulation as a dry powder or in a solution or suspension with a diluent.

Suitable dispersing agents are well known in the art, and include but are not limited to surfactants and the like. Surfactants are generally used in the art to reduce surface induced aggregation of protein caused by atomization of the solution forming the liquid aerosol. Examples of such surfactants include polyoxyethylene fatty acid esters and alcohols, and polyoxyethylene sorbitan fatty acid esters. Amounts of surfactants used will vary, being generally within the range of about 0.001 to 4% by weight of the formulation. In a specific aspect, the surfactant is polyoxyethylene sorbitan monooleate or sorbitan trioleate.

The liquid aerosol formulations contain the IL-8 antagonist and a dispersing agent in a physiologically acceptable diluent. The dry powder aerosol formulations of the present invention consist of a finely divided solid form of the IL-8 antagonist and a dispersing agent, and optionally a bulking agent, such as lactose, sorbitol, sucrose, or mannitol, and the like, to facilitate dispersal of the powder. With either the liquid or dry powder aerosol formulation, the formulation must be aerosolized. That is, it must be broken down into liquid or solid particles in order to ensure that the aerosolized dose actually reaches the bronchii and/or alveoli, as desired. For example, in the methods for treatment of asthma provided herein, it is preferable to deliver aerosolized IL-8 antagonist to the bronchii. In other embodiments, such as the present methods for treating adult respiratory distress syndrome, it is preferably to deliver aerosolized IL-8 antagonist to the alveoli. In general the mass median dynamic diameter will be 5 micrometers ($\mu$m) or less in order to ensure that the drug particles reach the lung bronchii or alveoli (Wearley, L. L., 1991, 1991, Crit. Rev. in Ther. Drug Carrier Systems 8:333).

With regard to construction of the delivery device, any form of aerosolization known in the art, including but not limited to nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellent. The propellent can be any propellant generally used in the art. Examples of useful propellants include chlorofluorocarbons, hydrofluorocarbons, hydochlorofluorocarbons, and hydrocarbons, including triflouromethane, dichlorodifluoromethane, dichlorotetrafluoroethanol, and 1,1,1,2-tetrafluoroethane, and combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation.

Systems of aerosol delivery, such as the pressurized 15 metered dose inhaler and the dry powder inhaler are disclosed in Newman, S. P., *Aerosols and the Lung,* Clarke, S. W. and Davia, D. editors, pp. 197–22 and can be used in connection with the present invention.

Sustained release systems can be used in the practice of the methods of the invention. Suitable examples of sustained-release preparations include semipermeable polymer matrices in the form of shaped articles, e.g. films, or microcapsules. Sustained release matrices include polyesters, hydrogels, polylactides (U.S. Pat No. 3,773,919, EP 58,481), copolymers of L-glutamic acid and gamma ethyl-L-glutamate (Sidman et al., *Biopolymers* 22:547 (1983)), poly (2-hydroxyethyl-methacrylate) (Langer et al., *J. Biomed. Mater. Res.* 15:167 (1981) and Langer, *Chem. Tech.* 12:98 (1982)), ethylene vinyl acetate (Langer et al., supra) or poly-D-(−)-3-hydroxybutyric acid (EP 30 133, 988). Sustained-release IL-8 antagonist compositions also include liposomally entrapped IL-8 antagonist. Liposomes containing IL-8 antagonist are prepared by methods known per se: DE 3,218,121; Epstein et al., *Proc. Natl. Acad. Sci. U.S.A.* 82:3688 (1985); Hwang et al., *Proc. Natl. Acad. Sci. U.S.A.* 77:4030 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mole percent cholesterol, the selected proportion being adjusted for the optimal IL-8 antagonist therapy.

An "effective amount" of IL-8 antagonist to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the IL-8 antagonist until a dosage is reached that achieves the desired effect. The progress of this therapy is easily monitored by conventional assays.

In the treatment and prevention of an inflammatory disorder or asthmatic disorder with an IL-8 antagonist, the IL-8 antagonist composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the IL-8 antagonist, the particular type of IL-8 antagonist, the method of administration, the scheduling of administration, and other factors known to medical practitioners. The "therapeutically effective amount" of antibody to be administered will be governed by such considerations, and is the minimum amount necessary to prevent, ameliorate, or treat the disorder, including treating acute or chronic respiratory diseases and reducing inflammatory responses. Such amount is preferably below the amount that is toxic to the host or renders the host significantly more susceptible to infections.

As a general proposition, the initial pharmaceutically effective amount of the IL-8 antagonist administered parenterally per dose will be in the range of about 0.1 to 50 milligrams per kilogram of patient body weight per day (mg/kg/day), with the typical initial range of IL-8 antagonist used being 0.3 to 20 mg/kg/day, more preferably 0.3 to 15 mg/kg/day.

In one embodiment using systemic administration, the initial pharmaceutically effective amount will be in the range of about 2 to 5 mg/kg/day.

For methods of the invention using administration by inhalation, the initial pharmaceutically effective amount will be in the range of about 1 microgram ($\mu$g)/kg/day to 100 mg/kg/day for an antibody agent, and about 1 $\mu$g/kg/day to 20 mg/kg/day for a small molecule agent.

The invention provides for both prophylactic and therapeutic treatment of asthma with IL-8 antagonists. In the case of prophylactic treatment for allergic asthma with an anti-IL-8 antibody, it is desirable to administer about 0.1 to 10 mg/kg of the antibody agent to the patient up to about 24 hours prior to anticipated exposure to allergen or prior to the onset of allergic asthma. In the case of therapeutic treatment for acute asthma, including allergic asthma, it is desirable to treat the asthmatic patient as early as possible following onset of an asthma attack. In one embodiment, an episode of acute asthma is treated within 24 hours of the onset of symptoms by administration of about 0.1 to 10 mg/kg of an anti-IL-8 antibody agent. However, it will be appreciated that the methods of the invention can be used to ameliorate symptoms at any point in the pathogenesis of asthmatic disease. Additionally, the methods of the invention can be used to alleviate symptoms of chronic asthmatic conditions.

As noted above; however, these suggested amounts of IL-8 antagonist are subject to a great deal of therapeutic discretion. The key factor in selecting an appropriate dose and scheduling is the result obtained, as indicated above.

The IL-8 antagonist need not be; but is optionally formulated with one or more agents currently used to prevent or treat the inflammatory disorder or asthmatic disease in question. For example, in rheumatoid arthritis, the antibody can be given in conjunction with a glucocorticosteroid. In the case of treating asthmatic diseases with IL-8 antagonists, the invention contemplates the coadministration of IL-8 antagonist and one or more additional agents useful in treating asthma, such as bronchodilators, antihistamines, epinephrine, and the like. The effective amount of such other agents depends on the amount of IL-8 antagonist present in the formulation, the type of disorder or treatment, and other factors discussed above. These are generally used in the same dosages and with administration routes as used hereinbefore or about from 1 to 99% of the heretofore employed dosages.

The following examples are offered by way of illustration and not by way of limitation. The disclosures of all citations in the specification are expressly incorporated herein by reference.

EXAMPLES

A. GENERATION AND CHARACTERIZATION OF MONOCLONAL ANTIBODIES AGAINST HUMAN IL-8

Balb/c mice were immunized in each hind footpad or intraperitoneally with 10 micrograms ($\mu$g) of recombinant human IL-8 (produced as a fusion of (ser-IL-8)$_{72}$ with ubiquitin (Hebert et al. *J. Immunology* 145:3033–3040 (1990)); IL-8 is available commercially from PeproTech, Inc., Rocky Hill, N.J.) resuspended in MPL/TDM (Ribi Immunochem. Research Inc., Hamilton, Mont.) and boosted twice with the same amount of IL-8. In these experiments, "IL-8" is intended to mean (ser-IL-8)$_{72}$ unless otherwise specified. A final boost of 10 $\mu$g of IL-8 was given 3 days before the fusion. Spleen cells or popliteal lymph node cells were fused with mouse myeloma P3X63Ag8U.1 (ATCC CRL1597), a non-secreting clone of the myeloma P3X63Ag8, using 35% polyethylene glycol as described before. Ten days after the fusion, culture supernatant was screened for the presence of monoclonal antibodies to IL-8 by ELISA.

The ELISA was performed as follows. Nunc 96-well immunoplates (Flow mab, McLean, Va.) were coated with 50 microliters ($\mu$l)/well of 2 micrograms/milliliter ($\mu$g/ml) IL-8 in phosphate-buffered saline (PBS) overnight at 4° C. The remaining steps were carried out at room temperature. Nonspecific binding sites were blocked with 0.5% bovine serum albumin (BSA) for 1 hour (hr). Plates were then incubated with 50 μl/well of hybridoma culture supernatants from 672 growing parental fusion wells for 1 hr, followed by the incubation with 50 μl/well of 1:1000 dilution of a 1 milligram/milliliter (mg/ml) stock solution of alkaline phosphatase-conjugated goat anti-mouse Ig (Tago Co., Foster City, Calif.) for 1 hr. The level of enzyme-linked antibody bound to the plate was determined by the addition of 100 μl/well of 0.5 mg/ml of r-nitrophenyl phosphate in sodium bicarbonate buffer, pH 9.6. The color reaction was measured at 405 nm with an ELISA plate reader (Titertrek Multiscan, Flow Lab, McLean, Va.). Between each step, plates were washed three times in PBS containing 0.05% Tween 20.

Culture supernatants which promoted 4-fold more binding of IL-8 than did control medium were selected as positives. According to this criterion, 16 of 672 growing parental fusion wells (2%) were positive. These positive hybridoma cell lines were cloned at least twice by using the limiting dilution technique.

Seven of the positive hybridomas were further characterized as follows. The isotypes of the monoclonal antibodies were determined by coating Nunc 96-well immunoplates (Flow Lab, McLean, Va.) with IL-8 overnight, blocking with BSA, incubating with culture supernatants followed by the addition of predetermined amount of isotype-specific alkaline phosphatase-conjugated goat anti-mouse Ig (Fisher Biotech, Pittsburgh, Pa.). The level of conjugated antibodies bound to the plate was determined by the addition of r-nitrophenyl phosphate as described above.

All the monoclonal antibodies tested belonged to either $IgG_1$ or $IgG_2$ immunoglobulin isotype. Ascites fluid containing these monoclonal antibodies had antibody titers in the range of 10,000 to 100,000 as determined by the reciprocal of the dilution factor which gave 50% of the maximum binding in the ELISA.

To assess whether these monoclonal antibodies bound to the same epitopes, a competitive binding ELISA was performed. At a ratio of biotinylated mAb to unlabeled mAb of 1:100, the binding of biotinylated mAb 5.12.14 was significantly inhibited by its homologous mAb but not by mAb 4.1.3, while the binding of biotinylated mAb 4.1.3 was inhibited by mAb 4.1.3 but not by mAb 5.12.14. Monoclonal antibody 5.2.3 behaved similarly to mAb 4.1.3, while monoclonal antibodies 4.8 and 12.3.9 were similar to mAb 5.12.14. Thus, mAb 4.1.3 and mAb 5.2.3 bind to a different epitope(s) than the epitope recognized by monoclonal antibodies 12.3.9, 4.8 and 5.12.14.

Immunodot blot analysis was performed to assess antibody reactivity to IL-8 immobilized on nitrocellulose paper. All seven antibodies recognized IL-8 immobilized on paper, whereas a control mouse IgG antibody did not.

The ability of these monoclonal antibodies to capture soluble $^{125}$I-IL-8 was assessed by a radioimmune precipitation test (RIP). Briefly, tracer $^{125}$I-IL-8 ($4\times10^4$ counts per minute (cpm)) was incubated with various dilutions of the monoclonal anti-IL-8 antibodies in 0.2 ml of PBS containing 0.5% BSA and 0.05% Tween 20 (assay buffer) for 1 hr at room temperature. One hundred microliters of a predetermined concentration of goat anti-mouse Ig antisera (Pel-Freez, Rogers, Ark.) were added and the mixture was incubated at room temperature for 1 hr. Immune complexes were precipitated by the addition of 0.5 milliliters (ml) of 6% polyethylene glycol (molecular weight (M.W.) 8000) kept at 4° C. After centrifugation at 2,000×gravity (g) for 20 min at 4° C., the supernatant was removed by aspiration and the radioactivity remaining in the pellet was counted in a gamma counter. Percent specific binding was calculated as (precipitated cpm−background cpm)/(total cpm−background cpm). Monoclonal antibodies 4.1.3, 5.2.3, 4.8, 5.12.14 and 12.3.9 captured $^{125}$I-IL-8 very efficiently, while antibodies 9.2.4 and 8.9.1 were not able to capture soluble $^{125}$I-IL-8 in the RIP even though they could bind to IL-8 coated onto ELISA plates (Table I).

The dissociation constants of these monoclonal antibodies were determined using a competitive binding RIP assay. Briefly, competitive inhibition of the binding each antibody to $^{125}$I-IL-8 (20,000–40,000 cpm per assay ) by various amounts of unlabeled IL-8 was determined by the RIP described above. The dissociation constant (affinity)of each mAb was determined by using Scatchard plot analysis (Munson, et al., *Anal. Biochem.* 107:220 (1980)) as provided in the VersaTerm-PRO computer program (Synergy Software, Reading, Pa.). The dissociation constants ($K_d$'s) of these monoclonal antibodies (with the exception of 9.2.4. and 8.9.1) were in the range from $2\times10^{-8}$ to $3\times10^{-10}$ moles/liter (M). Monoclonal antibody 5.12.14 with a $K_d$ of $3\times10^{-10}$M showed the highest affinity among all the monoclonal antibodies tested (Table I).

TABLE I

Characterization of Anti-IL-8 Monoclonal Antibodies

| Antibody | % Specific Binding to IL-8 | $K_d$(M) | Isotype | isoelect. point(pI) |
|---|---|---|---|---|
| 4.1.3 | 58 | $2 \times 10^{-9}$ | $IgG_1$ | 4.3–6.1 |
| 5.2.3 | 34 | $2 \times 10^{-8}$ | $IgG_1$ | 5.2–5.6 |
| 9.2.4 | 1 | — | $IgG_1$ | 7.0–7.5 |
| 8.9.1 | 2 | — | $IgG_1$ | 6.8–7.6 |
| 4.8 | 62 | $3 \times 10^{-8}$ | $IgG_{2a}$ | 6.1–7.1 |
| 5.12.14 | 98 | $3 \times 10^{-10}$ | $IgG_{2a}$ | 6.2–7.4 |
| 12.3.9 | 86 | $2 \times 10^{-9}$ | $IgG_{2a}$ | 6.5–7.1 |

To assess the ability of these monoclonal antibodies to neutralize IL-8 activity, the amount of $^{125}$I-IL-8 bound to human neutrophils in the presence of various amounts of culture supernatants and purified monoclonal antibodies was measured. Neutrophils were prepared by using Mono-Poly Resolving Medium (M-PRM) (Flow Lab. Inc., McLean, Va.). Briefly fresh, heparinized human blood was loaded onto M-PRM at a ratio of blood to medium, 3.5:3.0, and centrifuged at 300×g for 30 min at room temperature. Neutrophils enriched at the middle layer were collected and washed once in PBS. Such a preparation routinely contained greater than 95% neutrophils according to the Wright's Giemsa staining. The receptor binding assay was done as follows. 50 microliters (μl) of $^{125}$I-IL-8 (5 nanograms/milliliter (ng/ml)) was incubated with 50 μl of unlabeled IL-8 (100 micrograms/milliliter (μg/ml)) or monoclonal antibodies in phosphate buffered saline (PBS) containing 0.1% bovine serum albumin (BSA) for 30 min at room temperature. The mixture was then incubated with 100 μl of neutrophils ($10^7$ cells/ml) for 15 min at 37° C. The $^{125}$I-IL-8 bound was separated from the unbound material by loading mixtures onto 0.4 ml of PBS containing 20% sucrose and 0.1% BSA and by centrifugation at 300×g for 15 min. The supernatant was removed by aspiration and the radioactivity associated with the pellet was counted in a gamma counter.

Monoclonal antibodies 4.1.3, 5.2.3, 4.8, 5.12.14, and 12.3.9 inhibited greater than 85% of the binding of IL-8 to human neutrophils at a 1:25 molar ratio of IL-8 to mAb. On the other hand, monoclonal antibodies 9.2.4 and 8.9.1 appeared to enhance the binding of IL-8 to its receptors on human neutrophils. Since a control mouse IgG also enhanced the binding of IL-8 on neutrophils, the enhancement of IL-8 binding to its receptors by mAb 9.2.4 and 8.9.1 appears to be nonspecific. Thus, monoclonal antibodies, 4.1.3, 5.1.3, 4.8, 5.12.14, and 12.3.9 are potential neutralizing monoclonal antibodies while monoclonal antibodies 8.9.1 and 9.2.4 are non-neutralizing monoclonal antibodies.

The ability of the anti-IL-8 antibodies to block neutrophil chemotaxis induced by IL-8 was tested as follows. Neutrophil chemotaxis induced by IL-8 was determined using a Boyden chamber method (Larsen, et al. *Science* 243:1464 (1989)). One hundred μl of human neutrophils ($10^6$ cells per milliliter (cells/ml)) resuspended in RPMI containing 0.1% BSA were placed in the upper chamber and 29 μl of the IL-8 (20 nM) with or without monoclonal antibodies were placed in the lower chamber. Cells were incubated for 1 hr at 37° C. Neutrophils migrated into the lower chamber were stained with Wright's Giemsa stain and counted under the microscope (100× magnification). Approximately 10 different fields per experimental group were examined. Neutralizing monoclonal antibodies 5.12.14 and 4.1.3 blocked almost 70% of the neutrophil chemotactic activity of IL-8 at 1:10 ratio of IL-8 to mAb.

The isoelectric focusing (IEF) pattern of each mAb was determined by applying purified antibodies on an IEF polyacrylamide gel (pH 3–9, Pharmacia) using the Fast gel system (Pharmacia, Piscataway, N.J.). The IEF gel was pretreated with pharmalyte containing 1%) Triton X100 (Sigma, St. Louis, Mo.) for 10 min before loading the samples. The IEF pattern was visualized by silver staining according to the instructions from the manufacturer. All of the monoclonal antibodies had different IEF patterns, confirming that they originated from different clones. The pI values for the antibodies are listed in Table I.

All these monoclonal antibodies bound equally well to both (ala-IL-8)77 and (ser-IL-8)72 forms of IL-8. Because IL-8 has greater than 30% sequence homology with certain other members of the platelet factor 4 (PF4) family of inflammatory cytokines such as β-TG (Van Damme et al., *Eur. J. Biochem.* 181:337(1989); Tanaka et al., *FEB* 236(2):467 (1988)) and PF4 (Deuel et al., *Proc. Natl. Acad. Sci. U.S.A.* 74:2256 (1977)), they were tested for possible cross reactivity to β-TG and PF4, as well as to another neutrophil activating factor, C5a. No detectable binding to any of these proteins was observed, with the exception of mAb 4.1.3, which had a slight cross reactivity to β-TG.

One of the antibodies, mAb 5.12.14, was further studied to determine whether it could block the IL-8 mediated release of elastase by neutrophils. Briefly, human neutrophils were resuspended in Hanks balanced salt solution (Gibco, Grand Island, N.Y.) containing 1.0% BSA, Fraction V (Sigma, St. Louis, Mo.), 2 mg/ml alpha-D-glucose (Sigma), 4.2 millimoles/liter (mM) sodium bicarbonate (Sigma) and 0.01M HEPES, pH 7.1 (JRH Bioscience, Lenexa, Kans.). A stock of cytochalasin B (Sigma) was prepared (5 mg/ml in dimethylsulfoxide (Sigma) and stored at 2°–8° C. Cytochalasin B was added to the neutrophil preparation to produce a final concentration of 5 μg/ml, and incubated for 15 min at 37° C. Human IL-8 was incubated with mAb 5.12.14 (20 μl), or a negative control antibody, in 1 ml polypropylene tubes (DBM Scientific, San Fernando, Calif.) for 30 min at 37° C. The final assay concentrations of IL-8 were 50 and 500 nM. The monoclonal antibodies were diluted to produce the following ratios (IL-8:Mab): 1:50, 1:10, 1:2, 1:1, and 1:0.25. Cytochalasin B-treated neutrophils were added (100 μl/tube) and incubated for 2 hours at 25° C. The tubes were centrifuged (210×g, 2°–8° C.) for 10 min, and supernatants were transferred to 96 well tissue culture plates (30 μl/well). Elastase substrate stock, 10 mM methoxysuccinyl-alanyl-alanyl-propyl-valyl-p-nitroanilide (Calbiochem, La Jolla, Calif.) in DMSO was prepared and stored at 2°–8° C. Elastase substrate solution (1.2 mM substrate, 1.2M NaCl (Mallinckrodt, Paris, Ky.), 0.12M HEPES pH 7.2 in distilled water) was added (170 μl/well) to the supernatants and incubated for 0.5 to 2 hours at 37° C. (until control optical density (O.D.) of 1.0 was reached). Absorbance was measured at 405 nm (SLT 340 ATTC plate reader, SLT Lab Instruments, Austria).

The results are shown in FIG. 1. At a 1:1 ratio of IL-8 to mAb 5.12.14, the antibody was able to effectively block the release of elastase from neutrophils.

The hybridoma producing antibody 5.12.14 was deposited on Feb. 15, 1993 with the American Type Culture Collection, 12301 Parklawn Drive, Rockville, Md., U.S.A. (ATCC) and assigned ATTC Accession No. HB 11553. This deposit was made under the provisions of the Budapest Treaty on the International Recognition of the Deposit of Microorganisms for the Purpose of Patent Procedure and the Regulations thereunder (Budapest Treaty).

B. GENERATION AND CHARACTERIZATION OF MONOCLONAL ANTIBODIES AGAINST RABBIT IL-8

Antibodies against rabbit IL-8 were generated in essentially the same process as anti-human IL-8 antibodies using rabbit IL-8 as immunogen (kindly provided by C. Broaddus; see also Yoshimura et al. *J. Immunol.* 146:3483 (1991)). The antibody was characterized as described above for binding to other cytokines coated onto ELISA plates; no measurable binding was found to MGSA, fMLP, C5a, b-TG, TNF, PF4, or IL-1.

The hybridoma producing antibody 6G4.2.5 was deposited on Sep. 28, 1994, with the American Type Culture Collection, 12301 Parklawn Drive, Rockville, Md., U.S.A. (ATCC) and assigned ATTC Accession No. HB 11722. This deposit was made under the provisions of the Budapest Treaty on the International Recognition of the Deposit of Microorganisms for the Purpose of Patent Procedure and the Regulations thereunder (Budapest Treaty).

Recombinant human-murine chimeric Fabs for 5.12.14 and 6G4.2.5 were constructed as described below. A chimeric 6G.4.25 Fab is compared with a chimeric 5.12.14 Fab in detail below.

I. inhibition of IL-8 binding to human neutrophils by 5.12.14-FAB and 6G4 2.5-FAB The ability of the two chimeric Fabs, 5.12.14-Fab and 6G4.2.5-Fab, to efficiently bind IL-8 and prevent IL-8 from binding to IL-8 receptors on human neutrophils was determined by performing a competition binding assay which allows the calculation of the $IC_{50}$-concentration required to achieve 50% inhibition of IL-8 binding.

Figure 2:
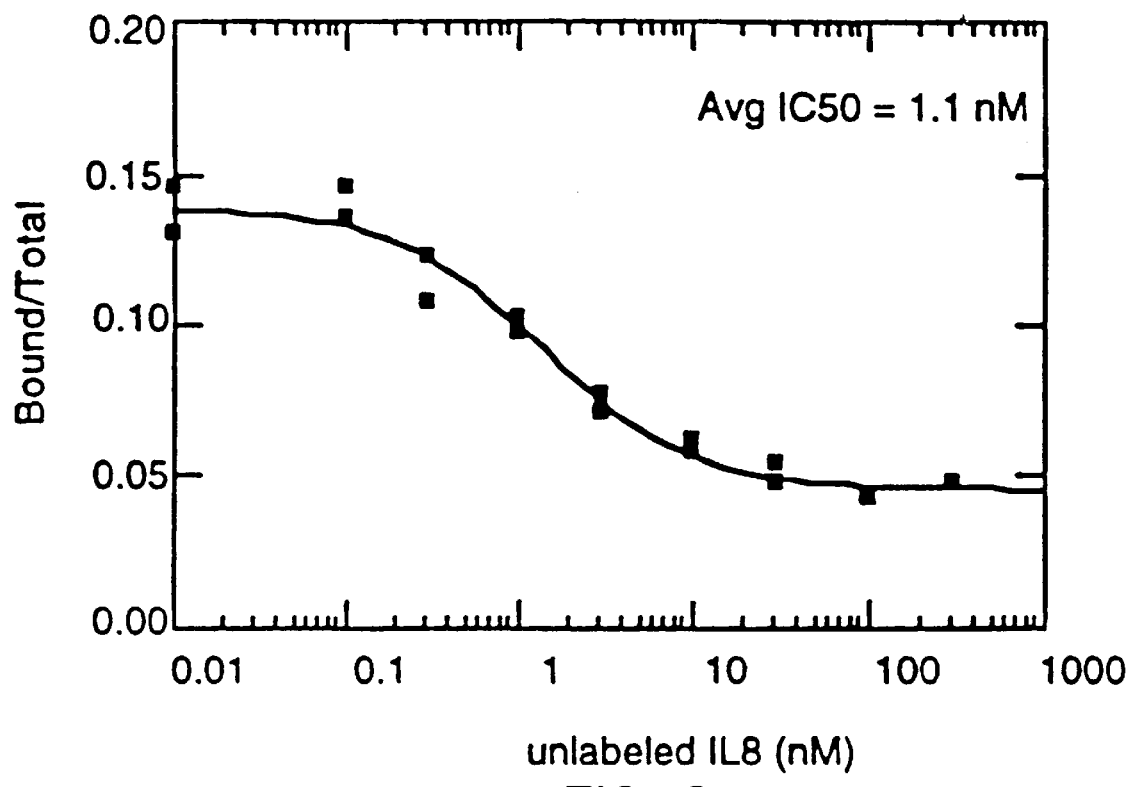
FIG. 2 is a graph depicting the inhibition of $^{125}$I-IL-8 binding to neutrophils by unlabeled IL-8.
Figure 3:
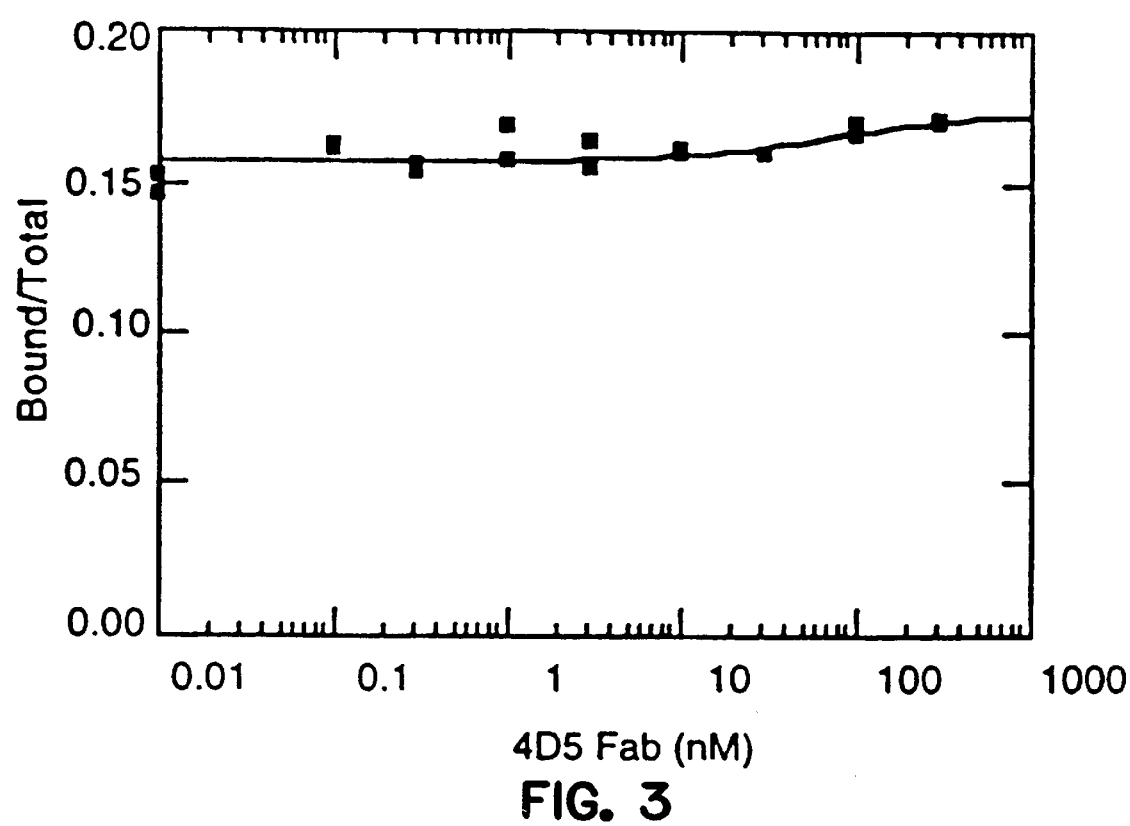
FIG. 3 demonstrates a negative isotype matched Fab does not inhibit the binding of $^{125}$I-IL-8 to human neutrophils.
Figure 4:
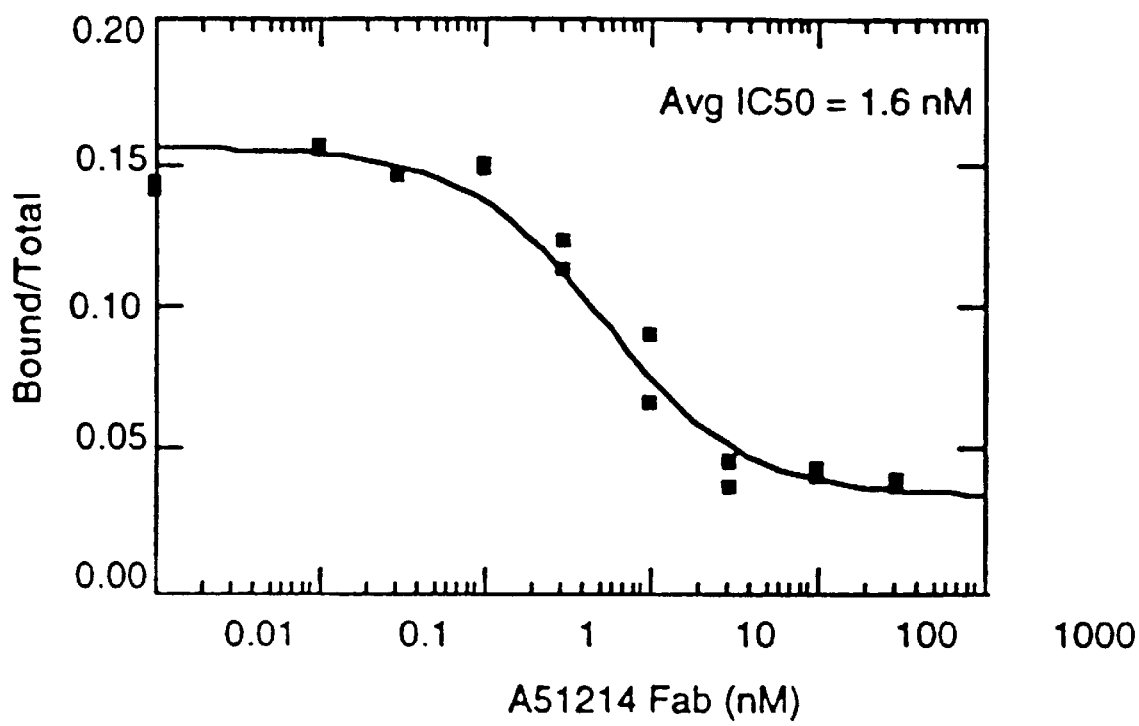
FIG. 4 is a graph depicting the inhibition of binding of $^{125}$I-IL-8 to human neutrophils by chimeric 5.12.14 Fab with an average $IC_{50}$ of 1.6 nanomoles/liter (nM).
Figure 5:
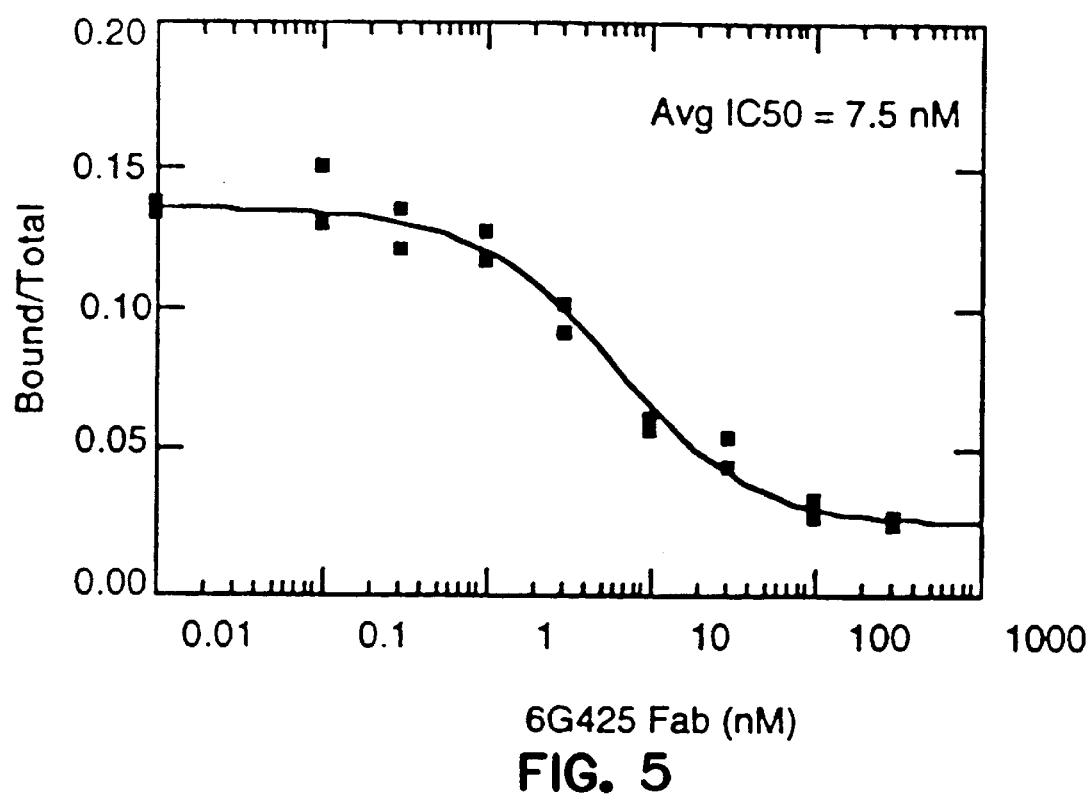
FIG. 5 is a graph depicting the inhibition of binding of $^{125}$I-IL-8 to human neutrophils by chimeric 6G.4.25 Fab with an average concentration required to achieve 50% inhibition of binding ($IC_{50}$) of 7.5 nM.

Human neutrophils ($5\times10^5$) were incubated for 1 hour at 4° C. with 0.5 nM $^{125}$I-IL-8 in the presence of various concentrations (0 to 300 nM) of 5.12.14-Fab, 6G4.2.5-Fab, an isotype control (4D5-Fab) or unlabeled IL-8. After the incubation, the unbound $^{125}$I-IL-8 was removed by centrifugation through a solution of 20% sucrose and 0.1% bovine serum albumin in phosphate buffered saline and the amount of $^{125}$-I-IL-8 bound to the cells was determined by counting the cell pellets in a gamma counter. FIG. 2 demonstrates the inhibition of $^{125}$-I-IL-8 binding to neutrophils by unlabeled IL-8. FIG. 3 demonstrates that a negative isotype matched Fab does not inhibit the binding of $^{125}$I-IL-8 to human neutrophils. Both the anti-IL-8 Fabs, 5.12.14 Fab (FIG. 4) and 6G.4.25 Fab (FIG. 5) were able to inhibit the binding of $^{125}$I-IL-8 to human neutrophils with an average $IC_{50}$ of 1.6 nM and 7.5 nM, respectively.

II. Inhibition of IL-a-mediated neutrophil chemotaxis by 5.12.14-FAB and 6G4.2.5-FAB Human neutrophils were isolated, counted and resuspended at $5 \times 10^6$ cells/ml in Hank's balanced salt solution (abbreviated HBSS; without calcium and magnesium) with 0.1% bovine serum albumin. The neutrophils were labeled by adding calcein AM (Molecular Probe, Eugene, Oreg.) at a final concentration of 2.0 micromoles/liter ($\mu$M). Following a 30 minute incubation at 37° C., cells were washed twice with HBSS-BSA and resuspended at $5 \times 10^6$ cells/ml.

Chemotaxis experiments were carried out in a Neuro Probe (Cabin John, Md.) 96-well chamber, model MBB96. Experimental samples (buffer only control, IL-8 alone or IL-8+Fabs) were loaded in a Polyfiltronics 96-well View plate (Neuro Probe Inc.) placed in the lower chamber. 100 $\mu$l of the calcein AM-labeled neutrophils were added to the upper chambers and allowed to migrate through a 5 micrometer porosity PVP free polycarbonate framed filter (Neuro Probe Inc.) toward the bottom chamber sample. The chemotaxis apparatus was then incubated for 40 to 60 minutes at 37° C. with 5% $CO_2$. At the end of the incubation, neutrophils remaining in the upper chamber were aspirated and upper chambers were washed three times with PBS. Then the polycarbonate filter was removed, non-migrating cells were wiped off with a squeegee wetted with PBS, and the filter was air dried for 15 minutes.

The relative number of neutrophils migrating through the filter (Neutrophil migration index) was determined by measuring fluorescence intensity of the filter and the fluorescence intensity of the contents of the lower chamber and adding the two values together. Fluorescence intensity was measured with a CytoFluor 2300 fluorescent plate reader (Millipore Corp. Bedford, Mass.) configured to read a Corning 96-well plate using the 485-20 nm excitation filter and a 530-25 emission filter, with the sensitivity set at 3.

Figure 6:
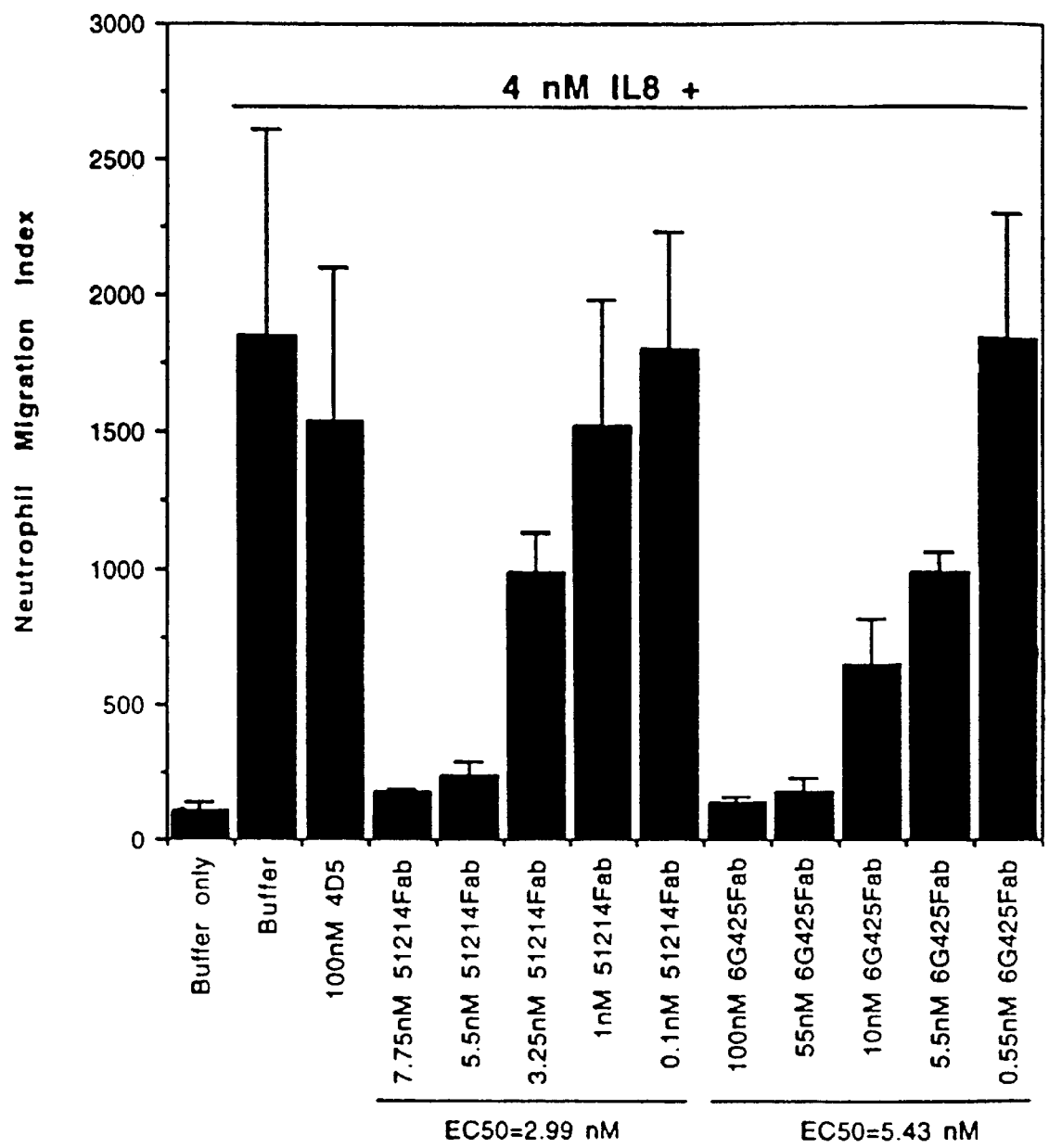
FIG. 6 demonstrates the inhibition of human IL-8 mediated neutrophil chemotaxis by chimeric 6G4.2.5 Fab and chimeric 5.12.14 Fab.
Figure 7:
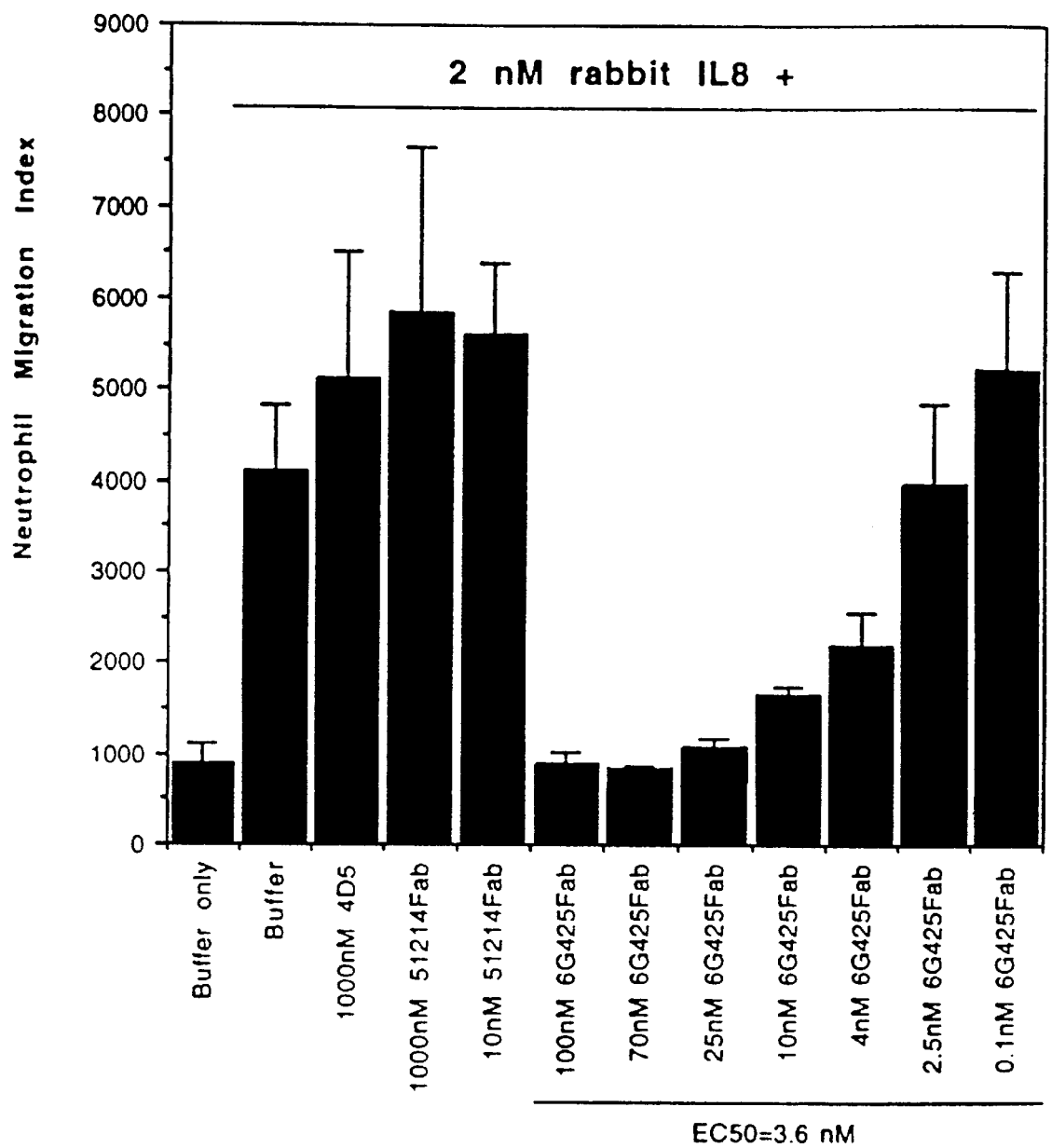
FIG. 7 demonstrates the relative abilities of chimeric 6G4.2.5 Fab and chimeric 5.12.14 Fab to inhibit rabbit IL-8 mediated neutrophil chemotaxis.

The results are shown in FIGS. 6 and 7. FIG. 6 demonstrates the inhibition of human IL-8 mediated neutrophil chemotaxis by chimeric 6G4.2.5 and 5.12.14 Fabs. FIG. 7 demonstrates the relative abilities of chimeric 6G4.2.5 and 5.12.14 Fabs to inhibit rabbit IL-8 mediated neutrophil chemotaxis.

III. Inhibition of IL-8-mediated neutrophil elastase release by various concentrations of 6G4.2.5 AND 5.12.14 FABS Blood was drawn from healthy male donors into heparinized syringes. Neutrophils were isolated by dextran sedimentation, centrifugation over Lymphocyte Separation Medium (Organon Teknika, Durham, N.C.), and hypotonic lysis of contaminating red blood cells as described by Berman et al. (*J. Cell Biochem.* 52:183 (1993)). The final neutrophil pellet was suspended at a concentration of $1 \times 10^7$ cells/ml in assay buffer, which consisted of Hanks Balanced Salt Solution (GIBCO, Grand Island, N.Y.) supplemented with 1.0% BSA (fraction V, Sigma, St. Louis, Mo.), 2 mg/ml glucose, 4.2 mM sodium bicarbonate, and 0.01M HEPES, pH 7.2. The neutrophils were stored at 4° C. for not longer than 1 hr.

Figure 8:
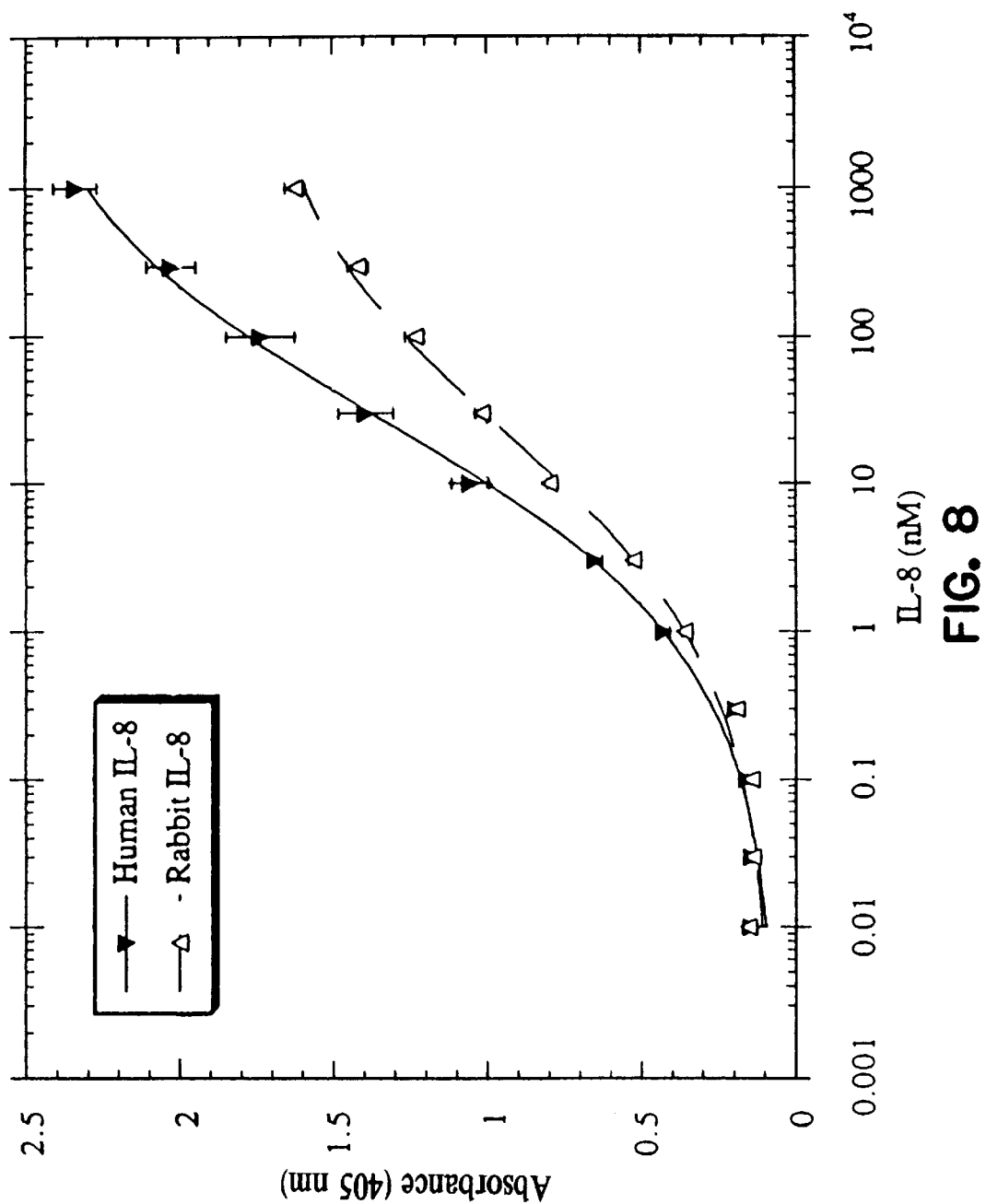
FIG. 8 depicts the stimulation of elastase release from human neutrophils by various concentrations of human and rabbit IL-8. The relative extent of elastase release was quantitated by measurement of absorbance at a wavelength of 405 nanometers (nm). The data represent mean±standard error of the mean (SEM) of triplicate samples.
Figure 9:
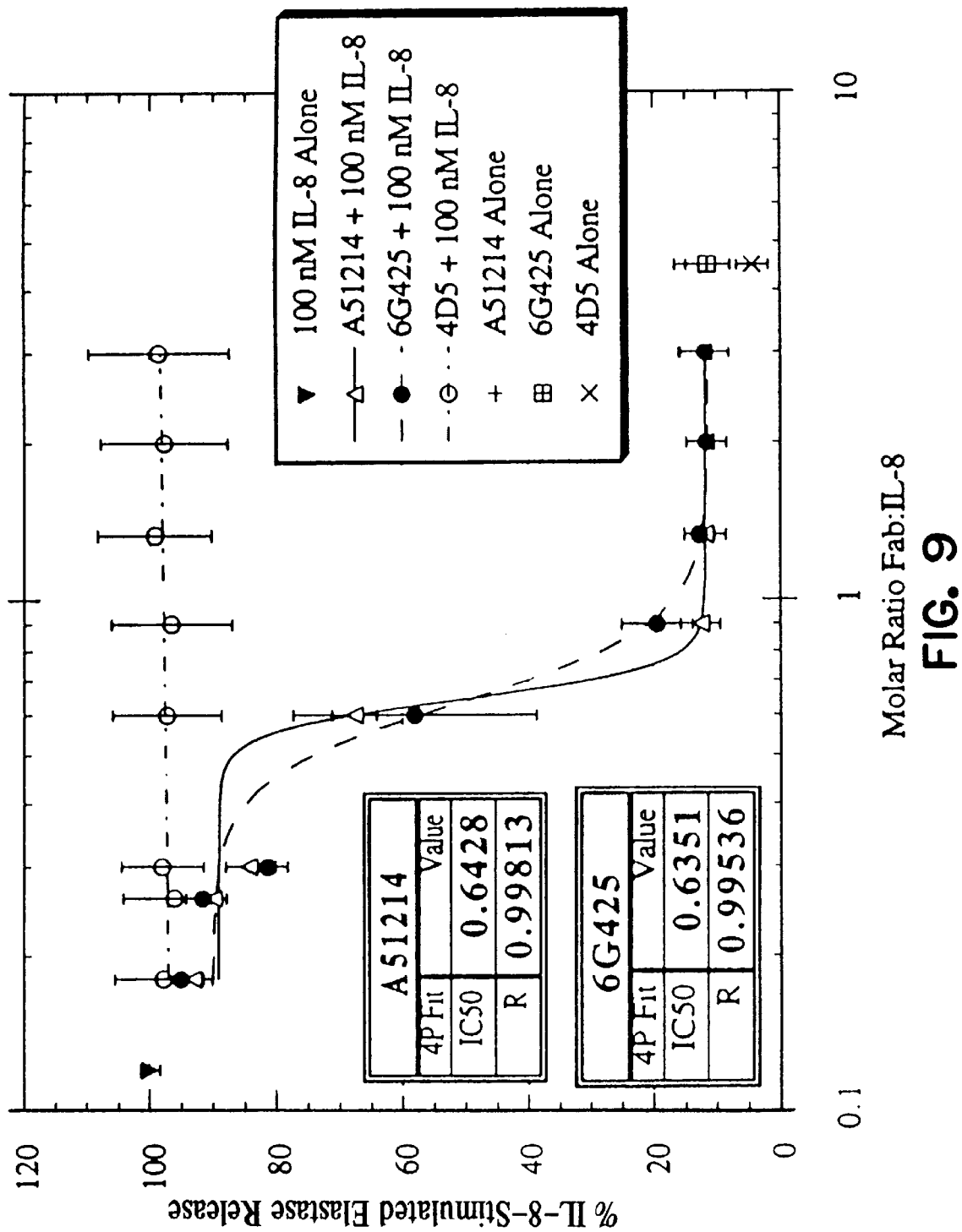
FIG. 9 is a graph depicting the ability of chimeric 6G4.2.5 Fab and chimeric 5.12.14 Fab to inhibit elastase release from human neutrophils stimulated by human IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.
Figure 10:
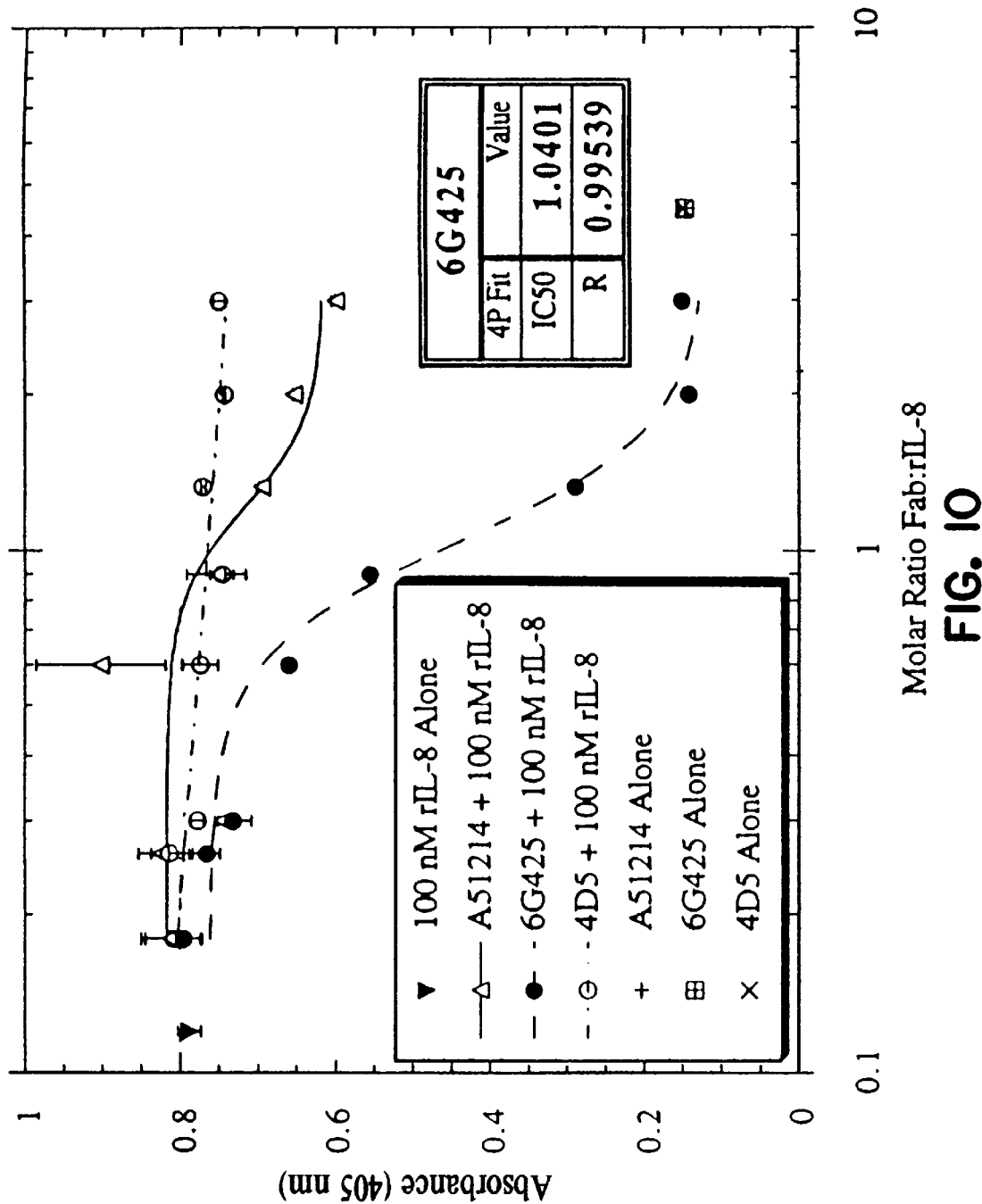
FIG. 10 is a graph depicting the relative abilities of chimeric 6G4.2.5 Fab and chimeric 5.12.14 Fab to inhibit elastase release from human neutrophils stimulated by rabbit IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.
Figure 11B:
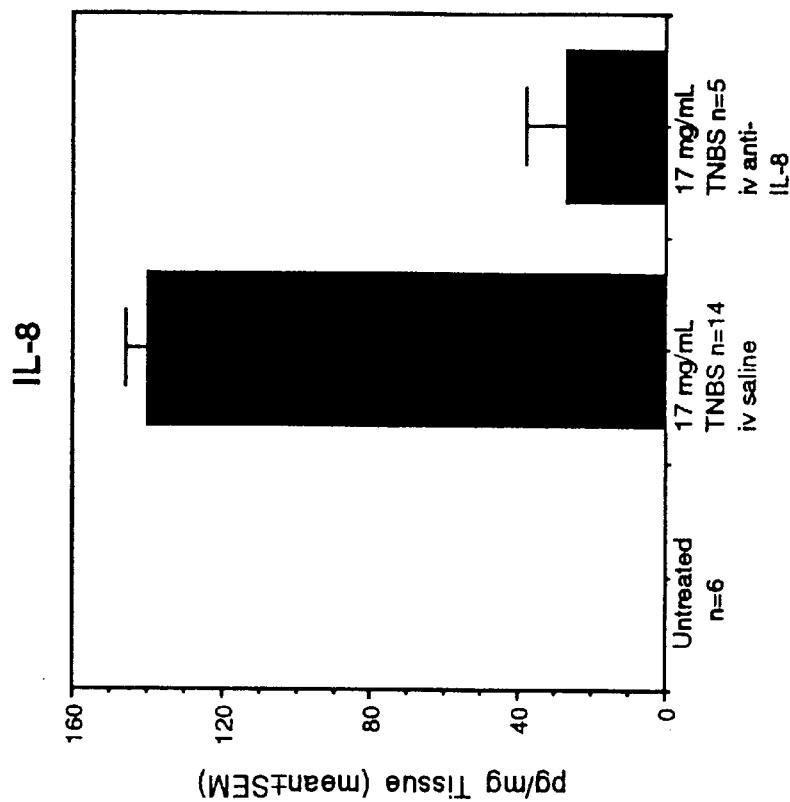
FIG. 11A–11J are a set of graphs depicting the following parameters in a rabbit ulcerative colitis model.
Figure 11A:
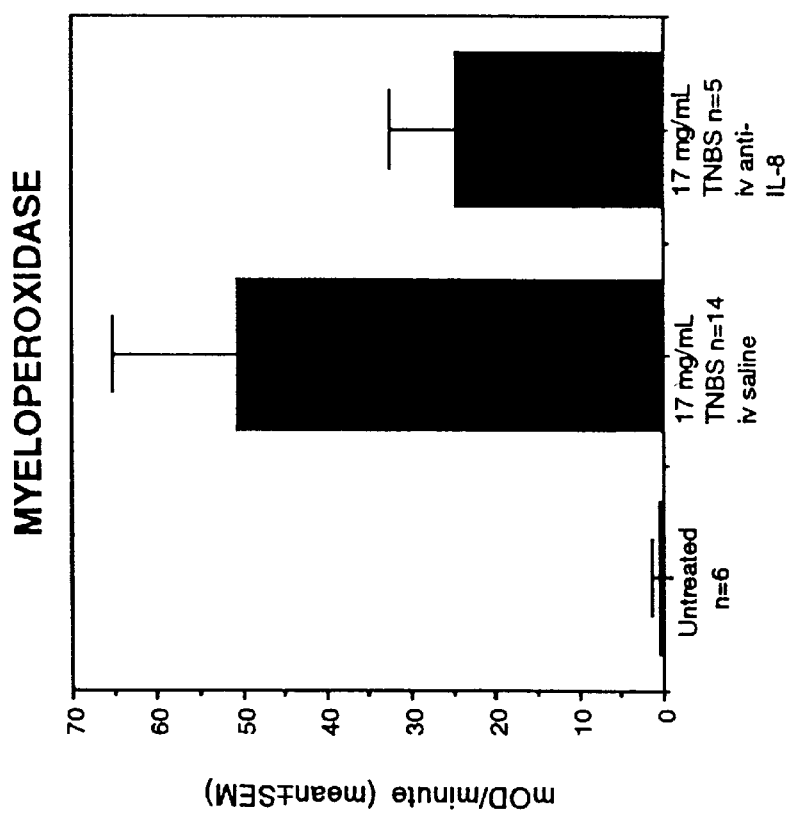
Figure 11D:
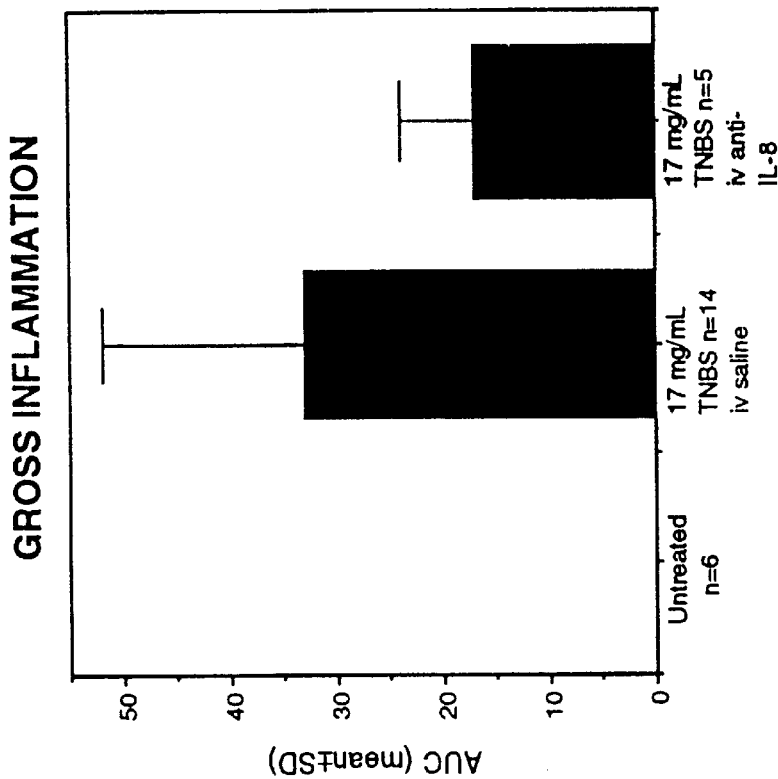
Figure 11C:
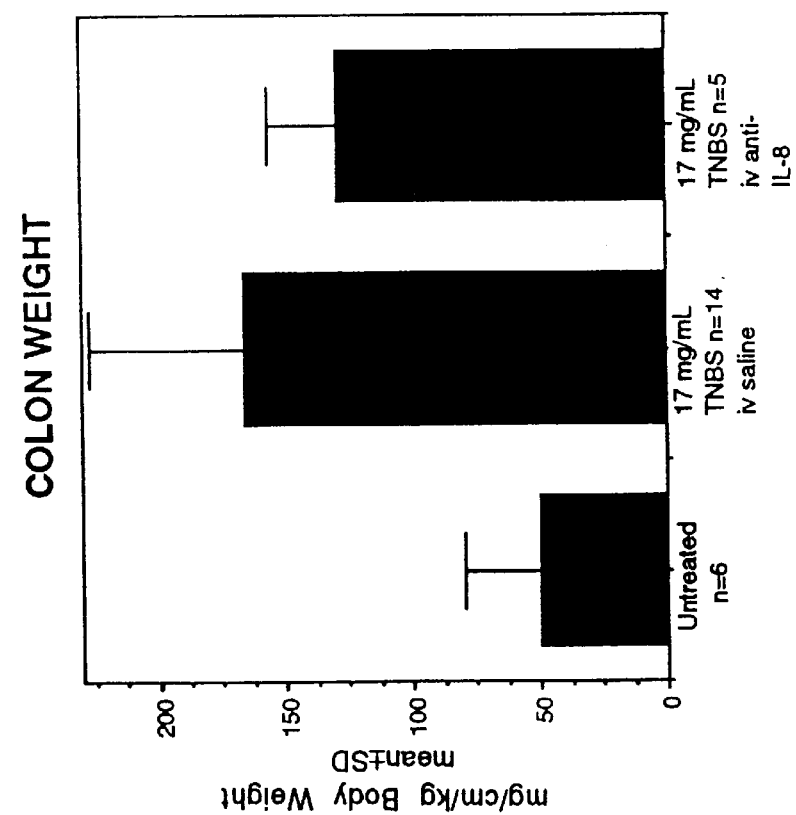
Figure 11F:
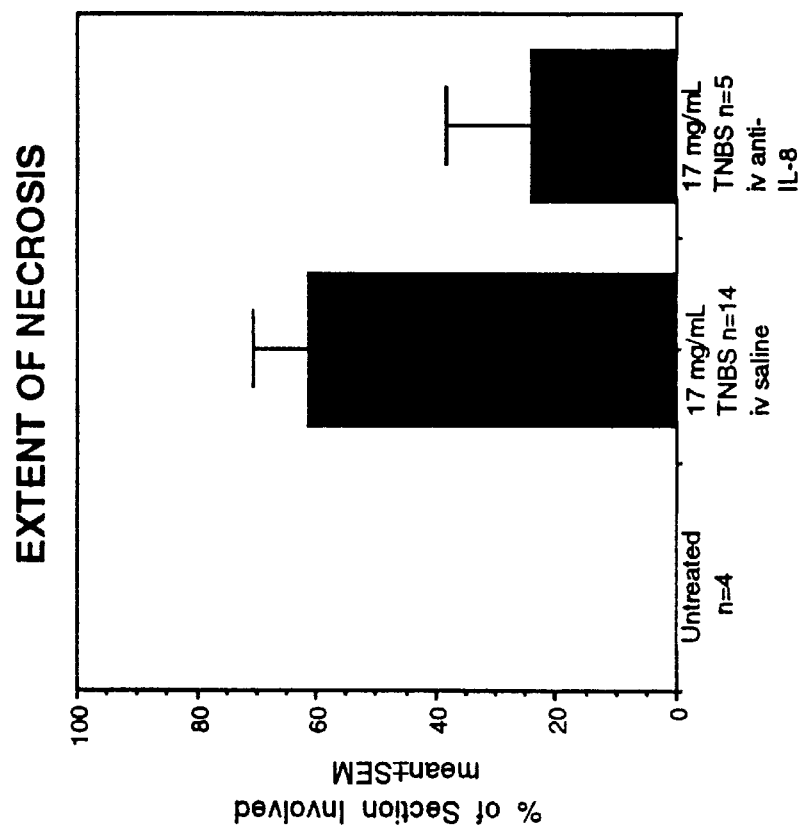
Figure 11E:
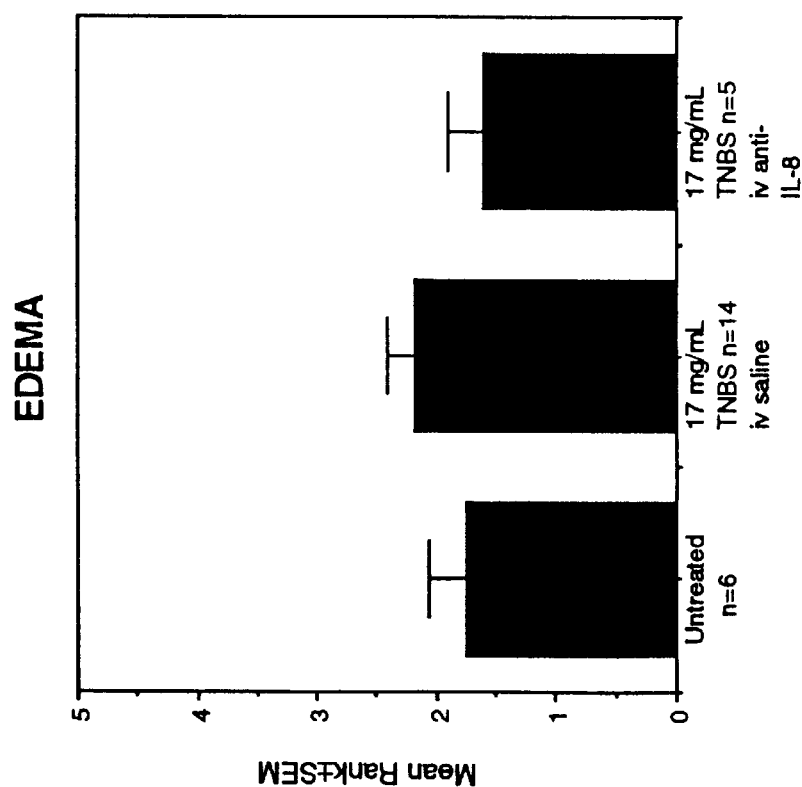
Figure 11H:
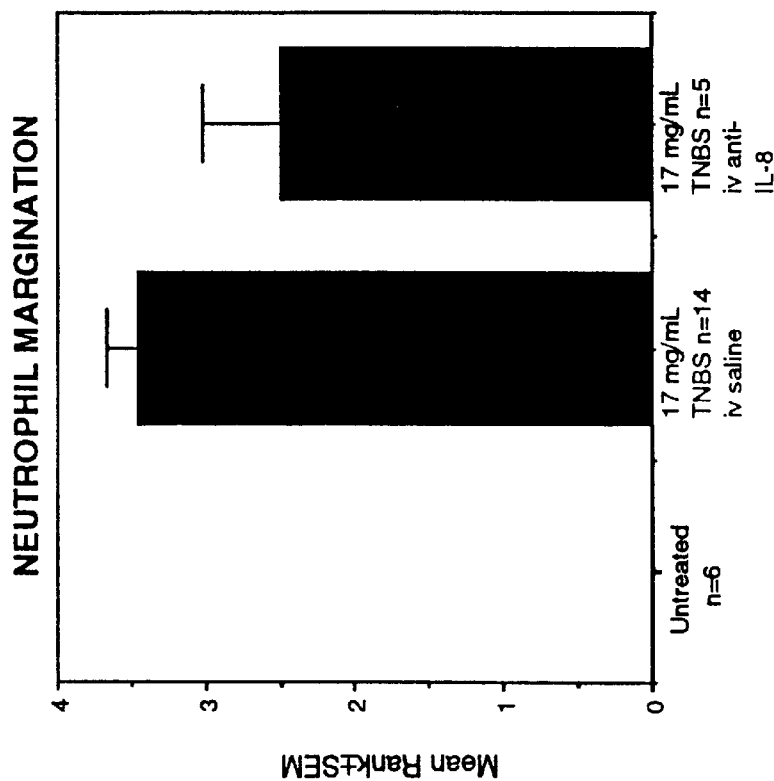
Figure 11G:
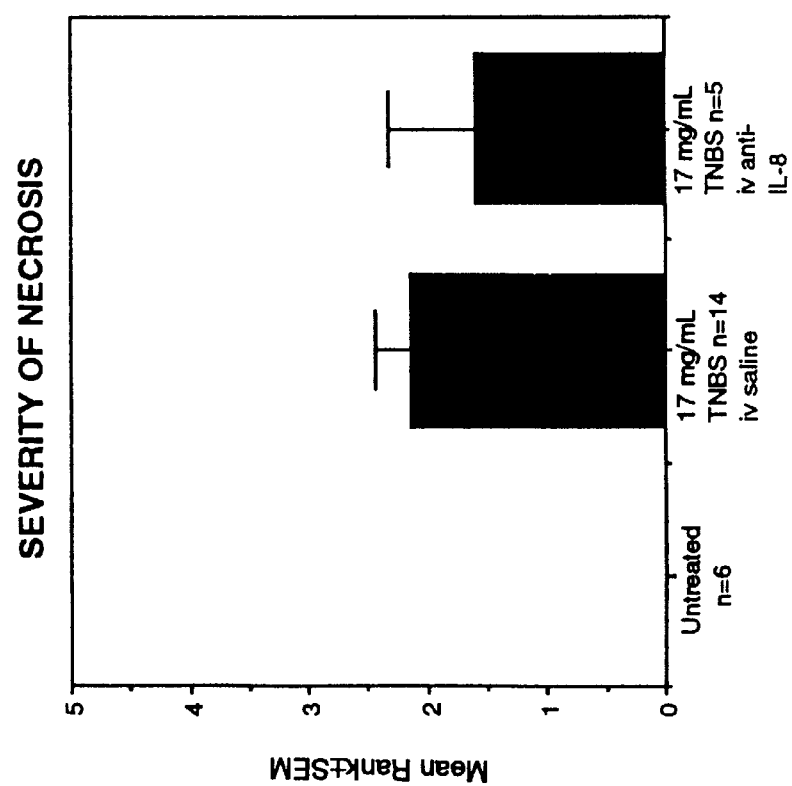
Figure 11J:
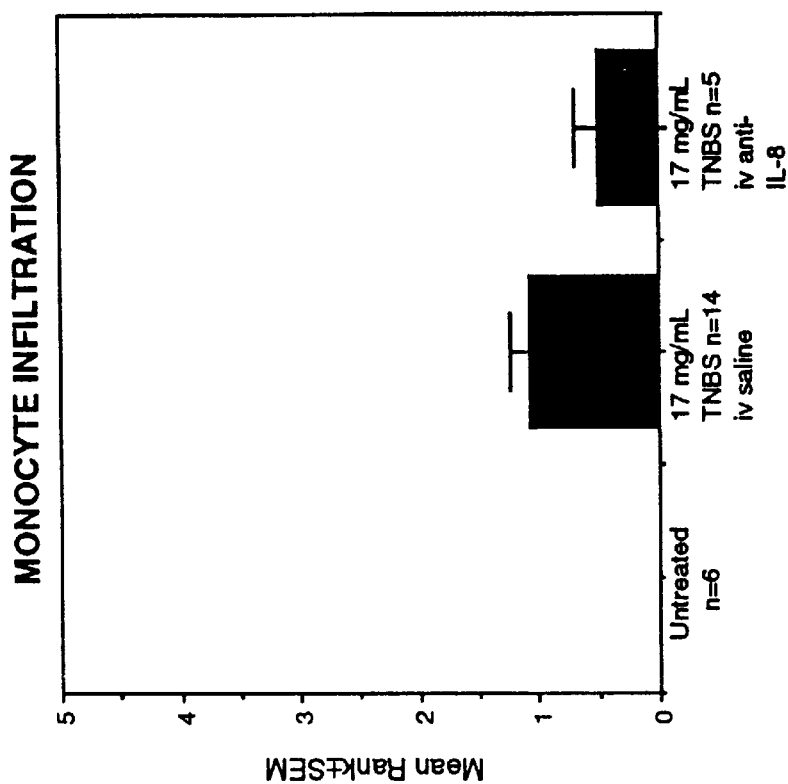
Figure 11I:
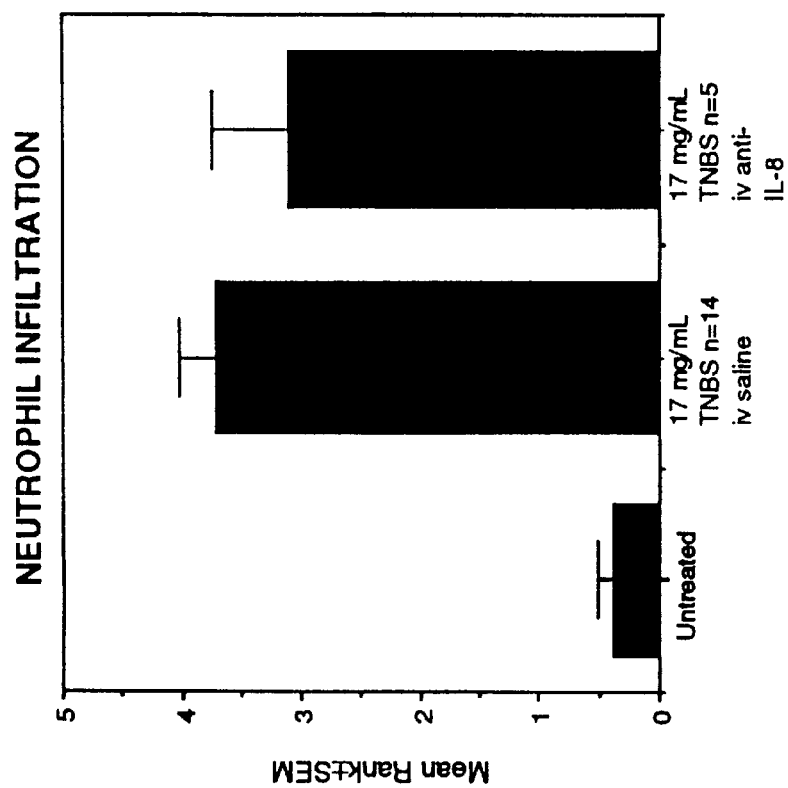

IL-8 (10 $\mu$l) was mixed with anti-IL-8 Fab, an isotype control Fab, or buffer (20 $\mu$l) in 1 ml polypropylene tubes and incubated in a 37° C. water bath for 30 min. IL-8 was used at final concentrations ranging from 0.01 to 1000 nM in dose response studies (FIG. 8) and at a final concentration of 100 nM in the experiments addressing the effects of the Fabs on elastase release (FIGS. 9 and 10). Fab concentrations ranged from approximately 20 nM to 300 nM, resulting in Fab:IL-8 molar ratios of 0.2:1 to 3:1. Cytochalasin B (Sigma) was added to the neutrophil suspension at a concentration of 5 $\mu$g/ml (using a 5 mg/ml stock solution made up in DMSO), and the cells were incubated for 15 min in a 37° C. water bath. Cytochalasin B-treated neutrophils (100 $\mu$l) were then added to the IL-8/Fab mixtures. After a 3 hr incubation at room temperature, the neutrophils were pelleted by centrifugation (200×g for 5 min), and aliquots of the cell-free supernatants were transferred to 96 well plates (30 $\mu$l/well). The elastase substrate, methoxysuccinyl-alanyl-alanyl-prolyl-valyl-p-nitroanilide (Calbiochem, La Jolla, Calif.), was prepared as a 10 mM stock solution in DMSO and stored at 4° C. Elastase substrate working solution was prepared just prior to use (1.2 mM elastase substrate, 1.2M NaCl, 0.12M HEPES, pH 7.2), and 170 $\mu$l was added to each sample-containing well. The plates were placed in a 37° C. tissue culture incubator for 30 min or until an optical density reading for the positive controls reached at least 1.0. Absorbance was measured at 405 nm using an SLT 340 plate reader (SLT Lab Instruments, Austria).

FIG. 9 demonstrates the ability of the chimeric anti-IL-8 Fabs to inhibit elastase release from human neutrophils stimulated by human IL-8; FIG. 10 demonstrates the relative abilities of the chimeric anti-IL-8 Fabs to inhibit elastase release from human neutrophils stimulated by rabbit IL-8.

C. EXPERIMENTAL COLITIS MODEL

One of the most widely accepted models of chronic experimental colitis is 2,4,6-trinitrobenezenesulfonic acid (TNBS)-induced injury, recently described by Morris et al., *Gastroenterology* 96:795 (1989). Briefly, rectal administration of 10 to 30 milligrams (mg) of TNBS in 0.25 ml of 50% ethanol produces acute and chronic local inflammation documented by dose-dependent increases in colonic weights, gross ulceration, and myeloperoxidase values. High doses of TNBS (30 mg) in ethanol produces colonic injury that peaks at 1 week but persists for at least 8 weeks after administration. Colonic inflammation is accompanied by weight loss in the first week, diarrhea in 90% of animals during weeks 1 to 3, and stenosis of the distal colon with proximal dilation, but only 3% mortality. In chronic phases, inflammation is segmental with linear (transverse) ulcers and marked thickening of the colon. Transmural acute and chronic inflammation is noted histologically with a progressive increase in inflammatory cell infiltration in the external muscle and serosa during weeks 3 to 5. Mucosal and serosal granulomas are present in 55% of animals examined at 2 to 3 weeks and in approximately 20% of animals 4 weeks or more after injury.

To study the ability of the anti-IL-8 antibodies of the invention to attenuate acute colitis in rabbits, colitis was induced in New Zealand White rabbits (1.8–2 kilograms (kg) body weight) by intracolonic instillation of 5 ml of 17–35 mg/ml Trinitrobenzene sulfonic acid in 30% ethanol (TNBS/EtOH) (adapted from the method of Morris et al., *Gastroenterology* 96:795 (1989)) Five rabbits were treated intravenously with 5 mg/kg 6G4.2.5. Three control rabbits received PBS. Animals treated with TNBS/EtOH were euthanized after 24 hours post dosing and the colon tissue was examined for levels of IL-8, myeloperoxidase (enzyme marker for polymorphonuclear leukocytes or heterophils), wet colon weight, gross inflammation, and histopathology. Two sections of colon were preserved in formalin, processed by standard techniques for routine hematoxylin and eosin sections. The colon tissue was examined for levels of IL-8 by enzyme linked immunoassay. Wet colon weight from treated and untreated rabbits was measured and compared. Edema was measured as the thickness of the submucosa in 3 to 5 sites per sample. Leukocytic margination was evaluated by determining which vessels in the tissue section were affected (e.g., superficial, involving only the subepithelial vessels in the lamina propria, to marked, involving vessels in the submucosa). The extent of necrosis was measured as the percent of the colon manifesting necrosis. The severity of necrosis was measured as the depth of penetration of necrosis into the wall of the colon. Gross inflammation was defined as the severity of inflammation over the length of the involved colon and was scored visually based upon the degree of swelling and coloration. Leukocytic infiltration was determined by counting the number of neutrophils per high power field (HPF) (40× magnification). Mononuclear cell infiltration was determined by counting the number of mononuclear cells per HPF (40× magnification).

Heterophil (neutrophil) influx into inflamed rabbit colonic tissue was monitored by measurement of MPO levels (see, for example, Bradley et al., *J. Invest. Dermatol.* 7B:206 (1982)). Briefly, colonic sections were placed in 15 ml polypropylene tubes and incubated at 60° C. for 2 hours. The tissues were frozen in liquid nitrogen. Fine powder tissue lysates were prepared with a mortar and pestle and transferred into 15 ml polypropylene tubes. The tissue samples were solubilized in 0.5% hexadecyl trimethyl ammonium (HTAB) (0.5% weight to volume (w/v) in 50 mM $KPO_4$ buffer at pH 6) at a ratio of 3.5 ml per gram of tissue using a tissue homogenizer. The samples were frozen and thawed twice by freezing in liquid nitrogen and thawing in 60° C. water bath. The samples were then sonicated for 10 seconds at a 50% duty cycle at 2.5 power level. Each sample lysate was transferred to an microfuge tube and centrifuged at room temperature for 15 minutes at 15,600×g. The samples were transferred to fresh clean Microfuge tubes. Seventy five $\mu l$ of each sample and 75 $\mu l$ of human MPO standard positive control (Calbiochem Corp., San Diego, Calif.) in HTAB diluted to 0.03 units per well were transferred in triplicate to a 96 well flat bottom plate. Seventy-five $\mu l$ of HTAB (0.5% w/v in 50 mM KPO4 buffer pH 6.0) were added as reference blanks. One hundred $\mu l$ of $H_2O_2$ were added to each well. The reaction in the 96 well plate was monitored on a Thermo Max optical plate reader (Molecular Devices Co. Menlo Park, Calif.). A stock solution of O-dianisidine (Sigma, St. Louis, Mo.) at 10 mg dry powder in 1.0 ml of distilled $H_2O$ was prepared and drawn through a 0.2 micron filter. Twenty-five $\mu l$ were added to each well. The plates were read at OD 450 nm continuously at 3–5 minute intervals over a 30 minute period.

Increased levels of myeloperoxidase and IL-8 were detected in animals dosed with increasing doses of TNBS/EtOH as compared to sham treated control animals. Increased colonic weight and gross inflammation were also evident. Histological evaluation revealed mucosal necrosis of the bowel wall, with heterophil margination of the blood vessels and infiltration in the affected tissue.

However, treatment of rabbits with anti-IL-8 antibodies reduced the severity of TNBS/EtOH-induced colitis. Lesions in animals treated with 5 milligrams per kilogram of body weight (mg/kg) intravenous 6G4.2.5, lust prior to colitis induction with TNBS/EtOH, were attenuated in 4 of 5 animals as compared to 3 control animals. Antibody treatment reduced the extent and severity of necrosis, gross inflammation, colonic weight, edema, heterophil margination and infiltration. The levels of colonic myeloperoxidase and IL-8 were greatly reduced. The results of these experiments are depicted in FIGS. 11A–11J. These observations support the usefulness of anti-IL-8 antibodies in the attenuation of colitis.

D. EFFECT OF ANTI-IL-8 ON NEUTROPHIL EMIGRATION DURING BACTERIAL PNEUMONIA

Neutrophils migrate into the lung in response to a variety of stimuli, including infection by *Streptococcus pneumoniae*. To determine whether the anti-IL-8 antibodies of the instant invention could inhibit such neutrophil migration, thereby ameliorating inflammation in the lung, a rabbit pneumonia model was used. Briefly, anesthetized New Zealand white rabbits were given intrabronchial instillations of *Streptococcus pneumoniae*, *Escherichia coli*, or *Pseudomonas aeruginosa* ($3 \times 10^9$ organisms/ml) combined with either anti-rabbit IL-8 antibody (clone 6G4.2.5) or control mouse IgG (final concentration 0.5 mg/ml) and colloidal carbon (5%) in a total volume of 0.5 ml. After 3 hours and 50 min, the rabbits received an intravenous injection of radiolabeled microspheres to measure pulmonary blood flow. At 4 hours, the heart and lungs were removed and the lungs were separated. The pneumonic region (usually the left lower lobe) as indicated by the colloidal carbon and the corresponding region in the contralateral lung was lavaged using phosphate-buffered saline. Total leukocyte counts were obtained using a hemacytometer on the lavage fluid and differential counts were performed on Wright-stained cytospin preparations.

Figure 12:
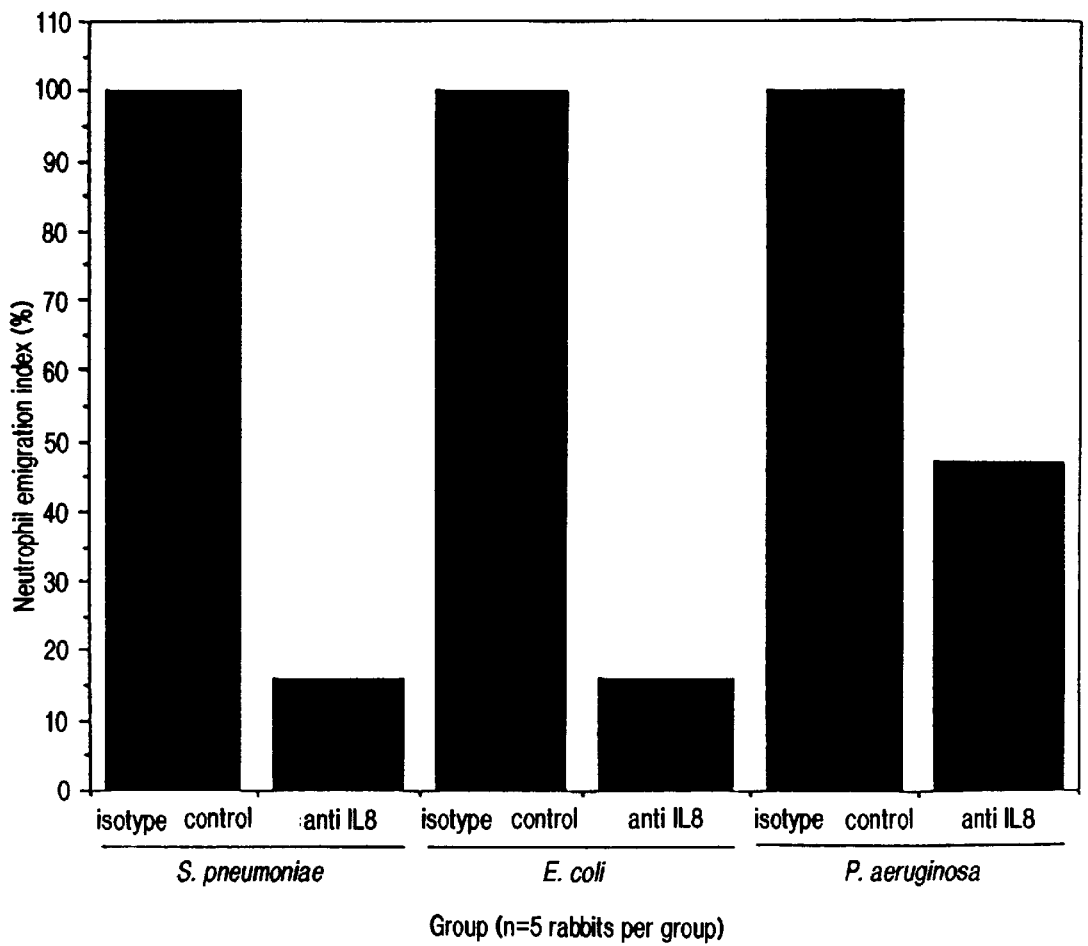
FIG. 12 is a graph depicting the effect of anti-IL-8 monoclonal antibody treatment on the number of neutrophils in bronchoalveolar lavage (BAL) fluid in animals infected with *Streptococcus pneumoniae, Escherichia coli,* or *Pseudomonas aeruginosa*. Treatment with 6G4.2.5 significantly reduced the number of neutrophils present in the BAL fluid compared to animals treated with isotype control mouse IgG (FIG. 12).

Treatment with anti-rabbit IL-8 antibodies significantly reduced the number of neutrophils present in the BAL fluid compared to animals treated with isotype control mouse IgG (FIG. 12). Thus, anti-IL-8 antibodies effectively reduce neutrophil emigration in the pneumonic lung.

E. MOLECULAR CLONING OF THE VARIABLE LIGHT AND HEAVY REGIONS OF THE MURINE 5.12.14 (ANTI-IL-8) MONOCLONAL ANTIBODY

Total RNA was isolated from $1 \times 10^8$ cells (hybridoma cell line ATCC HB-11722) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest*, Kabat, E. A. et al. (1991) NIH Publication 91-3242, V 1–3.) Three primers were designed for each of the light and heavy chains to increase the chances of primer hybridization and efficiency of first strand cDNA synthesis (FIG. 13). Amplification of the first strand cDNA to double-stranded (ds) DNA was accomplished using two sets of synthetic DNA oligonucleotide primers: one forward primer and one reverse primer for the light chain variable region amplification (FIG. 14) and one forward primer and one reverse primer for the heavy chain variable region amplification (FIG. 15). The N-terminal sequence of the first eight amino acids of either the light or heavy chains of 5.12.14 was used to generate a putative murine DNA sequence corresponding to this region. (A total of 29 amino acids was sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, MluI, for both the light chain variable region forward primer and the heavy chain variable region forward primer to facilitate ligation to the 3' end of the STII element in the cloning vector. The reverse amplification primers were designed to anneal with the murine DNA sequence corresponding to a portion of the constant region of the light or heavy chains near the variable/constant junction. The light chain variable region reverse primer contained a unique BstBI restriction site and the heavy chain variable region reverse primer contained a unique ApaI restriction site for ligation to the 5' end of either the human IgG1 constant light or IgG1 constant heavy regions in the vectors, pB13.1 (light chain) and pB14 (heavy chain). The polymerase chain reaction using these primer sets yielded DNA fragments of approximately 400 bp. The cDNA encoding the 5.12.14 light chain variable region was cloned into the vector pB13.1, to form pA51214VL and the 5.12.14 heavy chain variable region was cloned into the vector, pB14, to form pA51214VH. The cDNA inserts were characterized by DNA sequencing and are presented in FIG. 16 (murine light chain variable region) and FIG. 17 (murine heavy chain variable region).

F. CONSTRUCTION OF A 5.12.14 FAB VECTOR

In the initial construct, pA51214VL, the amino acids between the end of the 5.12.14 murine light chain variable sequence and the unique cloning site, BstBI, in the human IgG1 constant light sequence were of murine origin corresponding to the first 13 amino acids of the murine IgG1 constant region (FIG. 16). Therefore, this plasmid contained a superfluous portion of the murine constant region separating the 5.12.14 murine light chain variable region and the human light chain IgG1 constant region. This intervening sequence would alter the amino acid sequence of the chimera and most likely produce an incorrectly folded Fab. This problem was addressed by immediately truncating the cDNA clone after A109 and re-positioning the BstBI site to the variable/constant junction by the polymerase chain reaction. FIG. 18 shows the amplification primers used to make these modifications. The forward primer, VL.front, was designed to match the last five amino acids of the STII signal sequence, including the MluI cloning site, and the first 4 amino acids of the 5.12.14 murine light chain variable sequence. The sequence was altered from the original cDNA in the third position of the first two codons D1 (T to C) and I2 (C to T) to create a unique EcoRV cloning site which was used for later constructions. The reverse primer, VL.rear, was designed to match the first three amino acids of the human IgG1 constant light sequence and the last seven amino acids of the 5.12.14 light chain variable sequence which included a unique BstBI cloning site. In the process of adding the BstBI site, the nucleotide sequence encoding several amino acids were altered: L106 (TTG to CTT), K107 (AAA to CGA) resulting in a conservative amino acid substitution to arginine, and R108 (CGG to AGA). The PCR product encoding the modified 5.12.14 light chain variable sequence was then subcloned into pB13.1 in a two-part ligation. The MluI-BstBI digested 5.12.14 PCR product encoding the light chain variable region was ligated into MluI-BstBI digested vector to form the plasmid, pA51214VL'. The modified cDNA was characterized by DNA sequencing. The coding sequence for the 5.12.14 light chain is shown in FIG. 19.

Likewise, the DNA sequence between the end of the heavy chain variable region and the unique cloning site, ApaI, in the human IgG1 heavy chain constant domain of pA51214VH was reconstructed to change the amino acids in this area from murine to human. This was done by the polymerase chain reaction. Amplification of the murine 5.12.14 heavy chain variable sequence was accomplished using the primers shown in FIG. 18. The forward PCR primer was designed to match nucleotides 867–887 in pA51214VH upstream of the STII signal sequence and the putative cDNA sequence encoding the heavy chain variable region and included the unique cloning site SpeI. The reverse PCR primer was designed to match the last four amino acids of the 5.12.14 heavy chain variable sequence and the first six amino acids corresponding to the human IgG1 heavy constant sequence which also included the unique cloning site, ApaI. The PCR product encoding the modified 5.12.14 heavy chain variable sequence was then subcloned to the expression plasmid, pMHM24.2.28 in a two-part ligation. The vector was digested with SpeI-ApaI and the SpeI-ApaI digested 5.12.14 PCR product encoding the heavy chain variable region was ligated into it to form the plasmid, pA51214VH'. The modified cDNA was characterized by DNA sequencing. The coding sequence for the 5.12.14 heavy chain is shown in FIG. 20.

The first expression plasmid, pantiIL-8.1, encoding the chimeric Fab of 5.12.14 was made by digesting pA51214VH' with EcoRV and Bpu1102I to replace the EcoRV-Bpu1102I fragment with a EcoRV-Bpu1102I fragment encoding the murine 5.12.14 light chain variable region of pA51214VL'. The resultant plasmid thus contained the murine-human variable/constant regions of both the light and heavy chains of 5.12.14.

Preliminary analysis of Fab expression using pantiIL-8.1 showed that the light and heavy chains were produced intracellularly but very little was being secreted into the periplasmic space of *E. coli*. To correct this problem, a second expression plasmid was constructed.

The second expression plasmid, pantiIL-8.2, was constructed using the plasmid, pmy187, as the vector. Plasmid pantiIL-8.2 was made by digesting pmy187 with MluI and SphI and the MluI (partial)-SphI fragment encoding the murine 5.12.14 murine-human chimeric Fab of pantiIL-8.1 was ligated into it. The resultant plasmid thus contained the murine-human variable/constant regions of both the light and heavy chains of 5.12.14.

The plasmid pantiIL-8.2 was deposited on Feb. 10, 1995 with the American Type Culture Collection, 12301 Parklawn Drive, Rockville, Md., U.S.A. (ATCC) and assigned ATTC Accession No. ATCC 97056. This deposit was made under the provisions of the Budapest Treaty on the International Recognition of the Deposit of Microorganisms for the Purpose of Patent Procedure and the Regulations thereunder (Budapest Treaty).

G. MOLECULAR CLONING OF THE VARIABLE LIGHT AND HEAVY REGIONS OF THE MURINE 6G4.2.5 MONOCLONAL ANTIBODY

Total RNA was isolated from $1 \times 10^8$ cells (hybridoma cell line 6G4.2.5) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest,* Kabat et al. (1991) NIH Publication 91-3242, V 1–3). Three primers were designed for each the light and heavy chains to increase the chances of primer hybridization and efficiency of first strand cDNA synthesis (FIG. 21). Amplification of the first strand cDNA to double-stranded (ds) DNA was accomplished using two sets of synthetic DNA oligonucleotide primers: one forward primer and one reverse primer for the light chain variable region amplification (FIG. 22) and one forward primer and one reverse primer for the heavy chain variable region amplification (FIG. 23). The N-terminal sequence of the first eight amino acids of either the light or heavy chains of 6G4.2.5 was used to generate a putative murine DNA sequence corresponding to this region. (A total of 29 amino acids were sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, NsiI, for the light chain variable region forward primer and the unique restriction site, MluI, for the heavy chain variable region forward primer to facilitate ligation to the 3' end of the STII element in the vector, pchimFab. The reverse amplification primers were designed to anneal with the murine DNA sequence corresponding to a portion of the constant region of the light or heavy chains near the variable/constant junction. The light chain variable region reverse primer contained a unique MunI restriction site and the heavy chain variable region reverse primer contained a unique ApaI restriction site for ligation to the 5' end of either the human IgG1 constant light or IgG1 constant heavy regions in the vector, pchimFab. The polymerase chain reaction using these primer sets yielded DNA fragments of approximately 400 bp and were cloned individually into the vector, pchimFab, to form p6G425VL and p6G425VH. The cDNA inserts were characterized by DNA sequencing and are presented in FIG. 24 (murine light chain variable region) and FIG. 25 (murine heavy chain variable region).

H. CONSTRUCTION OF A 6G4.2.5 CHIMERIC FAB VECTOR

In the initial construct, p6G425VL, the amino acids between the end of the 6G4.2.5 murine light chain variable sequence and the unique cloning site, MunI, in the human IgG1 constant light sequence were of murine origin. These amino acids must match the human IgG1 amino acid sequence to allow proper folding of the chimeric Fab. Two murine amino acids, D115 and S121, differed dramatically from the amino acids found in the loops of the β-strands of the human IgG1 constant domain and were converted to the proper human amino acid residues, V115 and F121, by site-directed mutagenesis using the primers shown in FIG. 26. These specific mutations were confirmed by DNA sequencing and the modified plasmid named p6G425VL'. The coding sequence is shown in FIG. 27.

Likewise, the DNA sequence between the end of the heavy chain variable region and the unique cloning site, ApaI, in the human IgG1 heavy chain constant domain of p6G425VH was reconstructed to change the amino acids in this area from murine to human. This process was facilitated by the discovery of a BstEII site near the end of the heavy chain variable region. This site and the ApaI site were used for the addition of a synthetic piece of DNA encoding the corresponding IgG human amino acid sequence. The synthetic oligo-nucleotides shown in FIG. 26 were designed as complements of one another to allow the formation of a 27 bp piece of ds DNA. The construction was performed as a three-part ligation because the plasmid, p6G425VH, contained an additional BstEII site within the vector sequence. A 5309 bp fragment of p6G425VH digested with MluI-ApaI was ligated to a 388 bp fragment carrying the 6G4.2.5 heavy chain variable region and a 27 bp synthetic DNA fragment encoding the first six amino acids of the human IgG1 constant region to form the plasmid, p6G425VH'. The insertion of the synthetic piece of DNA was confirmed by DNA sequencing. The coding sequence is shown in FIG. 28.

The expression plasmid, p6G425chim2, encoding the chimeric Fab of 6G4.2.5 was made by digesting p6G425chimVL' with MluI and ApaI to remove the STII-murine HPC4 heavy chain variable region and replacing it with the MluI-ApaI fragment encoding the STII-murine 6G4.2.5 heavy chain variable region of p6G425chimVH'. The resultant plasmid thus contained the murine-human variable/constant regions of both the light and heavy chains of 6G4.2.5.

The plasmid p6G425chim2 was deposited on Feb. 10, 1995 with the American Type Culture Collection, 12301 Parklawn Drive, Rockville, Md., U.S.A. (ATCC) and assigned ATTC Accession No. 97055. This deposit was made under the provisions of the Budapest Treaty on the International Recognition of the Deposit of Microorganisms for the Purpose of Patent Procedure and the Regulations thereunder (Budapest Treaty).

I. EFFECT OF IL-8 HOMOLOG RECEPTOR KNOCK-OUT IN TRANSGENIC MOUSE ASTHMA MODEL

IL-8 is a potent chemoattractant for neutrophils and has also been shown to activate eosinophils. To investigate the function of IL-8 in the migration and activation of leukocytes in asthma, a murine model for allergic asthma utilizing wild type and IL-8 homolog receptor knock-out mice was developed. The murine asthma model reproduces several aspects typical of this disease, including allergen-specific IgE titers, high percentage of eosinophils in the bronchoalveolar lavage, lung mucosal infiltrates of macrophages, lymphocytes and plasma cells, and hypersecretion of mucus.

Balb/C IL-8 homolog receptor knock-out mice were generated by crossing C57BL/6J IL-8 homolog receptor (IL8Rh) knock-out mice (produced according to the methods of Cacalano et al., *Science*, 265: 682–684 (1994)) against balb/C mice until a genotype consisting of the IL8Rh knock-out carrying chromosome against a balb/C genetic background was obtained. Female Balb/C wild type (WT) and IL-8 homolog receptor knock-out (KO) litter mates were bred and checked for genotype by tail sampling. The animals were 6 to 8 weeks old at the beginning of the study.

Both WT and KO mice were randomly divided into groups of controls and asthmatics, each group containing 7 animals for statistical analysis. The asthmatic groups were injected intraperitoneally on day 0 with 0.1 ml of a solution of 100 $\mu$g/ml ovalbumin grade V (Sigma, Mo.) and 10 mg/ml aluminum oxide (Intergen, N.Y.) in Dulbecco's Phosphate Buffered Saline (DPBS) (HyClone, Utah). On day 14 through day 20 both asthmatic and control groups were aerosolized for 30 minutes each day with a solution of 10 mg/ml ovalbumin in DPBS. The aerosolization was performed by placing 14 animals in a 16.5×17×52 cm Plexiglas cage connected to a Ultra-Neb 99 nebulizer (DeVilbiss, Pa.) set at an output of 1.7 ml/min. Serum, whole blood, bronchoalveolar lavage and lung tissues were harvested on day 21 as described below.

Blood was collected through the orbital sinus and clotted in a Microtainer Serum Separator (Becton Dickinson, N.J.) for serum harvest.

Ovalbumin-specific IgE titers were determined as follows. Wells in Maxi-Sorp F96 Nunc-Immunoplates (Nunc, Denmark) were each coated with 100 $\mu$l of 2 $\mu$g/ml Fc$\bar{\epsilon}$RI-HuIgG1 (obtained as described in Haak-Frendscho et al., *J. Immunol.*, 151: 351–358 (1993)) in phosphate buffered saline (PBS) and incubated overnight at 4° C. Plates were rinsed twice in PBS and coated wells were each incubated for 1–2 hours at room temperature (RT) in 400 $\mu$l of blocking solution (50 mM Tris-buffered saline, 0.5% bovine serum albumin (BSA), 0.05% Tween 20 in PBS). Serum samples were serially diluted (beginning with a 1:20 dilution) in blocking solution, and each dilution was layered onto a coated well. The plates were incubated at RT for two hours with agitation.

Following the incubation of the coated plates with serum samples, the plates were rinsed 3 times in a washing buffer and each well was incubated with 100 μl of 10 μg/ml ovalbumin in blocking solution for 1 hour at RT. Goat anti-ovalbumin (Cappel (Organon Teknika) Catalog #55297, Durham, N.C.) was conjugated to horseradish peroxidase (HRP) and diluted 1:7000 in blocking solution. Plates were then rinsed 3 times in washing buffer and each well was incubated with 100 μl of the HRP-conjugated goat anti-ovalbumin dilution for 1 hour at RT with agitation. Plates were again rinsed 3 times in washing buffer and each well was developed in 100 μl o-phenylenediamine dihydrochloride (OPD) solution (mixed from one 5 mg OPD tablet (Sigma), 12.5 ml PBS, and 5 μl $H_2O_2$) and 100 μl 2M $H_2SO_4$ for 30 minutes at RT. The plates were assayed for fluorescence at 492 nm in a UV Kinetic Microplate Reader (Molecular Devices, California).

Whole blood was collected through the orbital sinus into 0.2% $K_2EDTA$ and checked for clots. Blood smears of each animal were air dried, fixed in methanol and stained with Diff-Quick (Baxter, Ill.). Microscopic examination of these slides determined the eosinophil, macrophage, lymphocyte, neutrophil and basophil differentials Hemograms were obtained by analyzing 10 ml of a 1:250 dilution of whole blood on a Serono 9018 Hematology Analyzer (Baker Diagnostics, N.J.). Calculation of the total number of cells was done by assuming that 7% of the mouse body weight is blood.

Mice were anesthetized with 0.1 mg/kg Ketamine HCl (Ketaset, Fort Dodge Laboratories, Iowa) and 0.5 mg/kg Acepromazine Maleate (PromAce, Aveco Co. Inc., Iowa) deliveredin a single intraperitoneal injection. The mice were placed in dorsal recumbency and the trachea surgically exposed and incised ½ to ⅔ through to insert a cannula. The cannula (Micro-renathane, 0.040 OD×0.025 ID) was connected to a blunt 22 gauge needle and this was attached to a three-way stopcock assembled with two 3 cc syringes. One syringe contained 2 ml HBSS (BioWhittaker, Md.) and the other syringe was empty for collection. The lungs were gently lavaged with 4×0.5 ml aliquots of HBSS, which were collected into the empty syringe. Once harvested, the lavages were kept refrigerated.

The cells in the lavages were pelleted and resuspended in 0.2 ml saline. Hemograms were obtained as described above and the concentration adjusted to 200–400 cells/μl. An aliquot of 150 μl was utilized to prepare a slide using a Shandon Cytospin 3 centrifuge. The slides were dried, fixed, stained and read as described above for the differential.

The mice were euthanized by cervical dislocation after the lavages were collected and the lungs were surgically removed. A 3 cc syringe fitted with a 22 gauge blunt needle was filled with 10% neutral buffered formalin pH 6.8–7.2 (Richard-Allan, Mich.) and inserted into the trachea. The lungs were gently inflated and the trachea sutured. The tissue specimens were stored in the 10% buffered formalin for further processing.

Lung tissue specimens were prepared by cutting a longitudinal section of the left lobe and a cross section of the 3 right lobes, processing the samples in a TissueTek VIP (Miles, N.Y,) to exchange water for paraffin, embedding each sample in a paraffin cube, obtaining thin sections by microtome cutting (Leica, Germany), mounting the thin sections on slides, and staining the mounted samples with hematoxylineosin and sealing with a cover glass.

Figure 29:
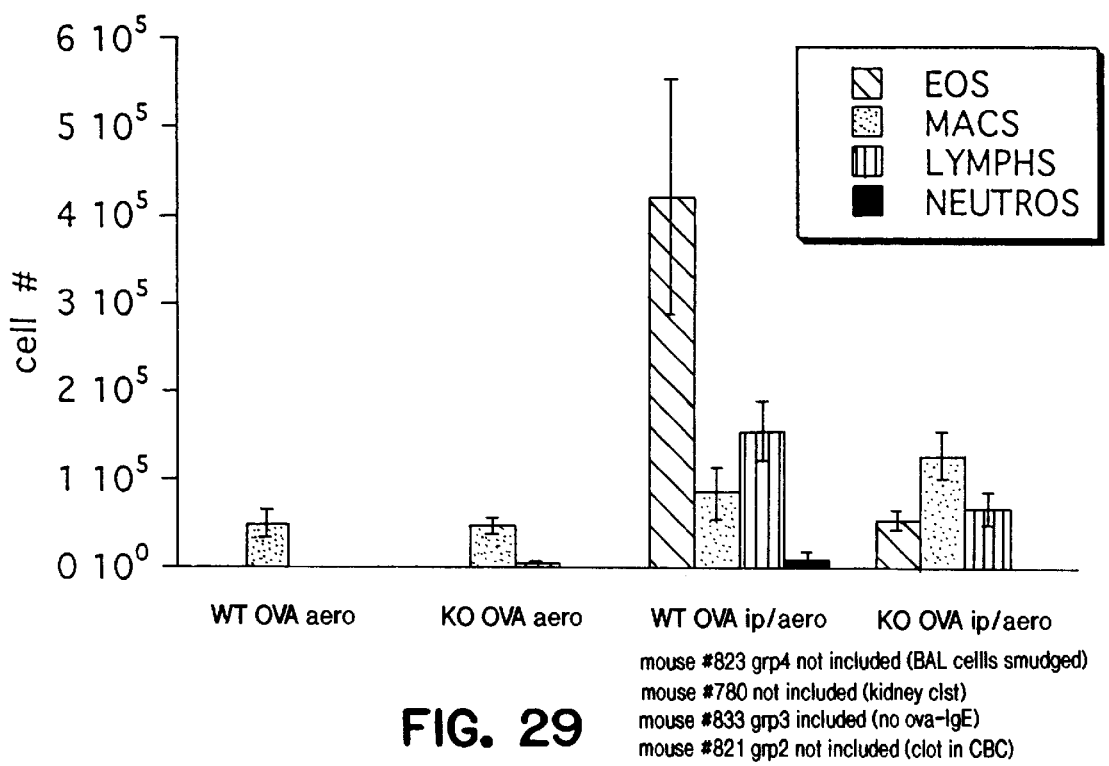
FIG. 29 is a graph depicting the effect of the absence of IL-8 receptor homolog (IL8Rh) on eosinophil, macrophage, lymphocyte and neutrophil transmigration into the lung in an asthma model using wild type and IL8Rh knock-out (KO) mice. Transmigration levels are presented as bronchoalveolar lavage (BAL) fluid cell counts. Cell counts for wild type (WT) and IL8Rh KO control mice that were exposed to aerosolized ovalbumin allergen without prior allergen challenge are denoted as "WT OVA aero" and "KO OVA aero", respectively. Cell counts for wild type and IL8Rh KO mice that were intraperitoneally inoculated with ovalbumin allergen and subsequently exposed to aerosolized allergen are denoted as "WT OVA ip/aero" and "KO OVA ip/aero", respectively. Eosinophil, macrophage, lymphocyte and neutrophil cell counts are depicted with diagonally hatched, shaded, vertically striped, and solid columns, respectively.

As shown in the eosinophil bronchoalveolar lavage (BAL) counts obtained for asthmatic IL8Rh KO mice and asthmatic WT mice displayed in Table II below and in FIG. 29, the asthmatic KO mice presented a dramatic 18-fold decrease in the number of eosinophils in the bronchoalveolar lavage when compared to WT asthmatics.

TABLE II muIL8Rh regulation of leukocyte populations upon allergic challenge

| cell type | mouse genotype | Cir. Blood Cells | Infiltr. cells (BAL) | Infiltr. cell % of Cir. cell | WT:KO ratio |
|---|---|---|---|---|---|
| eos | WT | 1293566 | 422348 | 32.65 | 1.97 |
|  | KO | 336697 | 55877 | 16.60 |  |
| lympho | WT | 6596926 | 156121 | 2.37 | 2.47 |
|  | KO | 7247362 | 69341 | 0.96 |  |
| neutro | WT | 2442790 | 12529 | 0.51 | 18.31 |
|  | KO | 4190160 | 1174 | 0.03 |  |

The ovalbumin-specific IgE titers in control and asthmatic animal sera (FIG. 32) confirmed that all the animals in the asthmatic group had been sensitized to ovalbumin during the course of the daily ovalbumin aerosol exposure. Thus, the reduced eosinophil response observed in KO asthmatics was not due to the absence of allergen sensitization. Since eosinophils are known to contribute to the pathogenesis of asthma by synthesizing leukotriene C4, stimulating histamine release from mast cells and basophils and releasing the major basic protein, the reduced eosinophil response is indicative of an improvement in the overall pathology of the asthmatic mouse lung.

Figure 30:
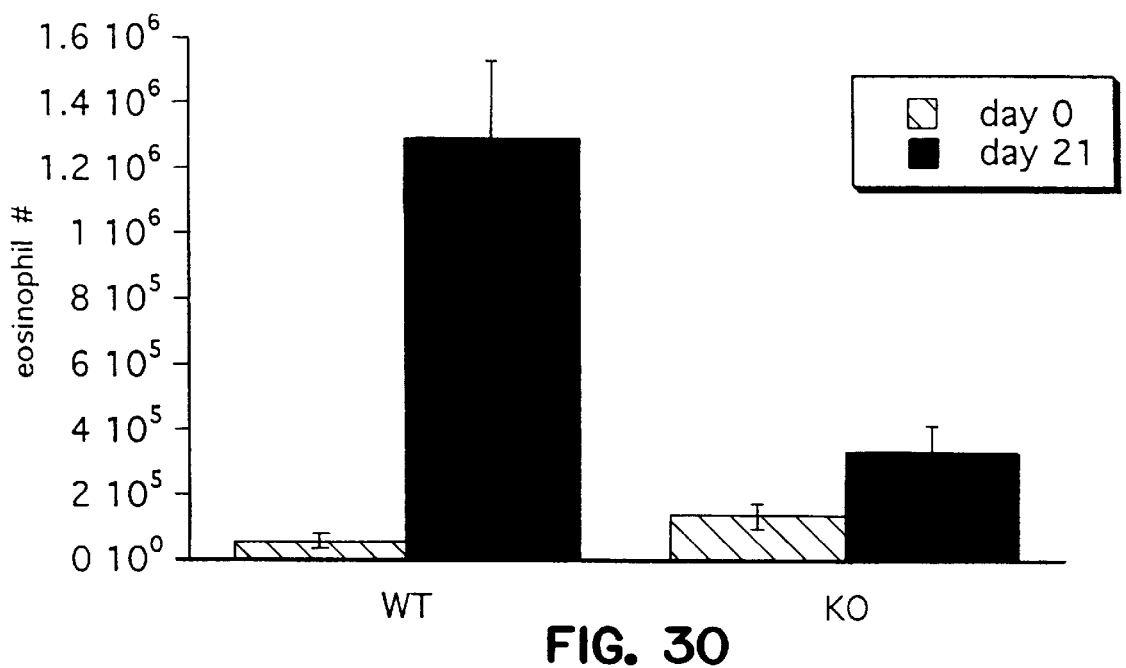
FIG. 30 is a graph depicting the effect of the absence of IL8Rh on peripheral eosinophil counts in an asthma model using wild type and IL8Rh knock-out mice. Peripheral eosinophil levels are presented as circulating blood eosinophil cell counts. Cell counts for wild type and KO mice that were intraperitoneally (ip) inoculated with ovalbumin allergen and subsequently exposed to aerosolized allergen are denoted as "WT" and "KO", respectively. Cell counts obtained on day 0 (before ip inoculation of allergen) are depicted as diagonally hatched columns. Cell counts obtained on day 21 (the day following completion of aerosolized allergen challenge) are depicted as solid columns.
Figure 33:
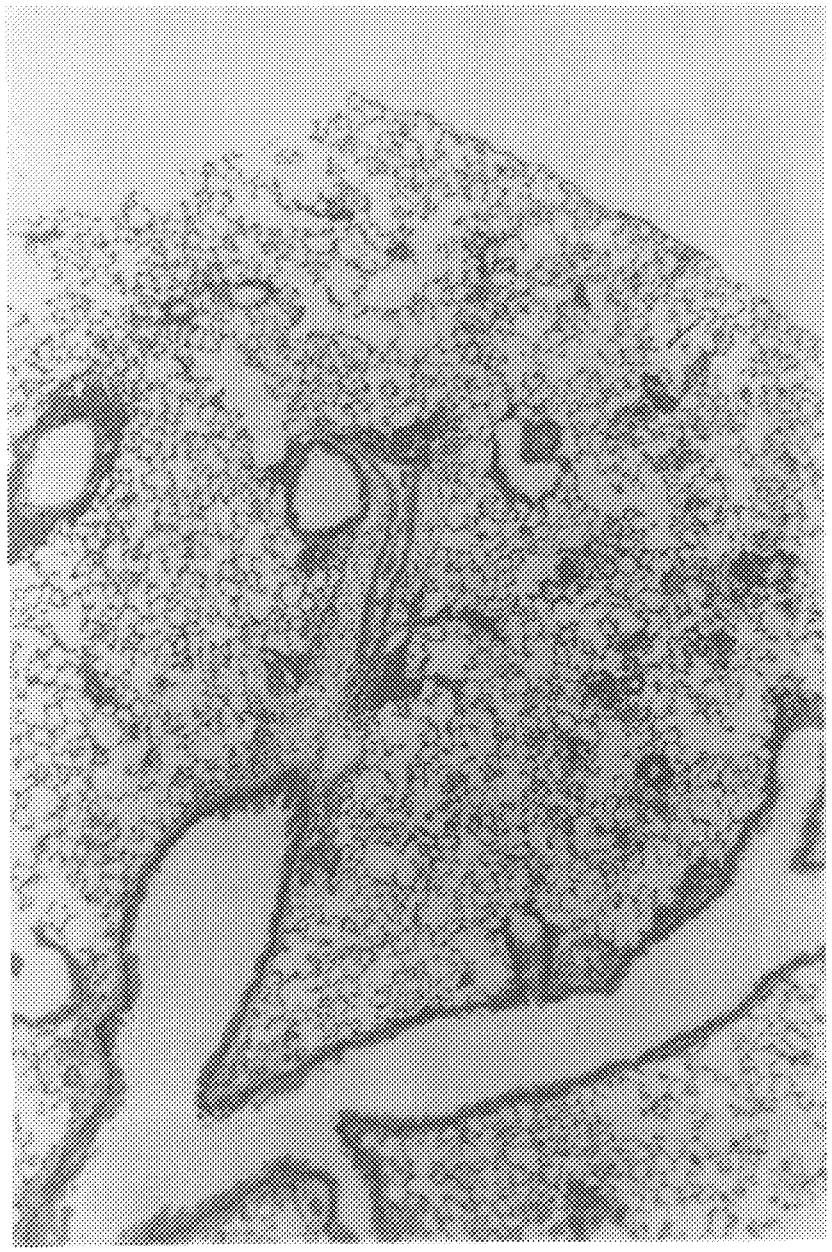
FIGS. 33–35 are photomicrographs depicting the lung histology of the most severely affected WT asthmatic mouse. Photomicrographs of a single specimen of lung tissue were taken at 40×, 200× and 320× magnification, shown in FIGS. 33–35, respectively.
Figure 34:
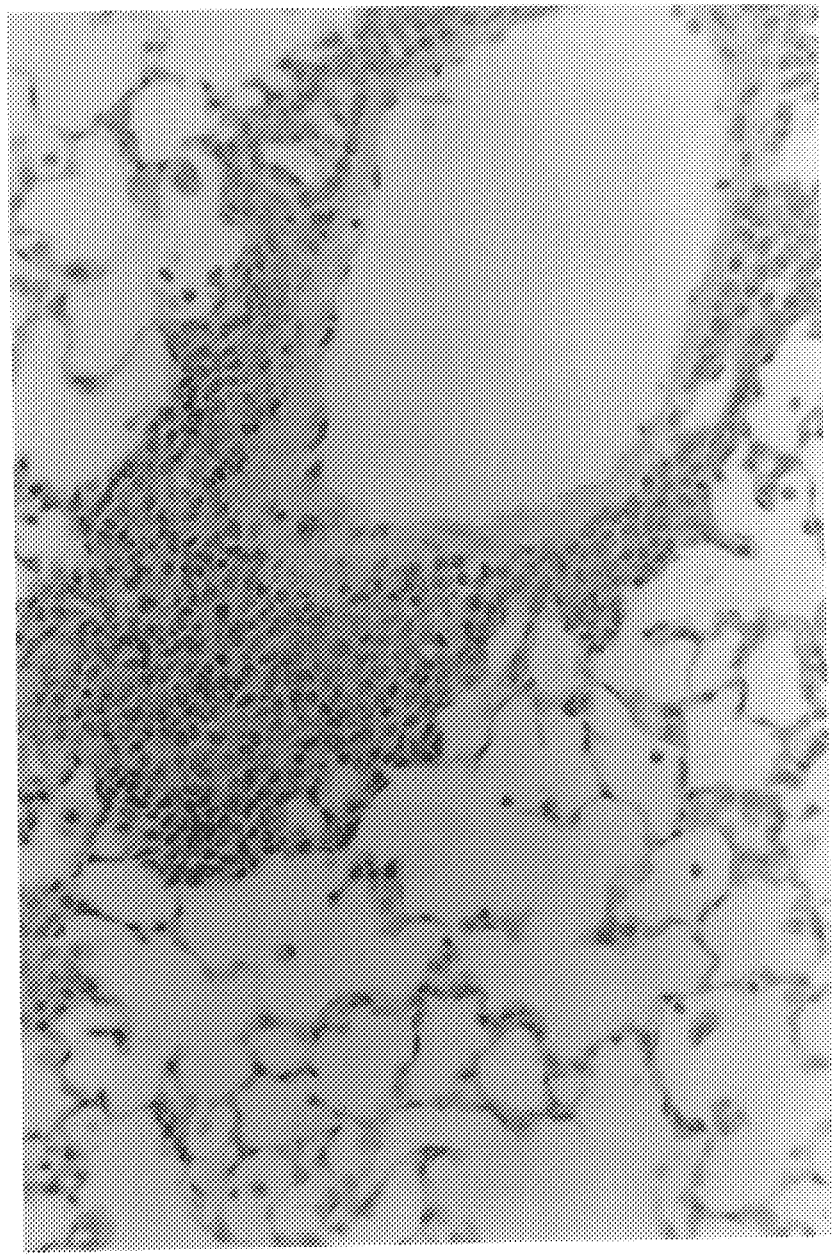
Figure 35:
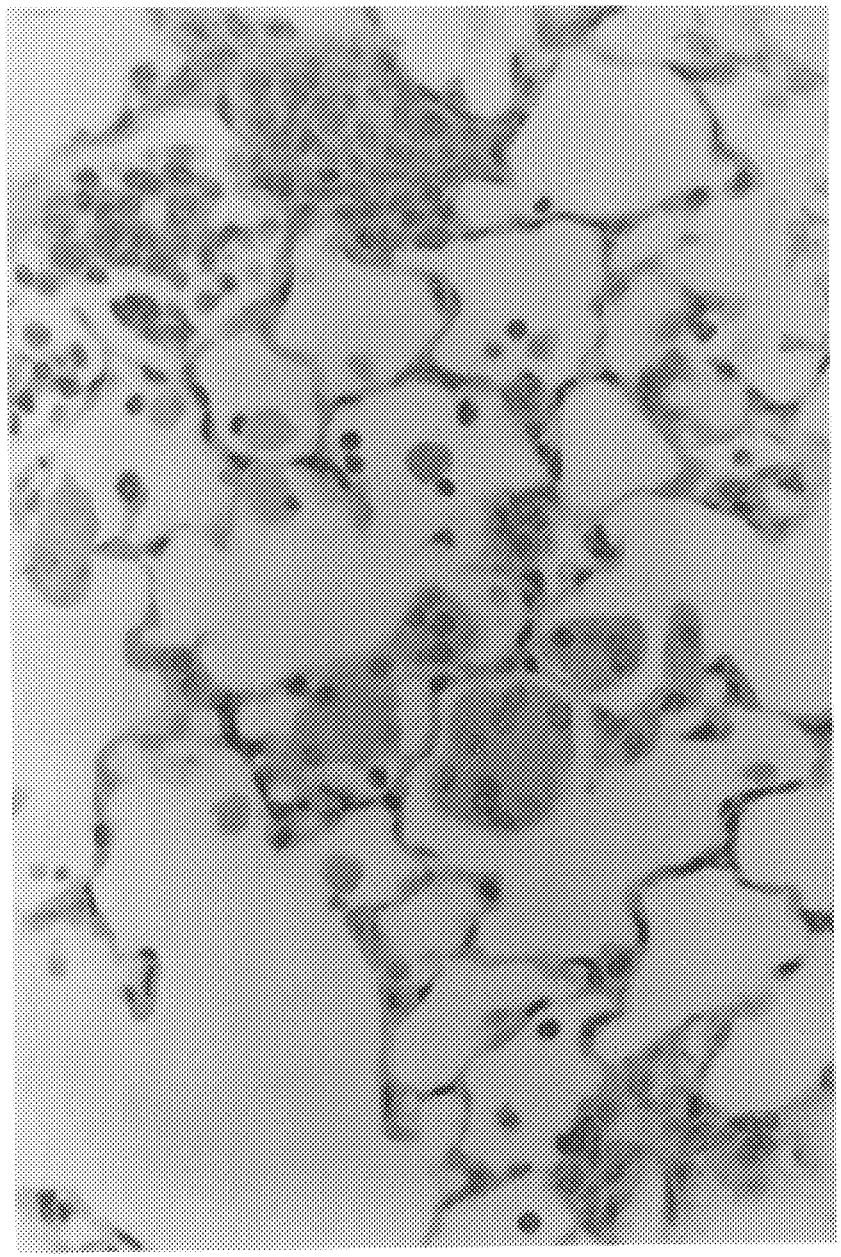
Figure 36:
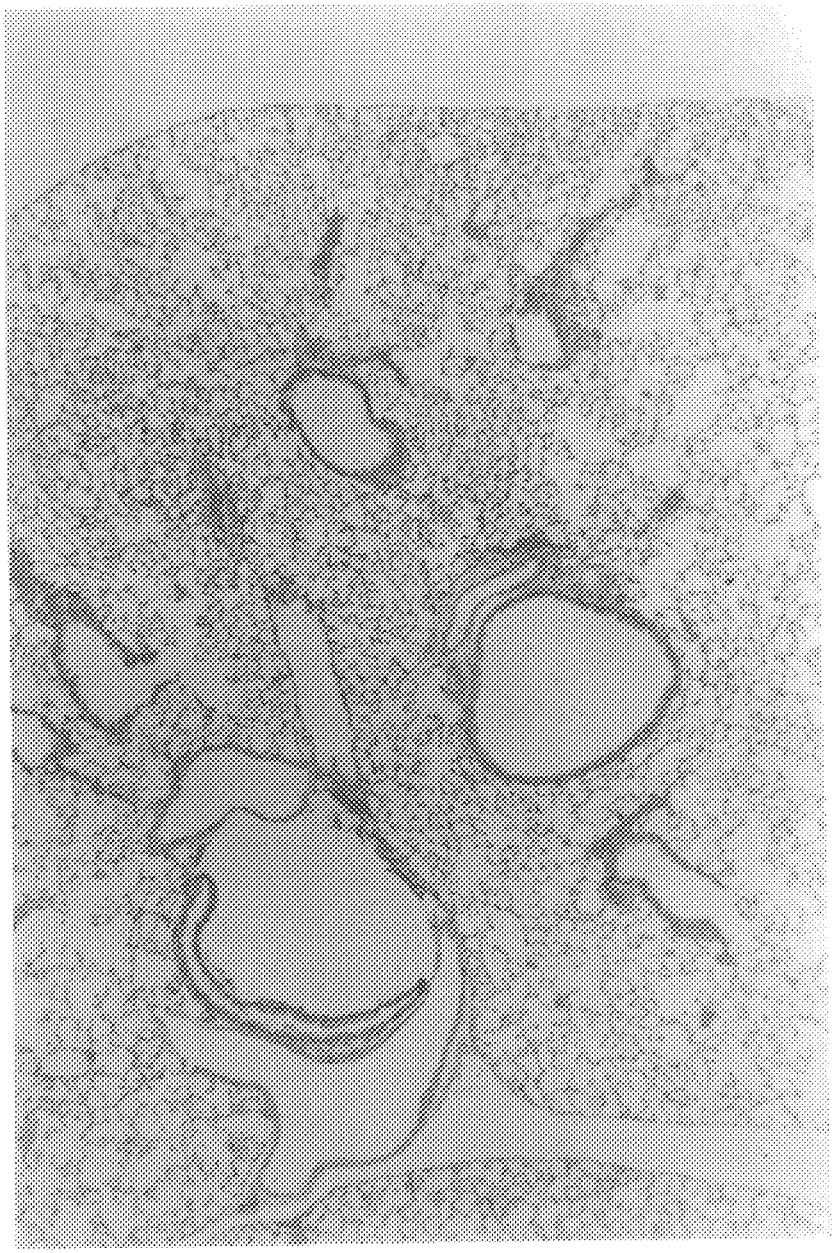
FIGS. 36–38 are photomicrographs depicting the lung histology of the least affected WT asthmatic mouse. Photomicrographs of a single specimen of lung tissue were taken at 40×, 200× and 320× magnification, shown in FIGS. 36–38, respectively.
Figure 37:
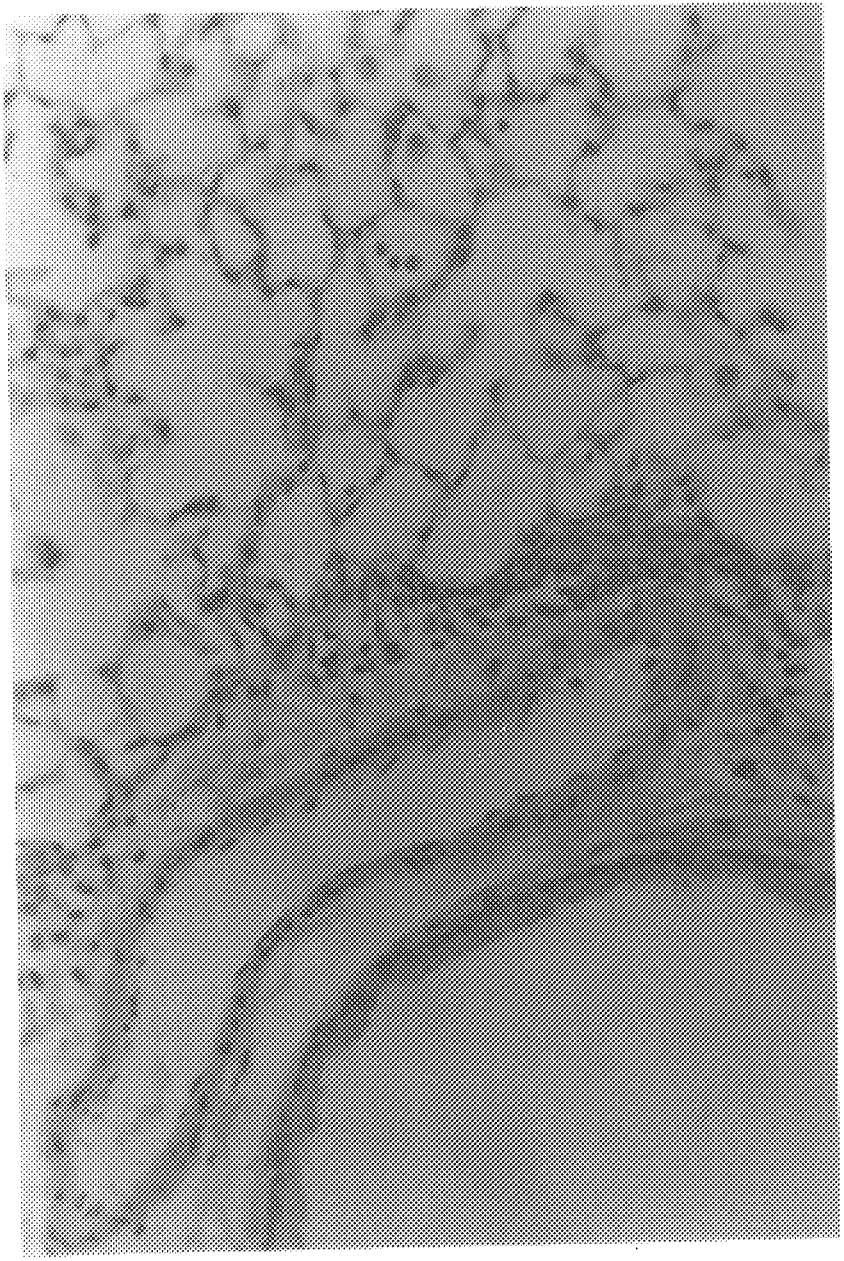
Figure 38:
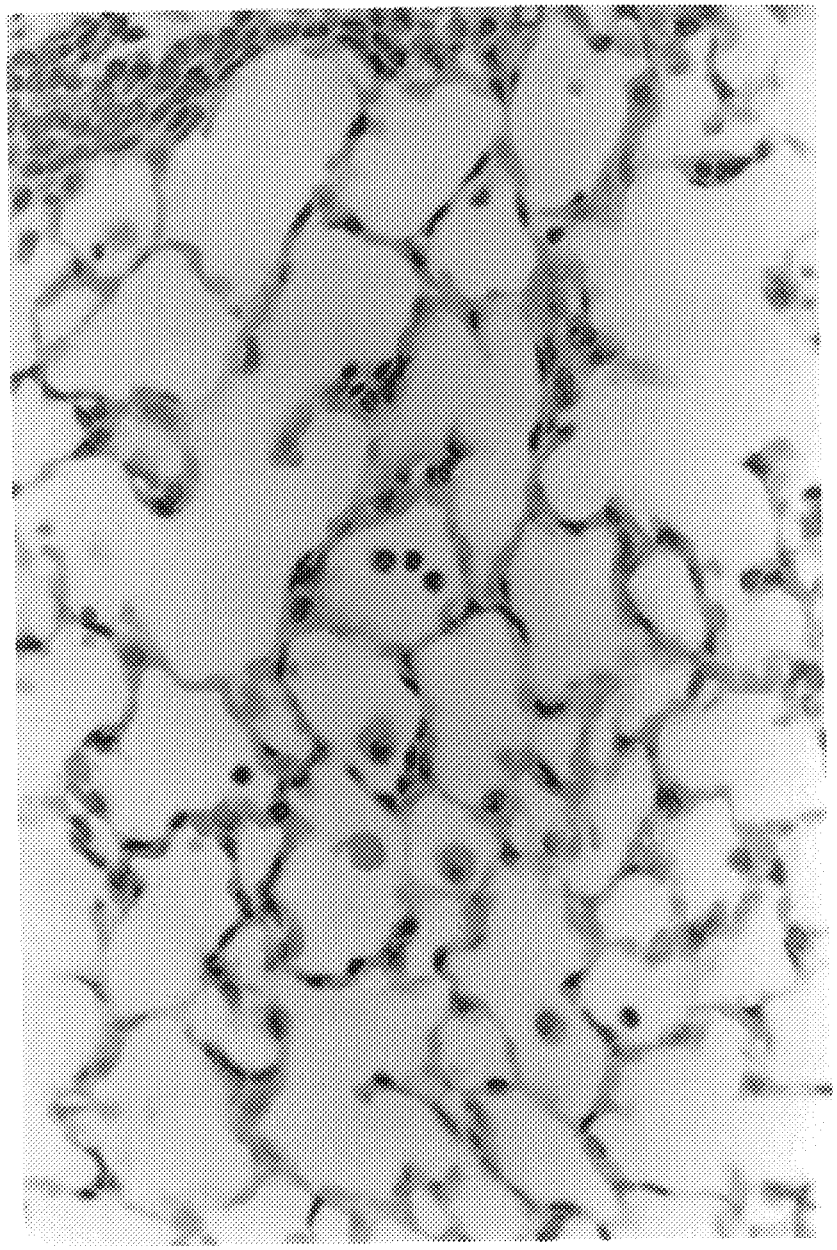
Figure 39:
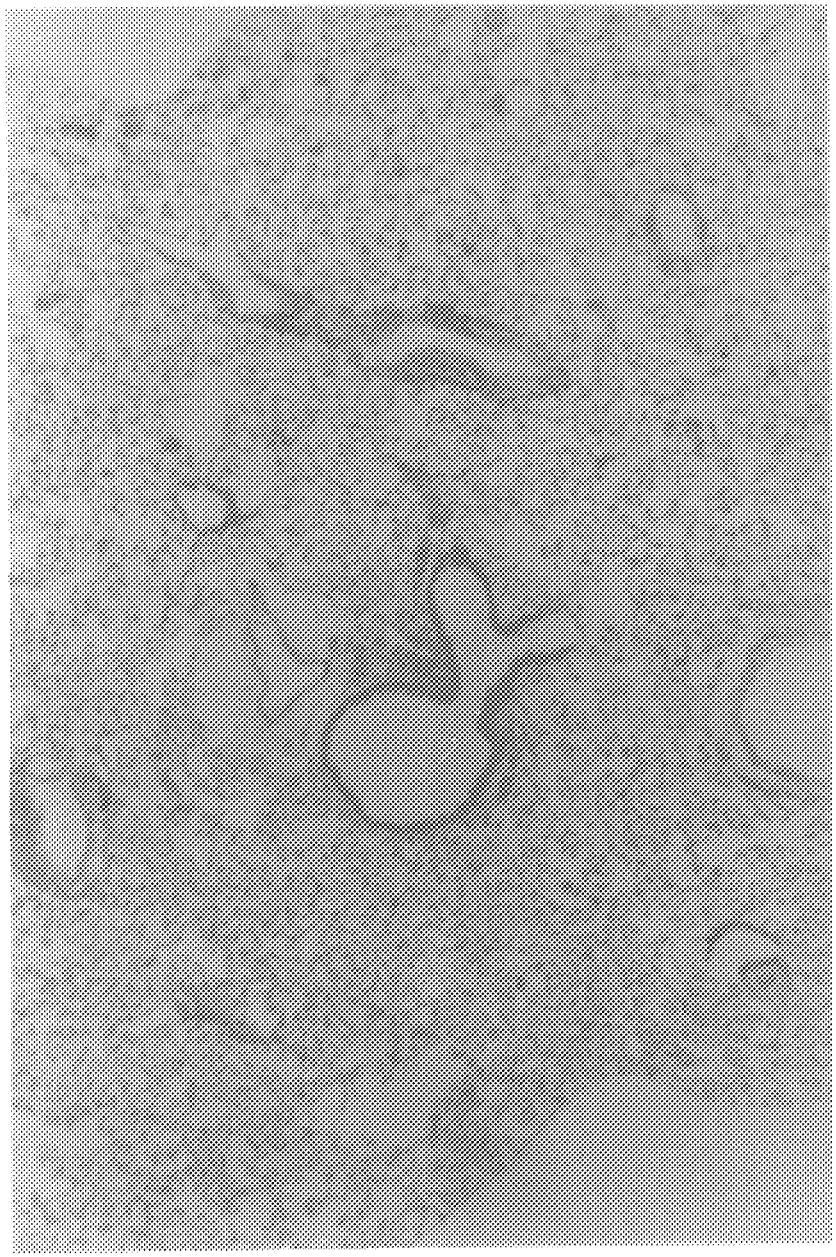
FIGS. 39–41 are photomicrographs depicting the lung histology of the most severely affected IL8Rh KO asthmatic mouse. Photomicrographs of a single specimen of lung tissue were taken at 40×, 200× and 320× magnification, shown in FIGS. 39–41, respectively.
Figure 40:
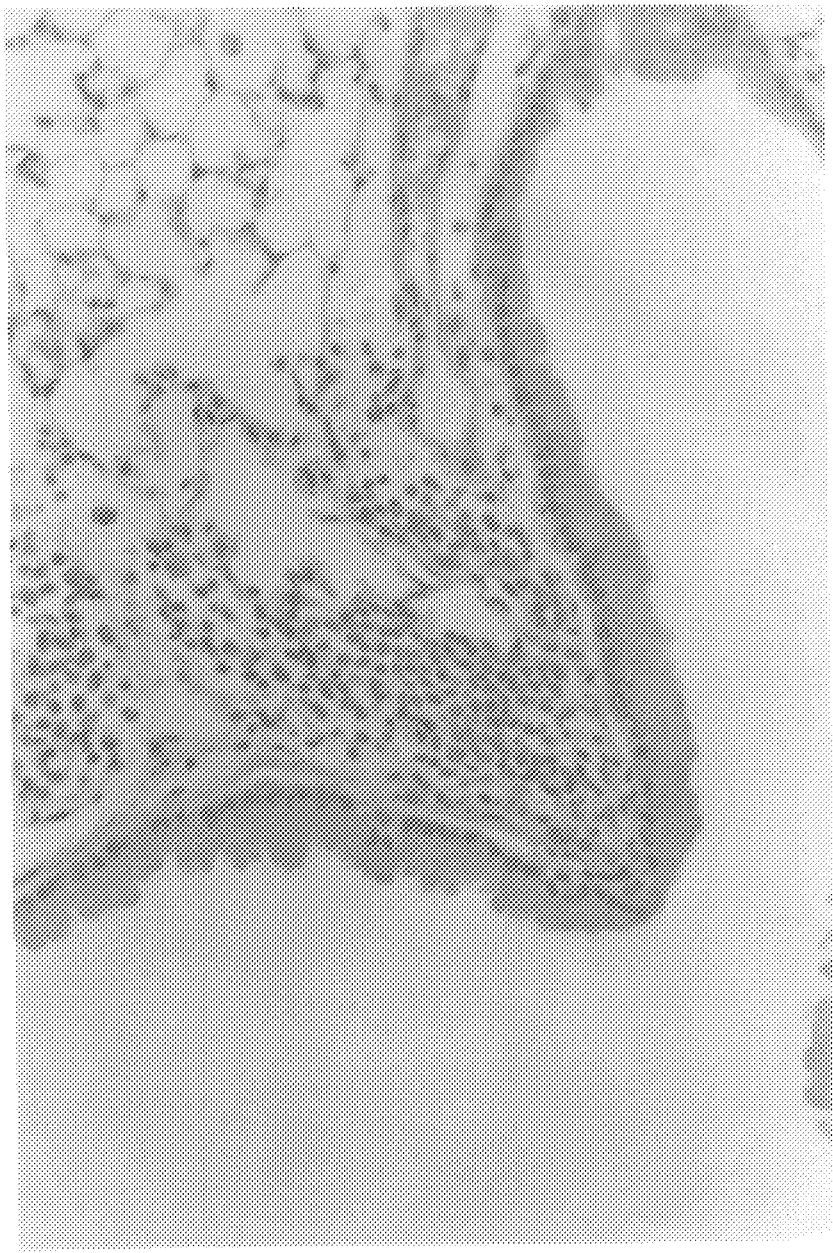
Figure 41:
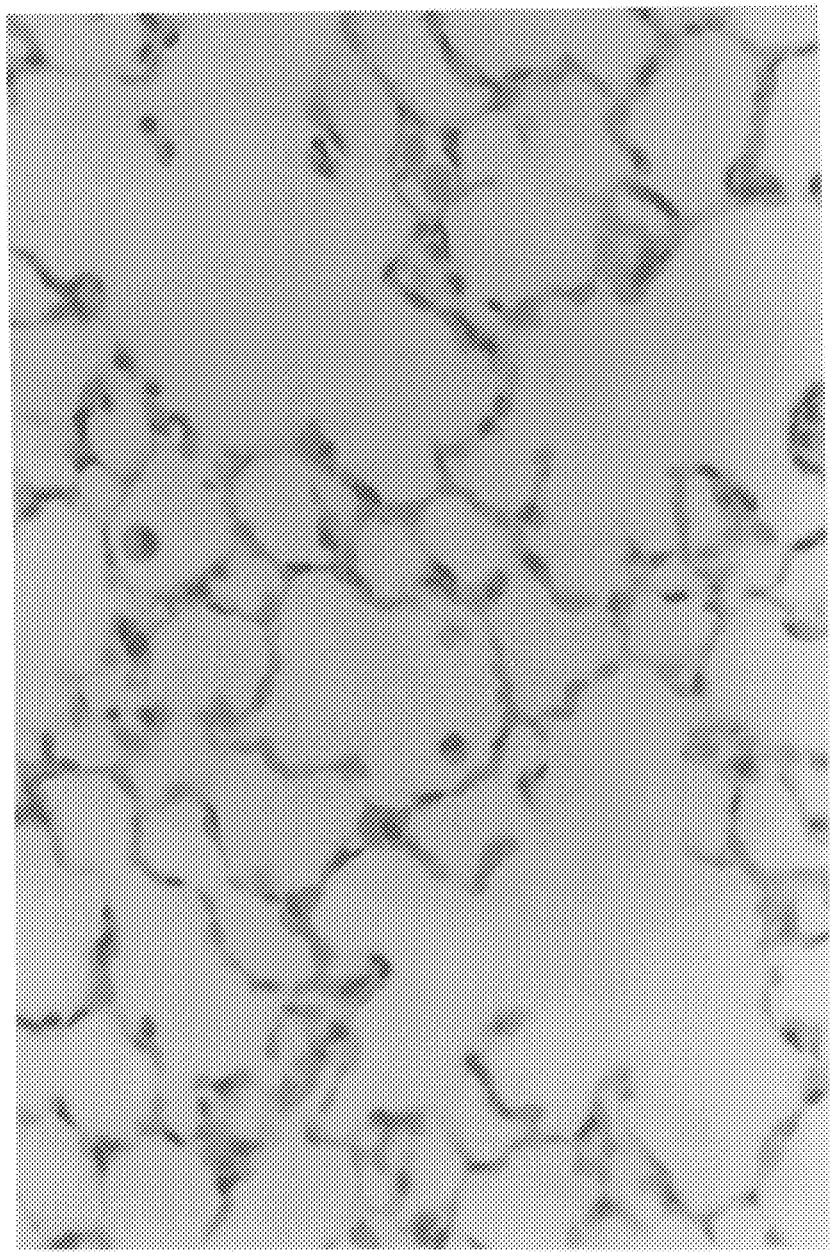

The deletion of the IL8Rh can reduce the lung eosinophil infiltration by directly affecting transmigration of cells into the lung and by indirectly regulating the proliferation and/or circulating half-life of eosinophils. As shown in FIG. 30, the peripheral blood eosinophil count in the asthmatic WT animals increased 24-fold upon repeated stimulation with allergen, while the KO animals exhibited a 3-fold increase. Since human asthmatics also present elevated levels of circulating eosinophils, these data strongly indicate that IL-8 plays a pivotal role in the development of eosinophilia in humans.

As shown in Table II above and in FIG. 31, the KO mice in comparison to WT mice exhibited a two fold reduction in the ratio of infiltrating versus circulating eosinophils. This is a strong indication that the murine IL8Rh (muIL8Rh) is directly involved in allowing eosinophils to move across the endothelium and epithelium of the lung into the lumen of the airways. This transmigration impairment was also observed for lymphocytes and neutrophils. As shown in Table II above, asthmatic IL8Rh KO mice presented a 2.5-fold and 18-fold reduction in the number of lymphocytes and neutrophils, respectively, in the bronchoalveolar lavage when compared to WT asthmatics. These data are of particular significance in light of the fact that human lymphocytes and neutrophils are known to have IL-8 receptors and eosinophils from asthmatic human donors are known to display IL-8 receptors as well.

The overall effect of muIL8Rh in the leukocyte infiltration response is clear from the microscopic analysis of lung sections shown in FIGS. 33–41. Even though the KO mice still presented a mild pulmonary infiltration of leukocytes, the overall severity was greatly reduced compared to WT animals, which were on average moderately and even markedly infiltrated. Even in the less severe WT asthmatics, almost every bronchius and blood vessel was peripherally infiltrated to some extent with monocytes and eosinophils (shown in FIGS. 36–38), while in the most affected KO animal only the major branches were affected (shown in FIGS. 39–41).

Since this murine asthma model reproduces many of the key physiological features of human allergic asthma and since the muIL8Rh plays such a dramatic role in the development of several asthma symptoms, these data strongly indicate that IL-8 plays an important role in the pathogenesis of asthma in humans, especially with regard to the control of the leukocyte infiltration response. The use of an IL-8 antagonist can reduce the pool of circulating eosinophils to close to baseline levels and improve the overall pathology of the lung by diminishing the number of infiltrating eosinophils and lymphocytes. Since eosinophils stimulate mast cells and basophils to release histamine, which is responsible for inducing smooth muscle contraction and consequently bronchoconstriction, treatment with IL-8 antagonists is expected to decrease the intensity and/or the frequency of airflow obstruction and improve the overall lung function of asthmatic patients.

The treatment of asthma with an IL-8 antagonist is investigated by using a primate asthma model in which asthma is induced by intraperitoneal injection of allergen followed by aerosolization with allergen using a protocol similar to that of the murine asthma model described above. The allergen used is ovalbumin or any other antigen known to cause allergy in humans such as dust mite, ragweed, cat dander, etc. A prophylactic treatment modality is investigated by pretreating animals with anti-IL-8 antibody administered intravenously in a single bolus dosage of about 0.1 to 10 mg/kg (or with a small molecule IL-8 antagonist administered intravenously at a dosage to be determined according to the pharmacodynamic profile of the compound) up to about 10 minutes prior to the induction of asthma by aerosolization with allergen as described above. Pretreatment with IL-8 antagonist is expected to prevent or reduce the onset of symptoms resulting from the induction of asthma. Similarly, a therapeutic treatment modality is investigated by inducing asthma in animals as described above, and treating the animals following onset of asthma with an anti-IL-8 antibody administered intravenously in a single bolus dosage of about 0.1 to 10 mg/kg (or with a small molecule IL-8 antagonist administered intravenously at a dosage to be determined according to the pharmacodynamic profile of the compound). Therapeutic treatment with IL-8 antagonist after onset is expected to reduce or eliminate symptoms resulting from the induction of asthma.

We claim:

1. A method for treating asthma in a mammal comprising administering to the mammal a therapeutically effective amount of an anti-IL-8 monoclonal antibody having the following characteristics; ability to bind human IL-8 with a Kd between about, $1\times10^{-8}$ to about $1\times10^{31\ 11}$M, ability to inhibit neutrophil chemotaxis in response to IL-8, and ability to inhabit IL-8 mediated clastase release by neutrophils; wherein the monoclonal antibody does not bind to C5a, β-TG or platelet factor 4.

2. The method of claim 1 wherein the asthma is allergic asthma.

3. The method of claim 1 wherein the mammal is a human.

4. The method of claim 1 wherein the anti-IL-8 antibody is administered before the onset of asthma in the mammal.

5. The method of claim 1 wherein the anti-IL-8 antibody is administered after the onset of asthma in the mammal.

6. The method of claim 1 wherein the anti-IL-8 antibody is a chimeric antibody.

7. The method of claim 1 wherein the anti-IL-8 antibody is a humanized antibody.

8. The method of claim 1 wherein the anti-IL-8 antibody comprises an antigen binding site comprising the complementarity determining regions of the light chain polypeptide of FIG. 24 (SEQ ID NO:48) and the complementarity determining regions of the heavy chain polypeptide of FIG. 25 (SEQ. ID NO:50).

9. The method of claim 1 wherein the anti-IL-8 antibody comprises an antigen binding site comprising the complementarity determining regions of the light chain polypeptide of FIG. 16 (SEQ ID NO:20) and the complementarity determining regions of the heavy chain polypeptide of FIG. 17 (SEQ ID NO:22).

10. The method of claim 1 wherein the anti-IL-8 antibody is administered by inhalation.

11. The method of claim 1 wherein the anti-IL-8 antibody is administered systemically.

12. The method of claim 1 wherein the anti-IL-8 antibody is administered by continuous infusion.

13. The method of claim 1 wherein the anti-IL-8 antibody is administered by bolus dosage.

* * * * *

UNITED STATES PATENT AND TRADEMARK OFFICE
CERTIFICATE OF CORRECTION

PATENT NO. : 5,874,080

DATED : FEBRUARY 23, 1999

INVENTOR(S) : HEBERT, C. ET AL.

It is certified that error appears in the above-identified patent and that said Letters Patent is hereby corrected as shown below:

In Claim 1, line 5, delete "about, $1 \times 10^{-8}$ to about $1 \times 10^{31\ 11}$M" and insert therefor --about $1 \times 10^{-8}$ to about $1 \times 10^{-11}$M--.

In Claim 1, line 7, delete "clastase" and insert therefor --elastase--.

Signed and Sealed this

Seventeenth Day of April, 2001

NICHOLAS P. GODICI

*Attest:*

*Attesting Officer*       Acting Director of the United States Patent and Trademark Office